(12) United States Patent
Cuppens

(10) Patent No.: US 12,297,495 B2
(45) Date of Patent: May 13, 2025

(54) METHODS FOR IDENTIFICATION OF SAMPLES

(71) Applicant: DName-iT NV, Heverlee (BE)

(72) Inventor: Harry Cuppens, Brussels (BE)

(73) Assignee: DName-iT NV, Heverlee (BE)

( * ) Notice: Subject to any disclaimer, the term of this patent is extended or adjusted under 35 U.S.C. 154(b) by 0 days.

(21) Appl. No.: 16/302,345

(22) PCT Filed: May 17, 2017

(86) PCT No.: PCT/EP2017/061902
§ 371 (c)(1),
(2) Date: Nov. 16, 2018

(87) PCT Pub. No.: WO2017/198742
PCT Pub. Date: Nov. 23, 2017

(65) Prior Publication Data
US 2019/0300948 A1    Oct. 3, 2019

(30) Foreign Application Priority Data

May 17, 2016   (EP) ..................................... 16169997
Feb. 6, 2017    (GB) ..................................... 1701908

(51) Int. Cl.
*C12Q 1/6869*    (2018.01)
*B01L 3/00*      (2006.01)

(52) U.S. Cl.
CPC ............ *C12Q 1/6869* (2013.01); *B01L 3/545* (2013.01); *B01L 2300/021* (2013.01)

(58) Field of Classification Search
CPC .. C12Q 1/6869; B01L 3/545; B01L 2300/021
See application file for complete search history.

(56) References Cited

U.S. PATENT DOCUMENTS

| | | | |
|---|---|---|---|
| 5,776,737 A | 7/1998 | Dunn | |
| 6,030,657 A | 2/2000 | Butland et al. | |
| 6,312,911 B1 | 11/2001 | Bancroft et al. | |
| 7,803,550 B2 | 9/2010 | Makarov et al. | |
| 8,785,130 B2 | 7/2014 | Vinayagamoorthy | |
| 2002/0129251 A1 | 9/2002 | Itakura et al. | |
| 2009/0298049 A1 | 12/2009 | Kurnool et al. | |
| 2010/0285985 A1 | 11/2010 | Liang et al. | |
| 2012/0115154 A1 | 5/2012 | Hampikian | |
| 2012/0135413 A1 | 5/2012 | Brown et al. | |
| 2014/0272973 A1 | 9/2014 | Mercolino et al. | |
| 2015/0083797 A1 | 3/2015 | Tran et al. | |
| 2015/0141257 A1 | 5/2015 | Albert et al. | |
| 2015/0141264 A1 | 5/2015 | Jung et al. | |
| 2015/0322508 A1 | 11/2015 | Mitne Neto et al. | |
| 2017/0136458 A1* | 5/2017 | Dunne | B01L 3/5025 |

FOREIGN PATENT DOCUMENTS

| | | | | |
|---|---|---|---|---|
| EP | 1488039 A1 | 12/2004 | | |
| EP | 2201143 A2 | 6/2010 | | |
| WO | 03052101 A1 | 6/2003 | | |
| WO | WO2003052101 | * 6/2003 | ............. | C12N 15/11 |
| WO | 2005093641 A1 | 10/2005 | | |
| WO | WO2012019765 | * 2/2012 | ............. | C12N 15/10 |
| WO | WO2012106385 | * 8/2012 | ............... | C12Q 1/68 |
| WO | 2014005184 A1 | 1/2014 | | |

OTHER PUBLICATIONS

Tanabe et al (Archaea vol. 2015 twenty pages) (Year: 2015).*
A. Calabria, et al., ; adLIMS: "a customized open source software that allows bridging clinical and basic molecular research studies", BMC Bioinformatics, Biomed Central, London, GB; vol. 16, No. Suppl. 9; Jun. 1, 2015, p. S5.
N.J. Lennon et al,; "A Scalable, Fully Automated Process for Construction of Sequence-Ready Barcoded Libraries for 454"; Genome Biology, Biomed Central Ltd., London, GB; vol. 11, No. 2; Feb. 5, 2010; p. R15.
International Search Report and Written Opinion pertaining to corresponding International Patent Application No. PCT/EP2017/061902 mailed Sep. 18, 2017.
Norton et al., (2015) N. Engl. J. Med 372:1589-1597.
Taylor et al. (2015) Nat. Genetics 47:717-726.
23andMe. http://blog.23andme.com/23andme-and-you/update-from-23andme/ (Jun. 8, 2010).
Akmaev VR, Wang CJ. (2004) Bioinformatics 20:1254-1263.
De Bruyn A, Martin DP, Lefeuvre P. (2014) Methods Mol. Biol. 1115:257-277.
Hamady M. Walker JJ, Harris JK, Gold NJ, Knight R. (2008) Nat Methods 5:235-237.
Buschmann T, Bystrykh LV. (2013) BMC Bioinformatics 14:272.

* cited by examiner

*Primary Examiner* — Christopher M Gross
(74) *Attorney, Agent, or Firm* — DINSMORE & SHOHL LLP

(57) ABSTRACT

The present invention describes methods, carriers, and vectors relating to nucleic acids for labelling an item, wherein each carrier comprises at least 2 nucleotide barcode nucleic acids, other than sample nucleic acid, for labelling, wherein each nucleotide barcode nucleic acid comprises a different minimal nucleotide barcode sequence with a length of at least 4 nucleotides, where at least two of said different nucleotide barcode nucleic acids have a minimal nucleotide barcode sequence of the same length, wherein the combination of these different nucleotide barcode nucleic acids generates a transferable molecular identification barcode, whereby each such transferable molecular identification barcode is different for each of the carriers in the collection.

10 Claims, 15 Drawing Sheets

Specification includes a Sequence Listing.

| CFS1 | MNB | CFS2 |

| CFS | MNB | | | |

| L1 | AP1 | L2 | MNB | L1 | CS | L2 |

| L1 | AP1 | L2 | ES1 | MNB | L3 | CS | AP2 | L4 |

| L1 | AP1 | L2 | ES1 | L3 | MNB | L4 | ES2 | L5 | CS | AP2 | L4 |

| L1 | AP1 | L2 | ES1 | MNB | ES2 | L3 | CS | AP2 | L6 |

| L1 | ASP1 | L2 | NBSIS1 | ES1 | MNB | ES2 | NBSIS2 | L3 | CS | ASP2 | L4 |

| L1 | ASP1 | L2 | NBSIS1 | ES1 | MNB | ES2 | NBSIS2 | L3 | CS | ASP2 |

CFS: Constant Flanking Sequence
CS: Capturing Sequence
ES: Extracting Sequence
L: Linker Sequence MNB: Minimal Nucleotide Barcode sequence
AP: Amplification Primer binding site
ASP: Amplification and Sequencing Primer binding site
NBSIS: Nucleotide Barcode Sequence Identifier Sequence

Figure 3

Amp1: Amplicon-specific sequence 1
CS1: constant sequence 1
PB1: pooling barcode 1
ASP1: binding site for sequencing primer 1

SEQUENCE LISTING

<160> NUMBER OF SEQ ID NOS: 20

<210> SEQ ID NO 1
<211> LENGTH: 401
<212> TYPE: DNA
<213> ORGANISM: Artificial Sequence
<220> FEATURE:
<223> OTHER INFORMATION: barcode flanking region

<400> SEQUENCE: 1

| aagctttgtg | gatgtacaag | tccacaccat | gtacactaga | cgcagcctgt | acagatatcc | 60 |
| atccagtgta | ctcactgtcg | acacggatcc | aatgcccggg | ttctgataga | cgaacgacga | 120 |
| gatgtgcagt | gacttcgagg | atcccagatg | tgcacgtagt | gcaggtagct | tgaatgacta | 180 |
| ctacgcctgt | agcatcatca | cgtagactcg | tacagctaca | tgacggtagc | tagattgacg | 240 |
| actcaagcat | gctagtgtcg | ttactgacct | gatgacacag | tcgatgcgac | cttaatacga | 300 |
| ctcactatag | ggtcaacaag | accctgcaga | tcccgggatc | cgcctcttaa | gctgcgcagg | 360 |
| ccaggaattg | cacgtcagag | cactaaggcc | gccaccatgg | c | | 401 |

<210> SEQ ID NO 2
<211> LENGTH: 401
<212> TYPE: DNA
<213> ORGANISM: Artificial Sequence
<220> FEATURE:
<223> OTHER INFORMATION: barcode flanking region

<400> SEQUENCE: 2

| aagctttgtg | gatgtacaag | tccacaccat | gtacactaga | cgcagcctgt | acagatatcc | 60 |
| atccagtgta | ctcactgtcg | acacggatcc | aatgcccggg | ttctgataga | cgaacgacga | 120 |
| gatgtgcagt | gacttcgagg | atcccagatg | tgcacgtagt | gcaggtagct | tgaatgacta | 180 |
| ctacgcctgt | agcatcatca | cgtagactcg | tacagctaca | tgacggtagc | tagattgacg | 240 |
| actcaagcat | gctagtgtcg | ttactgacct | gatgacacag | tcgatgcgac | cttaaatgct | 300 |
| gagagattag | ggtcaacaag | accctgcaga | tcccgggatc | cgcctcttaa | gctgcgcagg | 360 |
| ccaggaattg | cacgtcagag | cactaaggcc | gccaccatgg | c | | 401 |

<210> SEQ ID NO 3
<211> LENGTH: 401
<212> TYPE: DNA
<213> ORGANISM: Artificial Sequence
<220> FEATURE:
<223> OTHER INFORMATION: constant sequence

<400> SEQUENCE: 3

| aagcttctct | cgccagctat | ttaaagtacg | agtcgggagg | ccttagcacg | aactgatttt | 60 |
| tccagcctga | gtgctgttct | tgcatgtacc | ttctatctaa | cgacgtccgt | aataggaagt | 120 |
| ataccaggtc | gaactaacga | ctcctttgcc | gtagcgagtg | tttcgccaaa | agtgtctggg | 180 |
| tctactggcc | accgtccagc | atttctatgc | ccgtaccagg | accttcgtg | taatccccca | 240 |
| tggattttca | agaattgagg | aaaagtcacg | tctccaaggc | cctacagggc | cagcggatac | 300 |
| tttgaaagcg | acgataatat | ggtcgcttat | ttcatccaag | ccccgcgcta | aacatggatt | 360 |
| tgggatgct | atcccgaaag | tacgacttgg | ctccaaaggc | c | | 401 |

<210> SEQ ID NO 4
<211> LENGTH: 401
<212> TYPE: DNA
<213> ORGANISM: Artificial Sequence
<220> FEATURE:
<223> OTHER INFORMATION: barcode flanking region

<400> SEQUENCE: 4

```
aagcttaact tcagctgaag acccgttttc gatccgcggc gagcccggag tgtaaaacga      60
tagacgtgat gcttcggtct tctcacccct tcgaggtcat aacattttg tcatgattgc     120
cgtagtgctg atagtcctga gtctaaggca ttcaatacaa cgtacctcag gtcaattaga    180
ctgtccatga ctcatcttcc gaagcgcaga atgatacgca gttctcacta gttgggacct   240
gctcgacgtc cggttaaggc ggatttaact aagcataggg taccgtcacc tgggcaactg   300
aaaatggcct ctgtgacgca agatgcatgt tcggtcagct cgttcaaaga cggtatgaaa   360
tagagtagac atcagtacat cactcggaca ggagcaccta t                       401
```

<210> SEQ ID NO 5
<211> LENGTH: 401
<212> TYPE: DNA
<213> ORGANISM: Artificial Sequence
<220> FEATURE:
<223> OTHER INFORMATION: barcode flanking region

<400> SEQUENCE: 5

```
aagcttgcgc aactttgacg aaatgttggc caatagcata cccgaacacc gcagggttaa    60
tgcctacagc tagtgttagt cgttccggta gacatctgtt aaagccggaa gctcgcccga   120
ctgtacgaaa tcacatctaa ctatacaact gcgccacttt gcaaatcgag tcacgacgac   180
ctgtccctta cggtgcccat ttgcgctgta atgccgatca cttcacacaa acaaggcgct   240
tgagagctcg aacttaggcg atgagggaca agtggtaccc aagctccaat agtagaatgt   300
gtaccatagg gccgcggcga gccgcctttg tatcctgaaa aaattctcat cggcagcgca   360
gtttattatt tagttggaag cattagtgaa cataacagcg c                       401
```

<210> SEQ ID NO 6
<211> LENGTH: 401
<212> TYPE: DNA
<213> ORGANISM: Artificial Sequence
<220> FEATURE:
<223> OTHER INFORMATION: barcode flanking region

<400> SEQUENCE: 6

```
aagcttccgt ggtgggcaga agagcctagc ttactcttta tttaaaaacg ccagtagaat    60
ttggtcggga ggatacgatc cactgtccaa cataaataac ccgctgtagc ctttacacat   120
tcacgggtta agtgtagtgc gtgttctgtg tttctggttt gaataactgt tcccactgtc   180
ttgaggatcg attctggcca aaatgtatga ccctctacat aggatgtacc cctggggtag   240
gacggaatcg attacgaccc ctgatgataa tgaccaatcg tgacggtcgg tgtctactga   300
cttcgcctac atccgacgat cctggctagg cgggttgaga acatcacggt attggggatc   360
gggatgcgcg atcgcgataa tgtggacttc gcaggtagta g                       401
```

<210> SEQ ID NO 7
<211> LENGTH: 401
<212> TYPE: DNA
<213> ORGANISM: Artificial Sequence
<220> FEATURE:
<223> OTHER INFORMATION: barcode flanking region

<400> SEQUENCE: 7

```
aagcttggtg gagcgcaaat tctatttctg agttgcggcg tcagttgcca ttgaagtgcc    60
```

| | |
|---|---|
| cgagctgcat agtctcacgg tgagtcctct tgtacgacca ctagatgcaa tgaagcgtgc | 120 |
| atggagcgcc actctgcaat aaaagccgaa acgctctgta aacaagatta atgtctcgtg | 180 |
| atgctctgaa accgtttacc taacacgaac gataagacgc aacatcttcc agagatgatt | 240 |
| acccgacacg ctaatgaccg ttatcactcc ccgcacatct gagcgtactt tttgaagtcc | 300 |
| cgaggattgt cacggactaa atacctcgaa tatcctgaac tacctttgcc aatggaggga | 360 |
| aggacaggga cacgctgtcg gtactttgta ggcatttggg t | 401 |

<210> SEQ ID NO 8
<211> LENGTH: 401
<212> TYPE: DNA
<213> ORGANISM: Artificial Sequence
<220> FEATURE:
<223> OTHER INFORMATION: barcode flanking region

<400> SEQUENCE: 8

| | |
|---|---|
| aagcttagct cgacgcacaa tccaacaagt agcactgctg tctactaagc aacgtaatga | 60 |
| tccattcaga cgagtttgga atgatctgcc tcacccaaag cattaggcag cccctagct | 120 |
| ttctatagga gaccgaaaga gcatgagaga gaactccctg atgacttact gactgcgtga | 180 |
| tggttggctc cgggacgcgc aacgcaacac tttgtgtggc acgtaacttg tcgcacatat | 240 |
| gtaatagctt caaacccgcc tcgtcttctg gtgtgcgctc gttcatttaa tcgaatagat | 300 |
| tcctctctct actgctggtc aagggcgtat tggaaataac aagcaagctc ctccgagctg | 360 |
| agctacgagt cgatccgccc atgttccctc attatcgtct g | 401 |

<210> SEQ ID NO 9
<211> LENGTH: 401
<212> TYPE: DNA
<213> ORGANISM: Artificial Sequence
<220> FEATURE:
<223> OTHER INFORMATION: barcode flanking region

<400> SEQUENCE: 9

| | |
|---|---|
| aagcttgacc tgtagcaccg caaataatca ttgctaatac gattcaagaa tcgccctcgt | 60 |
| tatttgtatt cacaggtgac ccttggcttc tactctaaca cctaaggctg atccaactca | 120 |
| gacttaagcg gcgcagccgc aaatgtaata tgttcactga gagagagacg acggctccgt | 180 |
| aggtcgaaca ttcaggtagc tggagagatc attgcttagc atggcgctcg cggatctgtt | 240 |
| actgcaaatg gcaacagact agaaaacagg cctaatatga tctcggaatt ttcgcctaac | 300 |
| acgctccttt gactggctgt gaggcctaag cgattctggc agcgctgtga cttatcaaga | 360 |
| cacgcatgtc actacttgac cggcatcgtg ccactctacg c | 401 |

<210> SEQ ID NO 10
<211> LENGTH: 401
<212> TYPE: DNA
<213> ORGANISM: Artificial Sequence
<220> FEATURE:
<223> OTHER INFORMATION: barcode flanking region

<400> SEQUENCE: 10

| | |
|---|---|
| aagcttttct ctgcaacagg cgactatcgg ggccgggtgc caatctttca aaagtgtgta | 60 |
| aacgtgcgac cgccagatgt catgattcaa tgtcttacct cgggctatcg tcataataag | 120 |
| tttctaccgt aaggcacgcc ctaaggacgt tccgaataaa cacgcacccc cccgtcgttt | 180 |
| cagaaatctc attaccggct gacatgcctt tagatacctc agagaaatct aaccacgtgt | 240 |
| gttacgactg acgtctcaaa gagacgagct gctcctagct ttcctattgg agtatctgtg | 300 |

```
cctcttgtgt cgggatttag tggatcaata tgctcccta cgataggtaa gatttacccg    360
ttcgtcaatt agagagccgg gttttattat tcggtcggca g                       401

<210> SEQ ID NO 11
<211> LENGTH: 400
<212> TYPE: DNA
<213> ORGANISM: Artificial Sequence
<220> FEATURE:
<223> OTHER INFORMATION: barcode flanking region

<400> SEQUENCE: 11
catcatcacc atcaccattg atctcccagc tgtgacacaa ataagctagc ccggggcagc    60
atggaggtta aaattgtgca tccgaccggc caggatacgt aatattaatg cgcaccgcgc   120
actgaagaat atgatcgagg ctcgctgtag cagcactcag aaaaaaaaaa aaaaaaaaaa   180
aaaaagagtg aataacactc agatctcggg ggcgtgaatg ctaaacatac acagagcacg   240
cggtgatgta taccgctatg tcggtcatgt gctacctaca aaagagctag gagtggatga   300
gcactacacg gtttcgggct aagaccatac tctcacacgt gtggatgact cgagacagca   360
gtgtcagagc atgtagctct agagatgaca cgatgaattc                         400

<210> SEQ ID NO 12
<211> LENGTH: 400
<212> TYPE: DNA
<213> ORGANISM: Artificial Sequence
<220> FEATURE:
<223> OTHER INFORMATION: barcode flanking region

<400> SEQUENCE: 12
catcatcacc atcaccattg atctcccagc tgtgacacaa ataagctagc ccggggcagc    60
atggaggtta aaattgtgca tccgaccggc caggatacgt aatattaatg cgcaccgcgc   120
actgaagaat atgatcgagg ctcgctgtag cagcactcag aaccgtaata ggaagtatac   180
caaaagagtg aataacactc agatctcggg ggcgtgaatg ctaaacatac acagagcacg   240
cggtgatgta taccgctatg tcggtcatgt gctacctaca aaagagctag gagtggatga   300
gcactacacg gtttcgggct aagaccatac tctcacacgt gtggatgact cgagacagca   360
gtgtcagagc atgtagctct agagatgaca cgatgaattc                         400

<210> SEQ ID NO 13
<211> LENGTH: 400
<212> TYPE: DNA
<213> ORGANISM: Artificial Sequence
<220> FEATURE:
<223> OTHER INFORMATION: barcode flanking region

<400> SEQUENCE: 13
cctctacggc tccgtatctt aagacaaatg cgttctcgta ggtttgcttc tacgtgatca    60
tccggggtgg taatccgccc tcgatctcct aaggatgaaa agggttagtt gggccgaatt   120
tagttgatcg ataagctgac ggaaatcttt actagcggat aagctcatcc cttcctgggt   180
caagatgcga gctagtacgg ccgcgtcgct aatctcaatg accattaact ttgcgtagcc   240
atgtgtgctc ctgcggagcg atactattaa ttgcccttc agttctggtt ccattgcact    300
ctgaaggatc tccagtttgt cggaatatca cgtaagaacg cttggcagaa aaagtctcta   360
tgctgtaacg cctcgacgtg aaactcgaca atgtgaattc                         400

<210> SEQ ID NO 14
```

```
<211> LENGTH: 400
<212> TYPE: DNA
<213> ORGANISM: Artificial Sequence
<220> FEATURE:
<223> OTHER INFORMATION: barcode flanking region

<400> SEQUENCE: 14
cgtgaggggc acggcgaggg agatcacaat atactgtcgt cgtttgattt cggaacagag      60
ccaacgggtt cgggtgtctt gtgtgcttca ctacatgacc tcggtaacca gcagatttgg     120
tccaccgggt ttgtgctgga tttaggacaa ggcgaaatat catgatatac acagcatcgc     180
tttgccgtta cattttggc agccaaatgg atcagaggct ggtggggatt acaccacctt      240
gcccttacat tggctaacgt tttcaacacg tgttcctaaa atgtcagtca tgtccccca      300 cacactatag cgctgagtcg atggagatca aatgaggaat cgaccggaaa ccttggtgtc     360
actgcctatg cgccggcaat gaacaaaccg aagtgaattc                           400

<210> SEQ ID NO 15
<211> LENGTH: 400
<212> TYPE: DNA
<213> ORGANISM: Artificial Sequence
<220> FEATURE:
<223> OTHER INFORMATION: barcode flanking region

<400> SEQUENCE: 15
aagctggtag catatggata gctggcatgt tcagataatt gctatctggt atccccacgg      60
atgctgatgg ctgatcttta aggtaaatga cattcgttgt ctttacgcgc cacagtgttg     120
ggccaagcag tctagtcatc cagggtcatg ctgagtctgc ctcgtagctt aaactgttct     180
accattacgc ggtcacgagc cgtgacatct cctatttacc tggcacggtt gcggtggctt     240
gtaccgctcc agatattata ggagtcaagt ctaatgtctt atttatgcga gcgtcatagg     300
accttgtcca ataaattgaa aggatacgcc cgagctgtgg tagctgttag tgacggcata     360
ttgccgaggg agccatcgaa tgcaatgttg attcgaattc                           400

<210> SEQ ID NO 16
<211> LENGTH: 400
<212> TYPE: DNA
<213> ORGANISM: Artificial Sequence
<220> FEATURE:
<223> OTHER INFORMATION: barcode flanking region

<400> SEQUENCE: 16
gtgctgtttt gttcctcagt tcgatacgac ctaggaactg atggcgggct acccggatga      60
tctcgatttg ttctctcatg atagcaacgg cgtcaagcgt cagtcttgtc tcgatggagg     120
gtcgagtaga tttggcttgg atctttctcg tgtaaagtaa atccctgcca gaggaccgag     180
ctggacggcg aagaagtttt tttatctctg cacttcgaac gataagcgtc gtctccctgg     240
tcgcaaacat gggcccaaat tggcttgcga ttgttaaact accggagttt ttaatcgcct     300
aaaccgcgga gttaatccat gcaaccaagc cagtaggatg aagaagtgcg tccagtcgat     360
cgttagtgcc tggaatttct cttatcggca tcaagaattc                           400

<210> SEQ ID NO 17
<211> LENGTH: 400
<212> TYPE: DNA
<213> ORGANISM: Artificial Sequence
<220> FEATURE:
<223> OTHER INFORMATION: barcode flanking region

<400> SEQUENCE: 17
```

```
tgtccgctct ctagcagaag ttgtaagttt taactcagta ggctgctact gagggggattg    60 aacgcatgtt atttgggtta gtggtaataa atgactgtct caggcgccat gctagagaac    120
aattttgctg gtttgcttac atggagacac tagtctggta ccgcaccact catggaatca    180
agcgtggtag gcccattgtt tacgtacgag ccggctgcat gagggcacat agcatctgga    240
taaggcccga gagacagagg tctgccgagt tttacgatac catagctgtt gcgccttgca    300
ttgctatcgg ttttacctgt cgtctccggc agacggttta ttcctcactc aattaattgg    360
ctagtgcggc tggttatcca acaagcgcat tagtgaattc                          400

<210> SEQ ID NO 18
<211> LENGTH: 400
<212> TYPE: DNA
<213> ORGANISM: Artificial Sequence
<220> FEATURE:
<223> OTHER INFORMATION: barcode flanking region

<400> SEQUENCE: 18
ccggtaactt gctcctggga cgcttaaatg gcaattttaa aggaggcgac cgaccccccct   60 aacctaagga tggtacttgg tgaatactat caaccacctc cgtgacggcg gccaattcaa   120
tcctgtaacg cgtgtcgtaa aagttcagtt tgtcgcaggg tcgagttacc cgtaatcctg   180
ggaacgcccc cccaatccgc ttcagggcta tatgccacac ttgaaatcgg aagtatcttg   240
gcttgagtat agtctggcgt ggtaccacac atctacagtg aggtgaaagg cgcttctggc   300
aaggtacgtt ctgcctgaca gaattattcg cattagtgga tgcgtccctg gagtgcgtaa   360
agcacactcg gcagatgagt gctcggagcg gactgaattc                          400

<210> SEQ ID NO 19
<211> LENGTH: 400
<212> TYPE: DNA
<213> ORGANISM: Artificial Sequence
<220> FEATURE:
<223> OTHER INFORMATION: barcode flanking region

<400> SEQUENCE: 19
tagatgttgt acctgacaac cttctccctg caaagcgggt gcctaaagat gttgttacat    60
actccaggcc tcgatatggt ccaatcaaaa tcccatcgga ccagcgttgg aaagtagcac   120
ataagcgtga gacctcagga gatccgtgta taagtgaata ctggcattgg gggtagttac   180
tagtgccgtt caatcgggga atgactcggg acataacgtc tctaatctat atgagggtac   240
catattcacc gtaaaagact agagtccaat ttggcctttc ctcttaggga agagagtaca   300
aaccgaaaac ctggcgatca cgcctgcaca gcagaatctt gcctcgtttg tgtatcattg   360
tggcagagga gcctttaaga catgcgaata gatcgaattc                          400

<210> SEQ ID NO 20
<211> LENGTH: 400
<212> TYPE: DNA
<213> ORGANISM: Artificial Sequence
<220> FEATURE:
<223> OTHER INFORMATION: constant sequence

<400> SEQUENCE: 20
gattttgtcg taaaacgatc atcatgagat caagttcgta gaagccctgt catatttagg    60
agtttgatga tcggcgcgag tgtaagtagc acaccgtatt ccaccgtgtt tacctaacgc   120
gactgcacag tactggcagg taacgtacaa actcatacaa gggtttccac ctctggcatg   180
```

```
cttcttcggt atctcgttcg atgtcgcatt aatgcgttga ggaatggggt tcatctggtc    240
agggtctgac cgtttgtaaa ctaggtgacg agcctgcgga cctgatgttt aatctagcgc    300
cctttatgga aatctgttac gcgcagccag atgtgttgta tcgagggatg tctaggtcct    360
acacgcgacg atgaaacggg ttcgtgtcgg ataggaattc                          400
```

METHODS FOR IDENTIFICATION OF SAMPLES

FIELD OF THE INVENTION

The invention relates to methods for generating a large number of unique transferable molecular identification barcodes and their use in the identification of items, such as in biological samples, and/or their processing. The invention relates to ways of monitoring problems, such as sample switching and cross-contamination of samples, traceability of a sample, providing internal controls for processes.

BACKGROUND OF THE INVENTION

The idea of internal identification of samples through the addition of DNA molecules already dates from a long time. For example, U.S. Pat. No. 5,776,737 describes a method and composition for internal identification of samples.

U.S. Pat. No. 5,776,737 recognizes the power of using mixes of DNA molecules to obtain unique DNA codes in an economical way. For characterization of DNA codes, the Pharmacia ALF automatic sequencer is used which is based on Sanger sequencing.

U.S. Pat. No. 6,030,657 describes a labeling/marking technique which utilizes encapsulated DNA as biomarker, further labeled with infrared (IR) markers, to label products for countering product diversion and product counterfeiting. The actual DNA biomarker sequence was a secondary consideration for security.

EP1488039 recognizes the use of a plurality of different single stranded DNA sequences. Here, DNA barcodes are used as security markers for cash transport boxes. However, the different single stranded types of DNA sequences are not mixed from the onset on during production. Only one type of DNA oligonucleotide is selected from the available different types of oligonucleotides and inserted into the ink reservoir of only one cassette.

US20120115154 discloses a method wherein reference markers comprising one or more oligonucleotides which are not known to be present in a genome are added to biological samples. The reference marker that is added, is a single sequence or a mix of different sequences. The purpose of using mixes of different sequences is, however, for providing an even higher level of specificity and/or security, and thus not for producing a high number of unique reference markers in an economical way.

US20120135413 uses mixtures of oligonucleotides or barcodes in security marking. Here, the purpose of using mixtures is only to allow one to use shorter oligonucleotides to generate a large enough number of unique codes that would be comparable to the number of unique codes than one can obtain when single larger synthetic oligonucleotides are used.

U.S. Pat. No. 6,312,911 uses DNA fragments to encrypt secret messages where every three DNA bases represent either a letter or a symbol. The secret DNA is then concealed in a mixture of concealing DNA. Since the secret DNA code is flanked by primer sequences, it can be specifically called from the complex concealing mixture by amplification and sequencing. The encoded message is then decoded by sequencing the DNA fragment in the security marker and the use of an encryption reference table for decoding.

U.S. Pat. No. 8,785,130 describes the use of nucleotide sequence based codes to monitor methods of detection and identification of genetic material. They make use of different DNA sequences, but they are all positioned on a single larger DNA molecule. That method thus does not have the benefit of using a mixture of DNA sequences for economical production of DNA codes.

WO2014005184 discloses methods of identification or marking using a mixture of different nucleic acids. For characterization, however, they produce a plurality of amplification products with a different size which is the basis for discrimination between the different nucleic acid tag sequences, rather than sequencing.

US20100285985 describes methods and systems for the generation of a plurality of security markers and the detection thereof. Each security marker is a mixture of oligonucleotides that are used as primers on a DNA template. Hence the oligonucleotides are called rtDNA (reverse template DNA) oligonucleotides.

EP2201143 recognizes the power of using a mixture of different DNA molecules, rather than single DNA molecules, as the basis of transferable molecular identification barcodes.

SUMMARY OF THE INVENTION

Entire industries are built around labels comprising diverse products and services. In the retail industry, most products are labeled with 1D (line) or 2D barcode labels, facilitating product stock management and cash desk management in retail companies. In courier delivery services, packages are labelled with barcode labels so that the transport of packages all over the world can be automated and the package location can be even tracked in real-time by customers. Also in testing laboratories, sample tubes to be investigated are labeled with barcode labels.

However, all these items (products, packages, sample tubes, and so on) are labeled at the outside exterior of the item. Once that the item is opened and the content of the item is removed, the link of the barcode with the content of the item is lost. For food items and shipping packages, unpacking the item is usually (almost) the final step in the lifecycle of the item, so that loss of the link with the exterior barcode is not problematic. However, for certain items, such as sample tubes containing a biological sample, the actual processing only starts then.

Here we provide a solution in which both the exterior and the content of an item is labelled with barcodes. The exterior part of the item is labelled with a physical macroscopic barcode label (e.g. optical barcode paper or RFID), while the content of the item is labelled with a transferable molecular identification barcode label. Both the physical and transferable molecular identification barcode labels are unique and have a one to one relation. When either one of the barcode labels is known, the other barcode is also known based on this one to one association. When either one of the barcode labels (e.g. the physical barcode label) is associated with even a third barcode label, the other barcode (in this example the transferable molecular identification barcode label) is also associated with this third barcode label. In contrast to the physical barcode label, the transferable molecular identification barcode label is transferred to the complete downstream processing chain of the content of an item and can be read at the end of the processing and again associated with all other associated barcode labels.

Most processes are prone to errors, especially at moments where there are transfer steps. This also applies to diagnostic tests, which start with the isolation of a biological sample from a patient in a recipient, such as a blood sample in a Vacutainer® tube. The use of printed GS1 barcode labels and barcode scanners can minimize errors, but not always prevent errors. Indeed, some items cannot be labelled with a printed barcode label. For example, when DNA isolated from a biological sample needs to be amplified by a polymerase chain reaction (PCR), the DNA is transferred to a small PCR tube. Printed barcode labels have a size that is too big to be attached to such a small tube and/or can affect the PCR process adversely. Indeed, fixing a paper label to the outside wall of a PCR tube would prevent efficient heat transfer through the wall of a PCR tube, which could affect PCR adversely and even prevent PCR amplification. The PCR tube is then simply labelled with a pencil. But even then, the available place for writing on a PCR tube is limited so that hardly a unique code can be written on the tube. Sometimes the pencil code vanishes from a tube labelled with a pencil during processing. Many labs use standard operating procedures (SOPs) and make use of a LIMS (Laboratory Information Management System). These describe and trace in detail the actions that need to be performed during the different steps of a test, which indeed reduce the chance of errors, but they do not always guarantee that these written actions are correctly executed and that samples are correctly handled and not switched. When samples are switched, a wrong test result is in the end reported to a given patient. Especially in diagnostics these errors cannot be tolerated. Such sample mix-ups sometimes occur in hospitals and laboratories. In a study reporting the findings of non-invasive prenatal tests in blood samples from 18955 pregnant women, 384 blood samples (2%) had a blood-collection or labelling error (Norton et al., (2015) N. Engl. J. Med 372:1589-1597). Since that these samples were not further tested, they could not have resulted in a wrong test result. However, in such cases a new blood sample has to be requested when a test result is still needed, which takes further time and delays the test result, and which in the end may even exceed the time after which actions on the basis of a test result can be taken. If no new blood sample can be requested, no test result can be given at all. But even downstream in the test process, in the lab when testing is actual performed, errors occur. A direct-to-consumer testing company reported a lab mix-up that left up 96 customers reviewing genetic data that was not their own. The mix-up was caused by human error in which a single 96-well plate was incorrectly placed during the processing of the samples (http://blog.23andme.com/23andme-and-you/update-from-23andme/).

Apart from sample switches, a sample, or processed sample derivatives thereof, can be contaminated with another biological sample or processed sample derivatives thereof, which can again result in a wrong test result. For example, when in a genetic test a given sample that is homozygous for a given mutation at a given locus becomes contaminated with a sample that is homozygous, or even heterozygous, for the wild type allele at that given locus, a heterozygous state for the mutation at that given locus could be wrongly concluded and reported. In tests analyzing circulating fetal DNA in maternal blood, the fetal fraction is at least 4%-10%, and it is in this fraction that a DNA anomaly has to be detected against the total DNA background. Even a small contamination of the total sample may thus hamper the test or even result in a wrong test result. The same applies for tests analyzing circulating tumor DNA in blood sample or other biological samples. In a study in which 217 complete genomes were sequenced, 7 samples (3.2%) were found to contain contaminating DNA (Taylor et al., 2015). There is thus also clearly a need for traceability of contaminations or mixing of samples.

Marking and/or tracing items in the fields of commerce and security is also of high interest. For example, many products are marked with a tag that allows the identity or source of the product to be determined. In other circumstances, products are marked with a tag as a means to allow tracking of the product. Such marking and tracing systems may also be used to trace the path and/or timing of an object as it moves from one location to another.

Marking systems can also be used to identify genuine products and distinguish them from counterfeit products, or to identify cases of parallel trading.

There are also circumstances where it may be necessary to identify the source of a product, such as may occur in situations where a substance contaminates another product or environment, such as in the food industry.

In this invention, mixtures of molecules are used for unique internal soluble labelling of items, which allows unequivocal identification of these items, and/or their processing, fulfilling one or more of the following criteria.

In case that mixtures of DNA molecules are used for internal labelling.

A mixture of DNA molecules, rather than a single DNA molecule, is used to allow economical production of unique DNA codes, which are here called transferable molecular identification barcodes. In this way, only a limited number of DNA molecules allow economical production of a large number of unique DNA codes that are preferentially used only once.

Since that such transferable molecular identification barcodes are used for unique identification of items or samples, it is important that they themselves are produced under the most stringent quality conditions. Quality control of a produced transferable molecular identification barcode, or a collector containing such a transferable molecular identification barcode results in destruction of that transferable molecular identification barcode/collector, so that it cannot be used anymore. In case it is still used, it will be in fact used twice, or even more, so that the transferable molecular identification barcode is then not uniquely used. A single unique DNA molecule as a transferable molecular identification barcode does thus not allow quality control after production. When transferable molecular identification barcode mixtures are produced starting from a limited number of DNA molecules, only a few transferable molecular identification barcode tubes should be sacrificed after production for quality control. When the expected sequences are found in these sacrificed transferable molecular identification barcodes, the sequences in the other non-sacrificed transferable molecular identification barcodes can be also concluded to be correct.

Pairs of DNA molecules are used to generate transferable molecular identification barcodes. When mixtures of DNA molecules are used for the production of unique transferable molecular identification barcodes starting from a small number of DNA molecules, some transferable molecular identification barcodes will carry certain DNA molecules in common. Indeed, transferable molecular identification barcodes can share all but one DNA molecule in order to be still a unique mixture. When during processing of a transferable molecular identification barcode, one or more DNA molecules of a mixture fail to be processed and is/are therefore not detected, the transferable molecular identification barcode cannot be discriminated from all the other transferable molecular identification barcodes that share the DNA molecules that were processed. This problem is circumvented by using pairs of DNA molecules, or even triplets of DNA molecules, or more.

Transferable molecular identification barcodes, and possibly together with other target nucleic acids, are processed and characterized by parallel methods, so that a group of DNA never become completely separated or split up during processing. If not, independent transfer steps are initiated next to each other during processing, which are prone to switches, and can therefore result in a wrong characterization of a transferable molecular identification barcode and/or sample when the result of each of the steps initiated next to each other are again combined to a result. If sequencing is used, a parallel sequencing method has to be used.

All DNA molecules in each transferable molecular identification barcode should be sufficiently different in sequence. Indeed, when highly parallel sequencing methods are used, sequencing errors that vary from 1-15% at the single read level. If a mixture contains two or more DNA molecules that differ by only one nucleotide, an amplification and/or sequencing error would wrongly type a transferable molecular identification barcode for another transferable molecular identification barcode.

One aspect of the invention relates to methods of identifying the identity of a plurality of nucleic acid comprising biological samples, comprising the steps of:

providing a plurality of carriers each containing a nucleic acid comprising biological sample, wherein each carrier contains at least 2 nucleic acids for labelling said carrier wherein each of the at least nucleic acid comprises a different nucleotide barcode sequence with a length of at least 4 nucleotides, wherein the combination of these different nucleotide barcode sequences generates a transferable molecular identification barcode, whereby each transferable molecular identification barcode is different for each of the carriers in the collection, characterized in that the nucleotide barcode sequence is flanked at one or both sides by one or more nucleotide barcode sequence identifier sequences allowing the identification of said nucleotide barcode sequence, and wherein each carrier contains a barcode label corresponding to the transferable molecular identification barcode applied on said carrier.

sequencing one or more target sequences in the nucleic acid sequence of the sample and sequencing parts of the nucleic acids comprising the nucleotide barcode sequences, determining the transferable molecular identification barcode of each carrier from the sequenced nucleotide barcode sequences in the nucleic acids, comprising a step of selecting within the sequence data those sequences which contain a nucleotide barcode sequence, wherein the selecting step comprises the identification of the presence of sequences of a predefined length comprising the nucleotide barcode sequence, based on constant sequences flanking the nucleotide barcode sequence at a defined distance, and determining the nucleotide barcode sequences within the selected sequence data, comparing the determined transferable molecular identification barcode with the barcode label provided with the carrier, thereby identifying the identity of the sample.

In embodiments thereof the sample comprising the nucleic acid comprises circulating DNA, such as fetal or tumor DNA.

Embodiments of the methods comprise the step of ligating adaptors to the target sequences in the sample or fragments thereof and to the nucleic acids comprising the nucleotide barcode sequence, and comprising the step of sequencing the target sequences and the nucleotide barcode sequences using the ligated adaptors as sequencing templates.

Embodiments of the methods comprise the step of performing an enrichment step of a target sequence in said nucleic acid sample, and performing an enrichment step of the barcode sequence.

The methods of the present encompass multiplex assays.

Embodiments of the methods comprise the step of attaching to the target sequence of a sample a sample specific tag, optionally also attaching the same sample specific tag to the nucleic acids comprising a nucleotide barcode sequence in said sample added.

In embodiments of the methods, the sequencing of enriched nucleotide barcode sequence and enriched target sequence is performed by a parallel sequencing method.

In embodiments of the methods, the parallel sequencing method is preceded by pooling enriched nucleotide barcode sequences and enriched target sequences from different samples.

In embodiments of the methods, a further different set of nucleotide barcode sequences, defining a further different transferable molecular identification barcode is added to the polynucleotide sample at a later step of the method.

In embodiments of the methods, oligonucleotides for the enrichment of target sequences are in excess to the transferable molecular identification barcodes oligonucleotides for the enrichment for the amplification of barcode or In embodiments of the methods the transferable molecular identification barcodes oligonucleotides for the enrichment for the amplification of barcode are in excess to oligonucleotides for the enrichment of target sequences.

In embodiments of the methods, the nucleic acids comprising the nucleotide barcode sequences have a length similar to the target DNA to be sequenced.

In embodiments of the methods, the nucleotide barcode sequences in a carrier are unknown to the user of the carrier prior to their sequencing, and wherein the step of comparing the determined transferable molecular identification barcode with the barcode label provided is performed by consulting a database containing the relation between transferable molecular identification barcode with the barcode label.

Another aspect of the invention relates to a collection of carriers comprising nucleic acids for labelling at item, wherein each carrier contains at least 2 nucleic acids for labelling wherein each nucleic acid comprises a different nucleotide barcode sequence with a length of at least 4 nucleotides, wherein the combination of these different nucleotide barcode sequences generates a transferable molecular identification barcode, whereby each transferable molecular identification barcode is different for each of the carriers in the collection, characterized in that the nucleotide barcode sequence is flanked at one or both sides by one or more nucleotide barcode sequence identifier sequences allowing the identification of said nucleotide barcode sequence, and wherein each carrier contains a barcode label corresponding to the transferable molecular identification barcode applied on said carrier.

In certain embodiments the collection of carriers is suitable for the application of a biological sample, such as a DNA containing sample, on or in said carrier.

In embodiments thereof the carrier contains one or more of a stabilization agent, preservative, detergent, neutralizing agent, nuclease inhibiting agent, reducing agent, or quenching agent.

In certain embodiments each carrier contains at least 3 of said nucleic acids.

In certain embodiments the nucleotide barcode sequence is flanked by an oligonucleotide sequence for enriching the nucleotide barcode sequence by capturing or amplification.

In certain embodiments the oligonucleotide sequence for enriching the nucleotide barcode sequence is for a method selected from the group consisting of 1-step PCR such as primer extension followed by ligation or a 2-step PCR such as primer extension followed by PCR, circularisation based amplification and nanopore sequencing.

In certain embodiments, the nucleotide barcode sequence is flanked at one or both sides by one or more oligonucleotide binding sequences allowing hybridization based sequence capture of one or both oligonucleotide binding sequences in the nucleotide barcode sequence.

In certain embodiments the nucleotide barcode sequence is flanked by primer binding sequences for PCR primers allowing the amplification and sequencing of said barcode.

In certain embodiments the nucleotide barcode sequence is flanked by primer binding sequences for sequencing said barcode.

In certain embodiments the nucleic acids comprising a barcode sequence are comprised in fragments of a cloning vector, for example obtained by fragmentation or digestion of said vector.

In typical embodiments the carrier is a container for receiving a biological sample.

In typical embodiments the carrier is a substrate for applying and/or immobilizing a biological sample.

Collections of carriers as described above comprise from 100 to 1 million carriers, to 10 million carriers, to 100 million carriers, to more than 100 million carriers.

Another aspect relates to methods of preparing a collection of carriers comprising transferable molecular identification barcodes, comprising the steps of:
a) providing a first collection of different nucleic acids, comprising a nucleotide barcode sequence with a length of at least 4 nucleotides which barcode sequence differs in between the nucleic acids in said collection and with one or more nucleotide barcode sequence identifier sequences allowing the identification of the presence of a nucleotide barcode sequence in a nucleic acid,
b) adding to each carrier a combination of at least 2 of the nucleic acids of step a) to obtain a collection of carriers each having a unique transferable molecular identification barcode defined by the difference in nucleotide barcode sequences,
c) labelling each carrier with a label corresponding to the transferable molecular identification barcode defined by the different nucleotide barcode sequences,
d) storing the relation between the label and the sequences of the nucleotide barcode sequences in the transferable molecular identification barcode.

In embodiments of these methods labelling in step c) and storing in step d) is performed such that a subsequent user of the carrier cannot deduce the relation between the label and transferable molecular identification barcode until the different nucleotide barcode sequences have been determined.

In embodiments of these methods a second collection of nucleic acids is made prior to step b), by defining multiples of nucleic acids with different nucleotide barcode sequences, and wherein in step b) a unique combination of at least 3 multiples of nucleic acids is added to each carrier.

In embodiments of these methods the second collection is prepared by adding the nucleic acids of a multiple together.

In embodiments of these methods the multiple is a pair of two nucleic acids.

Another aspect of the invention relates to methods of preparing a collection of hosts with a vector comprising a transferable molecular identification barcode, comprising the steps of:
a) providing a first collection of nucleic acid vectors in a host, wherein the vector comprises a nucleotide barcode sequence with a length of at least 4 nucleotides which differs in between nucleic acid vectors in the collection, and comprises at one or both sides of the nucleotide barcode sequence one or more nucleotide barcode sequence identifier sequences allowing the identification of said barcode,
b) providing individual colonies of the host and sequencing the barcode in the nucleic acid vector for a plurality of colonies to obtain a second collection of isolated colonies, wherein each colony comprise a nucleic acid vector which has a different nucleotide barcode sequence.

Another aspect of the invention relates to methods of preparing a collection of carriers comprising transferable molecular identification barcodes, the method comprising steps of:
a) providing a collection of hosts as defined in the previous claims,
b) for a selection of colonies isolating the vector from the colonies,
c) adding to each carrier in the collection of carriers a combination of at least 2 nucleic acid vectors with different nucleotide barcode sequences of step b) to obtain a collection of carriers each having a unique transferable molecular identification barcode defined by the difference in nucleotide barcode sequences in between the carriers,
d) labelling each carrier with a label corresponding to the transferable molecular identification barcode defined by different nucleotide barcode sequences,
e) storing the relation between the label and the sequences of the nucleotide barcode sequences in the transferable molecular identification barcode.

In embodiments of these methods, after step c) the vectors are fragmented by a restriction enzyme.

In embodiments of these methods labelling in step d) and storing in step e) is performed such that a subsequent user of the carrier can not deduce the relation between the label and transferable molecular identification barcode until the different nucleotide barcode sequences have been determined.

In embodiments of these methods, prior to step c) a further collection of vectors is prepared from the collection of step b) by defining multiples of isolated nucleic acid vectors wherein in the multiple each vector has a different nucleotide barcode sequence.

The present invention further comprises the following statements:
1. A method of identifying the identity of a plurality of nucleic acid comprising biological samples, the method comprising the steps of:
   providing a plurality of carriers, being substrates or containers, each containing a nucleic acid comprising biological sample, wherein each carrier comprises, in addition to the nucleic acid comprising sample, at least 2 nucleotide barcode nucleic acids for labelling said carrier wherein each of these at least 2 nucleotide barcode nucleic acids comprises a different minimal nucleotide barcode sequence with a length of at least 4 nucleotides, wherein the combination of these different nucleotide barcode nucleic acids generates a transferable molecular identification barcode, whereby each transferable molecular identification barcode is different for each of the carriers, characterised in that the minimal nucleotide barcode sequences in said at least 2 nucleotide barcode nucleic acids is flanked at one or both sides by non-viral and non-bacterial nucleotide barcode sequence identifier sequences which are identical in all nucleotide barcode nucleic acids, and flanked at one or both sides by non-viral and non-bacterial extracting sequences which are identical in all nucleotide barcode nucleic acids, allowing the identification of said minimal nucleotide barcode sequences, and wherein each carrier contains a macroscopic barcode label corresponding to the transferable molecular identification barcode applied on said carrier, sequencing one or more target sequences in the nucleic acid of the biological sample and sequencing of target sequences in the nucleotide barcode nucleic acids comprising the minimal nucleotide barcode sequences, wherein the sequencing of the target sequences in the nucleic acid of the biological sample and sequencing of target sequences of the nucleotide barcode nucleic acids comprising the minimal nucleotide barcode sequences is performed by a parallel sequencing method, wherein the parallel sequencing method is optionally preceded by pooling target sequences in the nucleic acid of the biological sample and target sequences of the nucleotide barcode nucleic acids comprising the minimal nucleotide barcode sequences from different samples, determining and selecting from the obtained sequence data the sequences derived from nucleotide barcode nucleic acids, comprising a step of selecting from the obtained sequence data those sequences derived from nucleotide barcode nucleic acids, wherein the selecting step comprises the identification of sequences having one or more nucleotide barcode sequence identifier sequences adjacent to the minimal nucleotide barcode sequence;

determining and selecting the minimal nucleotide barcode sequences within the isolated sequences that have a nucleotide barcode sequence identifier sequence, comprising a step of selecting the sequence present between two extracting sequences at a defined length, or selecting the sequence present adjacent to one extracting sequence at a defined length, and determining these selected sequences as minimal nucleotide barcode sequences, comparing the determined minimal nucleotide barcode sequences with the expected minimal nucleotide barcode sequences based on the macroscopic barcode label provided with the carrier, thereby identifying the identity of the sample and/or a contamination.

2. The method according to statement 1, comprising the step of ligating adaptors to the target nucleic acids in the sample and to the nucleic acids comprising the nucleotide barcode sequences, and comprising the step of sequencing the target sequences and the nucleotide barcode sequences using the ligated products as sequencing templates.

3. The method according to statement 1 or 2, comprising the step of performing an enrichment step of a target sequence in said nucleic acid sample, and performing an enrichment step of the nucleotide barcode sequences.

4. The method according to any one of statements 1 to 3, comprising the step of attaching to the target sequence of a sample a sample specific pooling barcode, optionally also attaching the same sample pooling barcode to the nucleic acids comprising the nucleotide barcode sequences in said sample.

5. The method according to any one of statements 1 to 4, wherein the nucleotide barcode sequences have a length similar to the target nucleic acid or enriched target nucleotide sequences to be sequenced.

6. The method according to any one of statements 1 to 5, which is a method comprising a step of collecting a sample and a step of isolating nucleic acids from said sample, wherein a first set of at least 2 nucleotide barcode nucleic acids for labelling are added to the collected sample, and wherein a second set of at least 2 nucleotide barcode nucleic acids for labelling are added to the isolated nucleic acids.

7. A collection of carriers, being substrates or containers, comprising nucleic acids for labelling an item, wherein each carrier comprises at least 2 nucleotide barcode nucleic acids, other than sample nucleic acid, for labelling, wherein each nucleotide barcode nucleic acid comprises a different minimal nucleotide barcode sequence with a length of at least 4 nucleotides, where at least two of said different nucleotide barcode nucleic acids have a minimal nucleotide barcode sequence of the same length, wherein the combination of these different nucleotide barcode nucleic acids generates a transferable molecular identification barcode, whereby each such transferable molecular identification barcode is different for each of the carriers in the collection, characterised in that the minimal nucleotide barcode sequences in said at least 2 nucleotide barcode nucleic acids is flanked at one or both sides non-viral and non-bacterial nucleotide barcode sequence identifier sequences which are identical in all nucleotide barcode nucleic acids, and/or flanked at one or both sides by non-viral and non-bacterial extracting sequences which are identical in all nucleotide barcode nucleic acids, allowing the identification of said nucleotide barcode sequence, and wherein each carrier contains a macroscopic barcode label corresponding to the transferable molecular identification barcode applied to said carrier.

8. The collection according to statement 7, wherein said nucleotide barcode nucleic acids for labelling do not comprise sequences for transcribing nucleic acid into RNA.

9. The collection of carriers according to statement 7 or 8, wherein the carrier is suitable for the application of a biological sample on or in said carrier.

10. The collection of carriers according to any one of statements 7 to 9, wherein said sample is a DNA containing sample.

11. The collection of carriers according to any one of statements 7 to 9, wherein said sample is a RNA containing sample.

12. The collection of carriers according to any one of statements 7 to 11, wherein the minimal nucleotide barcode sequence is flanked by oligonucleotide sequences for enriching the minimal nucleotide barcode sequence by amplification, or wherein the minimal nucleotide barcode sequence is flanked at one or both sides by one or more oligonucleotide binding sequences allowing hybridization based sequence capture at one or both oligonucleotide binding sequences in the nucleotide barcode sequence.

13. The collection according to statement 12, wherein the minimal nucleotide barcode sequences in said at least 2 nucleotide barcode nucleic acids is flanked at one or both sides by non-viral and non-bacterial nucleotide barcode sequence identifier sequences which are identical in all nucleotide barcode nucleic acids, and/or flanked at one or both sides by non-viral and non-bacterial extracting sequences which are identical in all nucleotide barcode nucleic acids, 14. The collection of carriers according to any one of statements 7 to 13, wherein the amplification is selected from the group consisting of 1-step PCR, 2-step PCR, primer extension followed by ligation and PCR, circularisation based amplification and nanopore sequencing, 15. The collection of carriers according to any one of statements 7 to 14, wherein the minimal nucleotide barcode sequence is flanked by primer binding sequences for PCR primers allowing the amplification and sequencing of said minimal nucleotide barcode sequence and optionally allowing the amplification and sequencing of nucleotide barcode sequence identifier and extracting sequences.

16. The collection of carriers according to any one of statements 7 to 15, wherein the nucleotide barcode nucleic acids are comprised in fragments of a cloning vector.

17. The collection of carriers according to any one of statements 7 to 16, wherein the nucleotide barcode nucleic acids are fragments obtained by fragmentation or digestion of said vector.

18. The collection of carriers according to statement 16 or 17, wherein said vector or vector fragment comprises a sequence selected from the group consisting of SEQ ID NO:1 to SEQ ID NO:20.

19. The collection of carriers according to statement 16 or 17, wherein said vector or vector fragment comprises the sequence of SEQ ID NO:1 and SEQ ID NO:11.

20. The collection of carriers according to any one of statements 7 to 19, further comprising one or more primers, for capturing a nucleic acid comprising said nucleotide barcode sequence.

21. The collection of carriers according to any one of statements 7 to 20, further comprising one or more primers, for amplifying a nucleic acid comprising said nucleotide barcode sequence.

22. A method of preparing a collection of carriers, being substrates or containers, comprising transferable molecular identification barcodes, the method comprising the steps of:
 a) providing a first collection of different nucleotide barcode nucleic acids, comprising a minimal nucleotide barcode sequence of at least 4 nucleotides, wherein at least two of said different nucleotide barcode nucleic acids have a minimal nucleotide barcode sequence of the same length, of which the minimal nucleotide barcode sequence differs in between the nucleotide barcode nucleic acids in said collection and with one or more non-viral and non-bacterial nucleotide barcode sequence identifier sequences and/or one or more non-viral and non-bacterial extracting sequences allowing the identification of the minimal nucleotide barcode sequence in a nucleotide barcode nucleic acid,
 b) adding to each carrier a combination of at least 2 of the nucleotide barcode nucleic acids of step a) to obtain a collection of carriers each having a unique transferable molecular identification barcode defined by the difference in the mix of minimal nucleotide barcode sequences,
 c) labelling each carrier with a macroscopic barcode label corresponding to the transferable molecular identification barcode defined by the different mix of minimal nucleotide barcode sequences,
 d) storing the relation between the macroscopic label and the mix of minimal nucleotide barcode sequences in the transferable molecular identification barcode.

23. The method according to statement 22, wherein the minimal nucleotide barcode sequences in said at least 2 nucleotide barcode nucleic acids is flanked at one or both sides by non-viral and non-bacterial nucleotide barcode sequence identifier sequences which are identical in all nucleotide barcode nucleic acids, and/or flanked at one or both sides by non-viral and non-bacterial extracting sequences which are identical in all nucleotide barcode nucleic acids.

24. The method according to statement 22 or 23, wherein said first collection of different nucleic acids do not comprise sequences for transcribing nucleic acid into RNA.

25. The method according to any one of statements 22 to 24, wherein nucleotide barcode nucleic acids comprises a sequence selected from the group consisting of SEQ ID NO:1 to SEQ ID NO:20.

26. The method according to any one of statements 22 to 25, wherein said nucleotide barcode nucleic acids comprises the sequence of SEQ ID NO:1 and SEQ ID NO:11.

27. The method according to any one of statements 22 to 26, wherein labelling in step c) and storing in step d) is performed such that a subsequent user of the carrier cannot deduce the relation between the macroscopic barcode label and transferable molecular identification barcode until the different nucleotide barcode sequences have been determined.

28. A method of preparing a collection of hosts with a vector comprising a nucleotide barcode sequence, the method comprising the steps of:
 a) providing a first collection of nucleic acid vectors in a host, wherein the vector comprises a nucleotide barcode sequence with a minimal nucleotide barcode sequence with a length of at least 4 nucleotides which differs in between nucleotide barcode nucleic acid vectors in the collection, wherein at least two of said different nucleotide barcode sequences have a minimal nucleotide barcode sequence of the same length, and comprises at one or both sides of the minimal nucleotide barcode sequences one or more non-viral and non-bacterial nucleotide barcode sequence identifier sequences and/or one or more non-viral and non-bacterial extracting sequences allowing the identification of said minimal nucleotide barcode sequence,
 b) providing individual colonies of the host and sequencing the nucleotide barcode sequences in the nucleic acid vector for a plurality of colonies to obtain a second collection of isolated colonies, wherein each colony comprise a nucleic acid vector which has a different nucleotide barcode sequence.

29. The method according to statement 28, wherein said nucleic acids vectors do not comprise sequences for transcribing nucleic acid into RNA.

30. The method according to statement 28 or 29, wherein said vector comprises a sequence selected from the group consisting of SEQ ID NO:1 to SEQ ID NO:20.

31. The method according to statement 28 or 29, wherein said vector comprises the sequence of SEQ ID NO:1 and SEQ ID NO:11.

32. A method of preparing a collection of carriers, being substrates or containers, comprising transferable molecular identification barcodes, the method comprising the steps of:
   a) providing a collection of hosts as defined in statement 28,
   b) for a selection of colonies isolating the vector from the colonies,
   c) adding to each carrier in the collection of carriers a combination of at least 2 nucleic acid vectors with different nucleotide barcode sequences, wherein at least two of said nucleic acid vectors have a minimal nucleotide barcode sequence of the same length of step b) to obtain a collection of carriers each having a unique transferable molecular identification barcode defined by the difference in mix of minimal nucleotide barcode sequences in between the carriers, and optionally fragmenting the vectors by a restriction enzyme,
   d) labelling each carrier with a macroscopic barcode label corresponding to the transferable molecular identification barcode defined by the mix of different minimal nucleotide barcode sequences,
   e) storing the relation between the macroscopic barcode label and the sequences of the minimal nucleotide barcode sequences in the transferable molecular identification barcode.

33. A method of tracing nucleotide barcode nucleic acids in a set of carriers method comprising the steps of:
   providing a plurality of carriers, free from genomic DNA or RNA, comprising at least 2 nucleotide barcode nucleic acids for labelling said carrier wherein each of these at least 2 nucleotide barcode nucleic acids comprises a different minimal nucleotide barcode sequence with a length of at least 4 nucleotides, wherein the combination of these different nucleotide barcode nucleic acids generates a transferable molecular identification barcode, whereby each transferable molecular identification barcode is different for each of the carriers, characterised in that the minimal nucleotide barcode sequences in said at least 2 nucleotide barcode nucleic acids is flanked at one or both sides by non-viral and non-bacterial nucleotide barcode sequence identifier sequences which are identical in all nucleotide barcode nucleic acids, and flanked at one or both sides by non-viral and non-bacterial extracting sequences which are identical in all nucleotide barcode nucleic acids, allowing the identification of said minimal nucleotide barcode sequences, and
   wherein each carrier contains a macroscopic barcode label corresponding to the transferable molecular identification barcode applied on said carrier,
      sequencing target sequences in the nucleotide barcode nucleic acids comprising the minimal nucleotide barcode sequences, by a parallel sequencing method, wherein the parallel sequencing method is optionally preceded by pooling target sequences of the nucleotide barcode nucleic acids comprising the minimal nucleotide barcode sequences,
      determining and selecting from the obtained sequence data the sequences derived from nucleotide barcode nucleic acids, comprising a step of selecting from the obtained sequence data those sequences derived from nucleotide barcode nucleic acids, wherein the selecting step comprises the identification of sequences having one or more nucleotide barcode sequence identifier sequences adjacent to the minimal nucleotide barcode sequence;
      determining and selecting the minimal nucleotide barcode sequences within the isolated sequences that have a nucleotide barcode sequence identifier sequence, comprising a step of selecting the sequence present between two extracting sequences at a defined length, or selecting the sequence present adjacent to one extracting sequence at a defined length, and determining these selected sequences as minimal nucleotide barcode sequences,
      comparing the determined minimal nucleotide barcode sequences with the expected minimal nucleotide barcode sequences based on the macroscopic barcode label provided with the carrier.

34. A method of identifying the identity of a plurality of nucleic acid comprising biological samples, the method comprising the steps of:
   providing a plurality of carriers, being substrates or containers, each containing a nucleic acid comprising biological sample,
   wherein each carrier comprises, in addition to the nucleic acid comprising sample, at least 2 nucleotide barcode nucleic acids for labelling said carrier wherein each of these at least 2 nucleotide barcode nucleic acids comprises a different minimal nucleotide barcode sequence with a length of at least 4 nucleotides, wherein the combination of these different nucleotide barcode nucleic acids generates a transferable molecular identification barcode, whereby each transferable molecular identification barcode is different for each of the carriers, characterised in that the minimal nucleotide barcode sequences in said at least 2 nucleotide barcode nucleic acids is flanked at one or both sides by non-viral and non-bacterial extracting sequences which are identical in all nucleotide barcode nucleic acids, and
   wherein each carrier contains a macroscopic barcode label corresponding to the transferable molecular identification barcode applied on said carrier,
      sequencing one or more target sequences in the nucleic acid of the biological sample and sequencing of target sequences in the nucleotide barcode nucleic acids comprising the minimal nucleotide barcode sequences, wherein the sequencing of the target sequences in the nucleic acid of the biological sample and sequencing of target sequences of the nucleotide barcode nucleic acids comprising the minimal nucleotide barcode sequences is performed by a parallel sequencing method, wherein the parallel sequencing method is optionally preceded by pooling enriched target sequences in the nucleic acid of the biological sample and target sequences of the nucleotide barcode nucleic acids comprising the minimal nucleotide barcode sequences from different samples,
      determining and selecting from the obtained sequence data the minimal nucleotide barcode sequences, comprising a step of selecting the sequence present between two extracting sequences at a defined length, or selecting the sequence present adjacent to one extracting sequence at a defined length, and determining these selected sequences as minimal nucleotide barcode sequences,
         comparing the determined minimal nucleotide barcode sequences with the expected minimal nucleotide barcode sequences based on the macroscopic barcode label provided with the carrier, thereby identifying the identity of the sample and/or the sample is free of contamination.

DETAILED DESCRIPTION OF THE INVENTION

Brief Description of the Figures

FIG. 3. Examples of single stranded or double stranded nucleotide barcode sequences FIG. 4. Nucleotide barcode plasmids and linearization thereof.

DEFINITIONS

Figure 1:
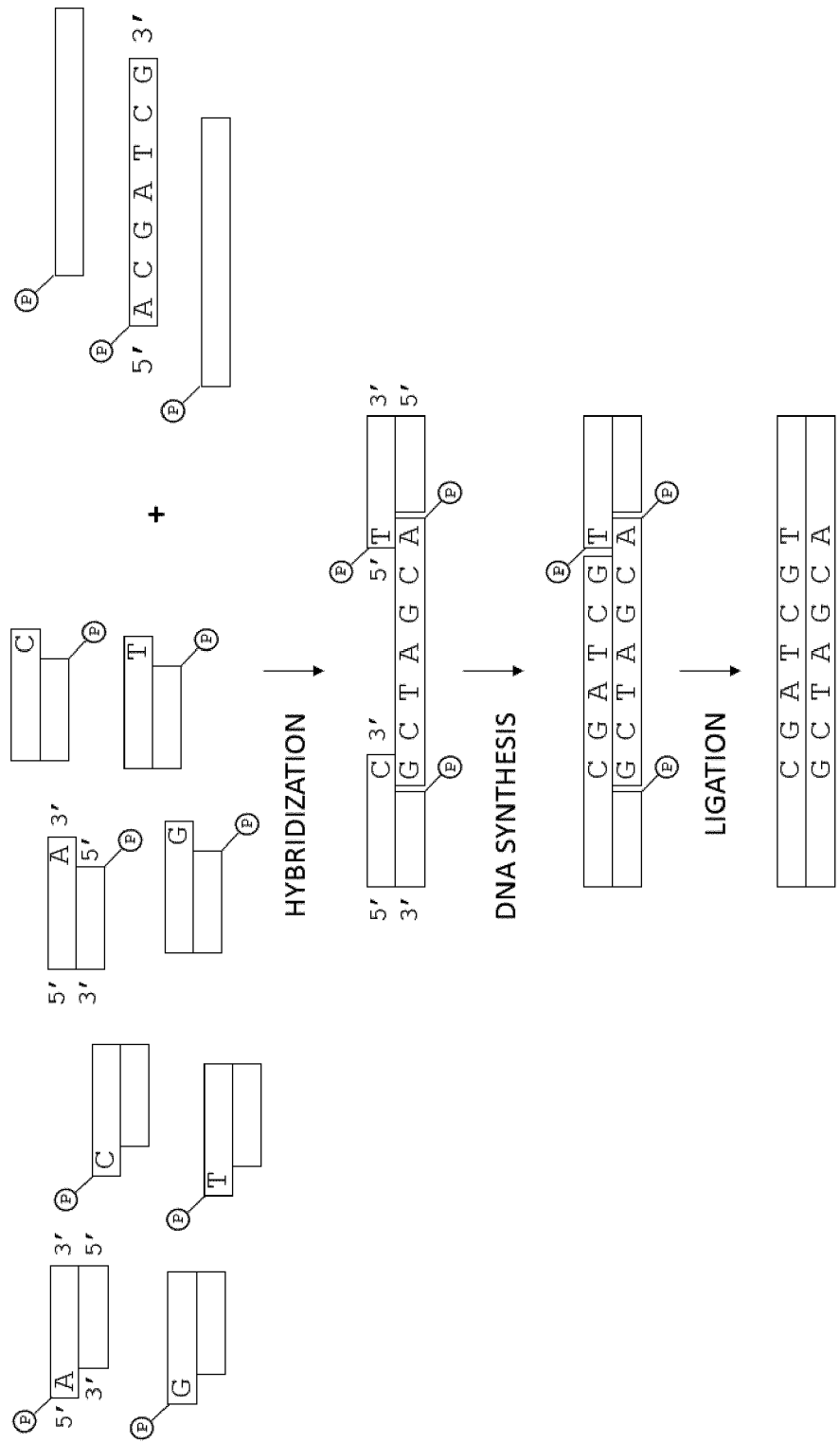
FIG. 1. Preparation of single stranded nucleotide barcode oligonucleotides to be characterized in NGS sequencing.

Terms used in this application, including the specification and claims, are defined as set forth below unless otherwise specified. These terms are defined specifically for clarity, but all the definitions are consistent with how a skilled artisan would understand these terms.

It must be noted that the singular forms "a", "an," and "the" include plural referents unless the context clearly dictates otherwise.

The terms "as used herein", "those defined herein", and "those defined above" when referring to a variable incorporates by reference the broad definition of the variable as well as preferred, more preferred and most preferred definitions, if any.

As used herein the term "nucleic acid" refers to a polymer composed of nucleotides, e.g. deoxyribonucleotides or ribonucleotides. It also includes compounds produced synthetically, but which have a variant sugar-phosphate backbone (polyamide (e.g. peptide nucleic acids (PNAs), linked nucleic acids (LNAs), polymorpholino polymers), and/or a variant of one or more bases, but which can still hybridize with naturally occurring nucleic acids in a sequence specific manner analogous to that of the two naturally occurring nucleic acids, i.e. participate in hybridization reactions, cooperative interactions through Pi electrons stacking and hydrogen bonds, such as Watson-Crick base pairing interactions, Wobble interactions, etc. They may be single stranded or double stranded, or even triplet DNA or more complex structures. The term "nucleic acid" may be a specified nucleic acid or a nucleic acid comprising a nucleotide sequence which is the complement of the nucleic acid, a nucleic acid comprising a nucleotide sequence with greater than 50%, 55%, 60%, 65%, 70%, 75%, 80%, 85%, 90% or 95% sequence identity to the specified nucleic acid, or a nucleic acid comprising a nucleotide sequence with greater than 50%, 55%, 60%, 65%, 70%, 75%, 80%, 85%, 90% or 95% sequence identity to the complement of the specified nucleic acid.

The nucleic acid may be a naturally occurring nucleic acid, a nucleic acid of genomic origin, a mitochondrial nucleic acid, a nucleic acid of cDNA origin (derived from a m RNA), a nucleic acid derived from a bacterium, a virus, a fungus, a nucleic acid of synthetic origin, a non-naturally occurring nucleic acid, an analogue of DNA and/or RNA, and/or a derivative, and/or combination of any of the aforementioned. Nucleic acid modifications can include the addition of chemical groups that incorporate additional charge, polarizability, hydrogen bonding, electrostatic interaction, and functionality to the individual nucleic acid bases or to the nucleic acid as a whole. Such modifications may include a blocking group at the 5' and/or 3' ends, e.g. to improve stability, base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, methylation, and the like. Other types of nucleic acids are contemplated.

The nucleic acid(s) can be derived from a completely chemical synthesis process, such as a solid phase-mediated chemical synthesis, from a biological source, such as through isolation from any species that produces nucleic acid, or from processes that involve the manipulation of nucleic acids by molecular biology tools (such as DNA replication, ligation, PCR amplification, reverse transcription, or from a combination of those processes), or a combination thereof.

Nucleic acid modifications may facilitate isolation and/or detection, either directly or indirectly, by another molecule, to which in turn other molecules may be bound. Such modifications could be one or more biotin groups, which can interact with streptavidin. Other interacting molecules for such purposes could be biotin/avidin, biotin/biotin-binding-molecule (e.g. NEUTRAVIDINT modified avidin (Pierce Chemicals Rockford, IL), glutathione S-transferase(GST)/glutathione, antibody/antigen, antibody/antibody-binding-molecule, dioxigen in/anti-dioxigenin, DNP(2,4-dinitrophe-nyl)/anti-DNP antibodies, maltose-binding-protein/maltose, chelation (e.g. (Co2+, Ni2+)/polyhistidine, pluronic coupling technologies.

As used herein the term "deoxyribonucleic acid" and "DNA" as used herein mean a polymer composed of deoxyribonucleotides.

As used herein the term "ribonucleic acid" and "RNA" as used herein mean a polymer composed of ribonucleotides.

As used herein the term "oligonucleotide" refers to a nucleic acid that is relatively short, generally shorter than 200 nucleotides, more particularly, shorter than 100 nucleotides, most particularly, shorter than 50 nucleotides, but generally greater than 5 nucleotides in length. Typically, oligonucleotides are single-stranded DNA molecules. Such oligonucleotides may carry modifications, such as, for example being biotinylated, 5' phosphorylated. A synonymous term of a 'oligonucleotide' is 'oligo'.

As used herein the term "target nucleic acid" is a nucleic acid or (a) part(s) thereof, or nucleic acid(s) or parts thereof, present in an item, such as a biological sample, that will be characterized. In most instances this part, or parts, of nucleic acid(s) are the target of a characterization process.

As used herein the term "target nucleotide sequence" refers to a molecule that includes the nucleotide sequence of a target nucleic acid, such as, for example, the amplification product obtained by amplifying a target nucleic acid, the sequencing product obtained by sequencing a target nucleic acid, the cDNA produced upon reverse transcription of an RNA target nucleic acid.

As used herein the term "nucleotide barcode" refers to a target nucleic acid having a particular sequence, or part thereof, that is used as barcode or means of identification. Different nucleotide barcodes have different barcode sequences, which are termed as different types of nucleotide barcodes. If the nucleotide barcode is built up of DNA it is termed as a "DNA-type nucleotide barcode", if the nucleotide barcode is built up of RNA it is termed as a "RNA-type nucleotide barcode". The actual barcode sequence, as used herein the term "minimal nucleotide barcode'" might be flanked by constant sequences which are identical in a given type of nucleotide barcodes. These flanking constant sequences are not encoded in any naturally occurring genome, bacterial or viral DNA (and thus not found in cloning vectors, or more specifically cloning vector backbones), or have a sequence that is less than 1%, less than 2%, less than 3%, less than 4%, less than 5%, less than 10%, less than 15%, less than 20%, less than 25%, less than 30%, less than 40%, less than 50% homologous to a sequence encoded in any naturally occurring genome, viral, bacterial DNA.

As used herein the term "transferable molecular identification barcode" refers to a single type of nucleotide barcode, or a mixture of different types of nucleotide barcodes. In transferable molecular identification barcodes build of a mixture of different types of nucleotide barcodes, a transferable molecular identification barcode may carry all, but one, nucleotide barcodes in common with other transferable molecular identification barcodes, in order to be still a unique transferable molecular identification barcode. Synonymous terms of a barcode may be an index, a tag, a MID (molecular identifier). The term 'transferable molecular identification barcode' also refers to one or more nucleotide barcodes that are in an insoluble phase at a given moment, but that become (again) soluble during the processing. If the transferable molecular identification barcode is built up of DNA it is termed as a "DNA-type transferable molecular identification barcode", if the transferable molecular identification barcode is built up of RNA it is termed as a "RNA-type transferable molecular identification barcode".

As used herein the term "macroscopic barcode label' refers to a printed barcode paper label (e.g. an optical 1D (line) or 2D barcode paper label) or an RFID (Radio Frequency Identification Barcodes) barcode label.
used for labeling of an item (e.g. a recipient holder). Such a labelling can be performed by different means, such as attachment of a unique paper barcode at the outside of the wall of a recipient holder. When the recipient holder contains a unique transferable molecular identification barcode, a unique macroscopic barcode label can be unequivocally associated and linked to the corresponding transferable molecular identification barcode.

As used herein the term "complementary" refers to the capacity for precise pairing between two nucleotides. If a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. The degree of complementarity between nucleic acid strands has significant effects on the efficiency and strength of hybridization between nucleic acid strands.

As used herein the term "specific hybridization" refers to the binding of a nucleic acid to a target nucleic acid or target nucleotide sequence in the absence of substantial binding to other nucleic acids or nucleotide sequences present in the hybridization mixture under defined stringency conditions. A person skilled in the art recognizes that relaxing the stringency of the hybridization conditions allows sequence mismatches to be tolerated. Hybridizations are carried out under stringent hybridization conditions. The phrase "stringent hybridization conditions" generally refers to a temperature in a range from about 5° C. to about 20° C. or 25° C. below the melting temperature ($T_m$) for a specific sequence at a defined ionic strength and pH. As used herein, the $T_m$ is the temperature at which a population of double-stranded nucleic acid molecules becomes half-dissociated into single strands. Methods for calculating the $T_m$ of nucleic acids are well known in the art (A Laboratory Manual, by Sambrook and Russel, 3rd Edition, Cold Spring Harbor Laboratory Press, 2001). The melting temperature of a hybrid (and thus the conditions for stringent hybridization) is affected by various factors such as the length and nature (DNA, RNA, base composition) of the primer or probe and nature of the target nucleic acid (DNA, RNA, base composition), present in solution or immobilized, and the like, as well as the concentration of salts and other components (e.g., the presence or absence of formamide, dextran sulfate, polyethylene glycol).

As used herein the term "primer" refers to an oligonucleotide that is capable of hybridizing (also termed "annealing") with a nucleic acid and serving as an initiation site for nucleotide (DNA or RNA) polymerization under appropriate conditions (i.e., in the presence of four different nucleoside triphosphates and an agent for polymerization, such as DNA or RNA polymerase or reverse transcriptase) in an appropriate buffer and at a suitable temperature.

As used herein the term "primer binding site" or "primer site" refers to the segment of the target nucleic acid or target nucleotide sequence to which a primer hybridizes from which it primes nucleotide synthesis. A primer binding site in the transferable molecular identification barcodes is not encoded in any naturally occurring genome, bacterial or viral DNA (and thus not found in cloning vectors, or more specifically cloning vector backbones), or have a sequence that is less than 1%, less than 2%, less than 3%, less than 4%, less than 5%, less than 10%, less than 15%, less than 20%, less than 25%, less than 30%, less than 40%, less than 50% homologous to a sequence encoded in any naturally occurring genome, viral, bacterial DNA. The segment of the target nucleic acid or target nucleotide sequence to which the primer binds might here also be called as an oligonucleotide binding sequence. The primer binding site is typically at least 5 nucleotides long and, more typically range from 10 to 30 nucleotides, or even more. Shorter primer binding sites generally require cooler temperatures to form sufficiently stable hybrid complexes between primer and the template. A primer needs not reflect the exact sequence of the template but must be sufficiently complementary to hybridize with a template. A primer is said to anneal to another nucleic acid if the primer, or a portion thereof, hybridizes to a nucleotide sequence within the nucleic acid. The statement that a primer hybridizes to a particular nucleotide sequence is not intended to imply that the primer hybridizes either completely or exclusively to that nucleotide sequence.

As used herein the term "primer pair" refers to a set of primers including a 5' "upstream primer" that hybridizes with the complement of the 5' end of the DNA sequence to be amplified and a 3' "downstream primer" that hybridizes with the 3' end of the sequence to be amplified. Primers that hybridize to nucleotide barcode sequences have a sequence not encoded in any naturally occurring genome, bacterial or viral DNA (and thus not found in cloning vectors, or more specifically cloning vector backbones), or have a sequence that is less than 1%, less than 2%, less than 3%, less than 4%, less than 5%, less than 10%, less than 15%, less than 20%, less than 25%, less than 30%, less than 40%, less than 50% homologous to a sequence encoded in any naturally occurring genome, viral, bacterial DNA.

As will be recognized by a person skilled in the art, the terms "upstream" and "downstream" are not intended to be limiting, but rather provide illustrative orientations. Synonymous terms are forward and reverse primers, left and right primers, + (plus) and − (minus) primers, 5' and 3' primers. A "primer pair" in which one primer has a primer binding site in the plus DNA strand and the second primer has a primer binding site in the minus DNA strand of a target nucleic acid, can prime a PCR reaction. A "primer pair" may also refer to a pair of primers in which both primers have a primer binding site in the same DNA strand (plus or minus DNA strand) of a target nucleic acid, such as primer pairs used in a ligation chain reaction assay or primer-extension-ligation assays.

Primers are selected so that the majority of the amplicons detected after amplification have the "expected length" in the sense that they result from priming at the expected sites at each end of the target nucleic acid, as opposed to amplicons resulting from priming within the target nucleic acid, which produce amplicons with a different length than the expected length. In various embodiments, primers are selected to that at least 50%, at least 55%, at least 60%, at least 65%, at least 70%, at least 75%, at least 80%, at least 85%, at least 90%, at least 95%, at least 96%, at least 97%, at least 98%, or at least 99% of the obtained amplicons have the expected length.

As used herein the term "adapter" refers to a predetermined nucleotide sequence having one or more predetermined functions that is added to a target nucleotide sequence, and may thus even become part of the target nucleotide sequence. An adapter can be added at one end, or at both ends of a target nucleic acid or target nucleotide sequence. When adapters or added at both ends, they can be identical or different with respect to sequence. A target nucleotide sequence that is flanked by adapters at both sites can have either a linear or circularized form. An added adapter can have one or more specific type of predetermined functions. As used herein the term "adapter" therefore can refer to one adapter or multiple adapters. When more than one function is included, the functions can be of the same type or of different type(s). Different types of adapters can be incorporated at any position in an overall adapter. Synonymous terms of adapter are, for example, nucleotide adapter, universal adapter, tag, nucleotide tag, universal tag.

Examples of predetermined adapters or types of adapter functions, but not limited to, might be a primer sequence, priming binding or annealing site for DNA synthesis, a priming binding or annealing site for sequencing, a hybridization site for an oligonucleotide, a recognition site for one or more restriction enzymes, a barcode sequence, an immobilization sequence, a leader-adapter for a motor protein for nanopore sequencing (Oxford Nanopore Technologies), or other recognition or binding sequences useful for subsequent processing, a linker or spacer function linking one or more adapters described above. Further, as used herein, the reference to specific adapter sequences also refer to the complements to any such sequences, such that upon complementary replication the specific described sequence will be obtained.

When different adapters are present in an overall adapter, the nucleotide sequence units that build such different adapters can be positioned as non-overlapping different neighboring sequence units and/or as overlapping sequence units. For example, a 20 nucleotide long adapter function that will be used as a primer binding site for a DNA synthesis reaction, and a 20 nucleotide long adapter function used for capturing/isolation of a given target nucleotide sequence, may be overlapping and have e.g. a 10 nucleotide sequence in common so that the combined sequence of both adapters is 30 nucleotides long instead of 40 nucleotides.

As used herein the term 'ligation adapter' refers to completely or partly double stranded DNA molecules. In general, they are used for their ligation to other DNA molecules. They are mostly prepared from a mixture of two, possibly partial, complementary hybridizing oligonucleotides. Partly double stranded ligation adapters can have hairpin adapters. A function of a hairpin adapter is to prevent that DNA molecules after ligation do not hybridize at their 5' end, for example to prevent concatenation. Another hairpin function is the hairpin-adapter to which the hairpin-protein binds to facilitate nanopore sequencing (Oxford Nanopore Technologies), A ligation adapter can also be produced from a single stem-loop oligonucleotide comprising an inverted repeat and a loop as described in patent U.S. Pat. No. 7,803,550. All these ligation adapters might have 1 or more non-complementary nucleotides at the actual ligation site, which might facilitate and/or allow directional ligation. For example, a ligation adapter might have a 3' T overhang that can hybridize with a 3' A-overhang of a double stranded target nucleotide sequence to facilitate ligation.

As used herein the term 'pooling barcodes' refer to barcodes that mark target nucleotide sequences for more efficient (less time-consuming) and/or economical pooling of different processed DNA samples. Mostly they are present in a ligation adapter or a primer used for DNA synthesis or amplification. A pooling barcode adds thus an adapter function to target nucleotide sequences which then encode information about the target nucleotide sequences that were produced. For example, a different pooling barcode (with a different barcode sequence) can be used to amplify one or more target nucleic acids from each of a number of different samples from different individuals. For example, a different pooling barcode (with a different barcode sequence) can be used to amplify one or more target nucleic acids from each of a number of different individual cells from a biological sample. The pooling barcode nucleotide sequence thus respectively indicates the sample or cell origin of the resulting target nucleotide sequences. This allows combining of the different types of pooling-barcoded target nucleotide sequences from the different samples in downstream processes. This simplifies the total number of workflows for each sample to one single workflow for all pooled samples once that pooling has been performed. One application would be sequencing of the different target nucleotide sequences by highly parallel sequencing. The sequencing output of highly parallel sequencing methods and apparatuses is enormous, and for many applications too high for single samples. The full capacity of a highly parallel sequencing apparatus can be used in the most economical way by combining different pooling-barcoded target nucleotide sequences from different samples/individuals. After sequencing, the different sequences obtained from the target nucleotide sequences can be grouped according to the pooling-barcode sequence that is present, and therefore assigned to the original samples, and again further separately processed and analyzed in downstream workflows. These pooling barcodes are different from the "transferable molecular identification barcodes" that is the basis of this invention. Synonymous terms of a barcode may be an index, a tag, a nucleotide tag, a MID (molecular identifier).

Pooling barcodes can be added to any target nucleic acid or target nucleotide sequences, including transferable molecular identification barcodes as such, or in combination with other target nucleic acids or target nucleotide sequences such as (from) genomic DNA of an individual. The target nucleotide sequences derived from the transferable molecular identification barcodes will then have two barcode sequences, the minimal barcode sequence derived from the transferable molecular identification barcode sequences and one derived from the pooling barcode sequences. The pooling barcode can be one barcode at one end flanking the target nucleotide sequence, or can be two split barcodes flanking the target nucleotide sequence at each end. For the latter, the two split barcodes can be identical or different (dual indexing). For the latter, the two barcode ends determine combined one pooling barcode and the combination is unique.

As used herein the term "amplification" refers to any means (e.g. linearly, exponentially, isothermally, thermocycling) by which at least a part of at least one target nucleic acid is reproduced, typically in a template-dependent manner, including without limitation, a broad range of techniques for amplifying nucleic acid sequences. Illustrative means for performing an amplifying step include a DNA polymerase reaction, primer extension, reverse transcription, PCR, ligase chain reaction (LCR), oligonucleotide ligation assay (OLA), ligase detection reaction (LDR), ligation followed by Q-replicase amplification, circularization-based DNA synthesis or amplification (HaloPlex™), Molecular Inversion Probe (MIP) DNA synthesis, strand displacement amplification (SDA), hyperbranched strand displacement amplification, multiple displacement amplification (MDA), rolling circle amplification (RCA), loop mediated isothermal amplification (LAMP), smart amplification process (SMAP), isothermal and chimeric primer-initiated amplification of nucleic acids (ICAN®), nucleic acid strand-based amplification (NASBA), transcription-mediated amplification (TMA), and the like, including multiplex versions and combinations thereof, for example but not limited to, PCR/PCR (2-step PCR), primer extension/OLA, primer extension/OLA/PCR, OLA/PCR, MIP/PCR, LDR/PCR, PCR/PCR/PCR (e.g. PCR/(nested-)PCR/(pooling-) PCR), PCR/PCR/LDR, PCR/LDR, LCR/PCR, PCR/LCR (also known as combined chain reaction—CCR), and the like. Descriptions of such techniques can be found in, among other sources, Ausbel et al.; PCR Primer: A Laboratory Manual, Diffenbach, Ed., Cold Spring Harbor Press (1995); The Nucleic Acid Protocols Handbook, R. Rapley, ed., Humana Press, Totowa, N.J. (2002); Innis et al., PCR Protocols: A Guide to Methods and Applications, Academic Press (1990).

Examples, but not limited to, of DNA polymerases, DNA ligases, reverse transcriptases, and mutants and variants thereof, that can be used for amplification and processing of DNA or RNA are: DNA polymerase I, DNA polymerase I large Klenow Fragment, T4 DNA polymerase, T7 DNA polymerase, Terminal Deoxynucleotidyl Transferase, T4 DNA ligase, Taq DNA polymerase, AmpliTaq Gold®, Taq DNA polymerase High Fidelity, Tfl DNA polymerase, Tli DNA polymerase, Tth DNA polymerase, Vent® DNA polymerase, phi29 DNA polymerase, Bst DNA polymerase, Taq DNA ligase, Pfu DNA ligase, AMV Reverse Transcriptase, MMLV Reverse Transcriptase.

As used herein the term "amplicon" refers to a target nucleotide sequence or collection (population) thereof obtained by amplifying a particular nucleic acid sequence by a nucleic acid amplification technique, such as for example PCR. The term "amplicon" broadly includes any collection of molecules produced by any amplification method.

As used herein the term "sequencing template preparation" refers to methods and reactions in which (a) target nucleic acid(s), or target nucleotide sequence(s), are prepared for sequencing. In general, at the end of such a preparation, either linear or circular target nucleotide sequences are obtained that are flanked by one or more adapters. Some adapters are only needed for the preparation of the sequencing template, while other adapters are only needed for the actual sequencing, or a combination thereof. At this moment, most highly parallel sequencing technologies require specific respective adapter sequences in order to perform sequencing on their respective sequencing platform.

Such adapters can be added by an amplification method at a given step. For example, by PCR in which at least one primer comprises a target-specific binding site and an adapter located on the 5' end to the target-specific portion, and a second primer that comprises either only a target-specific portion, or a target-specific portion and an adapter located on the 5' end to the target-specific portion. As used herein with reference to the portion of a primer, the term "target-specific" nucleotide sequence refers to a sequence that can specifically anneal to a primer binding site in a target nucleic acid or a target nucleotide sequence under suitable annealing conditions.

Alternatively, one or more adapters can also, for example, be added by a ligation reaction of ligation adapters at one or both ends of target nucleic acids or target nucleotide sequences. In most applications, the target nucleic acids are first fragmented, e.g. by physical means (e.g. sonication, temperature), by enzymatic means, by tagmentation.

An adapter used for preparing a sequencing template might even have large 5' and 3' overhangs for preparing circular target nucleotide sequence templates. In a HaloPlex™ assay, the larger 5' and 3' overhangs hybridize to both ends of a targeted DNA restriction fragment, thereby guiding the targeted fragments to form circular DNA molecules. The adapter may contain one or more other adapter functions, which are needed for further processing and preparation of the sequencing template and/or performing the actual sequencing, which flank the target nucleotide sequences after circularization.

Different sequencing template preparation methods (assays, panels, kits) are, for example but not limited to: TruSeq® DNA sample preparation (Illumina), Nextera® DNA sample preparation (Illumina), TruSeq Amplicon preparation by primer-extension-ligation (Illumina), TruSeq stranded m RNA library preparation (Illumina), TruSeq RNA Access Library preparation (Illumina), TruSeq Targeted RNA expression (Illumina), Ion Xpress™ plus fragment library preparation (Ion Torrent, Thermo Fisher Scientific), Ion AmpliSeq™ DNA and RNA library preparation (Ion Torrent, Thermo Fisher Scientific), SOLiD™ fragment library preparation (Thermo Fisher Scientific), Titanimum library preparation (454 Life Sciences, Roche), DNA nanoball (DNB) library preparation (Complete Genomics, BGI), SMRTbell template preparation (Pacific Biosciences), MinION library preparation (Oxford Nanopore Technologies), GeneRead library preparation (Qiagen), GeneRead DNAseq gene library preparation (Qiagen), SureSelect$^{XT}$ library preparation (Agilent Technologies), Oligonucleotide-Selective Sequencing (OS-Seq™; Blueprint Genetics), NEBNext® library preparation (New England BioLabs), Access Array™ targeted library enrichment (Fluidigm), SmartChip™ library preparation (Wafergen Biosystems), Multiplex Amplification of Specific Targets for Resequencing (MASTR) (Multiplicom), Devyser multiplex PCR NGS assays (Devyser), HEAT-Seq Target Enrichment (Roche), KAPA library preparation (and Hyper Prep and Hyper Plus) (Kapabiosystems), ThruPLEX®, PicoPLEX™, TransPLEX® library preparations (Rubicon Genomics), Accel-NGS DNA library preparation (Swift Biosciences), Accel-amplicon™ panel preparation (Swift Biosciences), Archer FusionPlex™ and VariantPlex™ library preparation (Archerdx), Immunoseq® and Clonoseq library preparation (Adaptive biotechnologies), library preparation by Single Primer Enrichment Technology (SPET) (NuGEN), Quant-Seq-Flex targeted RNA preparations (Lexogen).

For sequencing template preparation, transferable molecular identification barcodes can be target nucleic acids as such, or mixed with other target nucleic acids such as DNA or RNA from an individual or patient, animal, plant, bacteria, virus or fungus. It will be appreciated by any person skilled in the art that transferable molecular identification barcodes find an application in any method, assay or kit that can prepare sequencing template from target nucleic acids.

As used herein the term "probe" refers to a nucleic acid capable of binding to a target nucleic acid of complementary sequence through one or more types of chemical bonds, generally through complementary base pairing, usually through hydrogen bond formation, thus forming a duplex structure. The probe binds or hybridizes to a probe binding site. The probe can be labeled with a detectable label to permit facile detection of the probe, particularly once that the probe has hybridized to its complementary target. Alternatively, the probe may be unlabeled, but may be detectable by specific binding with a ligand that is labeled, either directly or indirectly. Probes can vary significantly in size. Generally, probes are at least 7 to 15 nucleotides in length. Other probes are at least 20, 30, or 40 nucleotides long. Still other probes are somewhat longer, being at least 50, 60, 70, 80, or 90 nucleotides long. Yet other probes are longer still, and are at least 100, 150, 200 or more nucleotides long. Probes can also be of any length that is within any range bounded by any of the above values (e.g., 15-20 nucleotides in length).

A probe can be perfectly complementary to the target nucleic acid sequence or can be less than perfectly complementary. In certain embodiments, the primer has at least 50% identity to the complement of the target nucleic acid sequence over a sequence of at least 7 nucleotides, more typically over a sequence in the range of 10-30 nucleotides, and often over a sequence of at least 14-25 nucleotides, and more often has at least 65% identity, at least 75% identity, at least 85% identity, at least 90% identity, or at least 95%, 96%, 97%. 98%, or 99% identity. It will be understood that certain bases (e.g., the 3' base of a primer) are generally desirably perfectly complementary to corresponding bases of the target nucleic acid sequence. Primer and probes typically anneal to the target sequence under stringent hybridization conditions.

As used herein the term "capturing oligonucleotide" refers to one or more oligonucleotides or probes that hybridize to specific targets of interest of target nucleic acids or target nucleotide sequences that will be only processed from a more complex mixture of nucleic acids. The specific sequence of a target to which a capturing oligonucleotide binds might here be also termed as an oligonucleotide binding sequence.

In this way only genomic regions of interest will be processed, such as sequencing, by isolation the DNA regions of a genome of interest through hybridization based sequence capture with capturing oligonucleotides. The oligonucleotide binding site in a target nucleic acid is termed as the 'capturing sequence'. A capturing sequence in a nucleotide barcode sequence is a sequence not encoded in any naturally occurring genome, bacterial or viral DNA (and thus not found in cloning vectors, or more specifically cloning vector backbones), or have a sequence that is less than 1%, less than 2%, less than 3%, less than 4%, less than 5%, less than 10%, less than 15%, less than 20%, less than 25%, less than 30%, less than 40%, less than 50% homologous to a sequence encoded in any naturally occurring genome, viral, bacterial DNA.

The capturing probes can contain modifications to facilitate isolation. In most cases, these probes are biotinylated.

For example, targets of nucleic acids of interest can be exon sequences of one or more genes, or even exon sequences of the majority of all genes of a genome which is known as an exome. Target nucleotide sequences may have been prepared by a sequencing template library preparation method in which the target nucleotide sequences represent, for example, less than 1-3% of the total nucleotide sequences. If the total sequencing template library would be sequenced, only less than 1-3% of the obtained sequences will be of interest and used. The target nucleotide sequences of interest from the total library can be selectively enriched by specific hybridization using capturing oligonucleotides directed against these nucleotide sequences of interest regions, before sequencing. Capturing can be either performed in solution or on physical supports (arrays). When the capturing oligonucleotides are biotinylated, the hybridized fragments of interest can be easily isolated from the non-hybridized fragments that are not of interest through the use of streptavidin-coated beads. Specific nucleic acid targets could be also the nucleotide barcodes from a transferable molecular identification barcode, for which a single capturing oligonucleotide, which is directed against a constant sequence region in the transferable molecular identification barcodes, can be designed and prepared, so that all types of nucleotide barcodes can be isolated and characterized, irrespective of the different minimal barcode sequences that is present. Transferable molecular identification barcodes could be captured as such, are in combination with other target nucleic acids if the transferable molecular identification barcodes are mixed with other nucleic acid targets, such as the DNA of an individual or patient.

As used herein the term 'enrichment' of (a) particular region(s) in a DNA mixture (e.g. genome, genome mixed with transferable molecular identification barcodes) refers to the generation and/or isolation of target nucleotide sequences from target nucleic acids in nucleic acids through amplification or (hybridization based sequence) capturing.

Different capturing methods, assays, kits are for example, but not limited to: TruSight sequencing panels (Illumina), Nextera Rapid Capture kits (Illumina), TargetSeq™ Exome enrichment (Thermo Fisher Scientific), HaloPlex™ enrichment (Agilent Technologies), SureSelect Target enrichment (Agilent Technologies), SeqCap EZ enrichment (Roche NimbleGen), xGEN® Target capture (Integrated DNA Technologies).

As used herein the term "equalizing oligonucleotide" refers to an oligonucleotide or probe that specifically hybridizes to a constant sequence that is found in certain, or all, target nucleotide sequences. The sequence to which an equalizing oligonucleotide can bind in a target nucleic acid is termed as the 'equalizing sequence'. An equalizing sequence is a sequence not encoded in any naturally occurring genome, bacterial or viral DNA (and thus not found in cloning vectors, or more specifically cloning vector backbones), or have a sequence that is less than 1%, less than 2%, less than 3%, less than 4%, less than 5%, less than 10%, less than 15%, less than 20%, less than 25%, less than 30%, less than 40%, less than 50% homologous to a sequence encoded in any naturally occurring genome, viral, bacterial DNA.

Equalizing oligonucleotides are used to normalize the target nucleotide sequences in different processed samples to a more equal level. Nucleotide barcode sequences in transferable molecular identification barcodes could be equalized as such, or equalized with other target nucleotide sequences if the transferable molecular identification barcode was mixed with other nucleic acid targets, such as the DNA of an individual or patient. Nucleotide barcode sequences may even harbor a second equalizing sequence not present in nucleotide sequences from other added nucleic acids, e.g. through an equalizing sequence present in the constant sequence region in the nucleotide barcode sequences, to allow differently equalization of the nucleotide barcode sequences from the other target nucleotide sequences, are to fine tune equalization of the nucleotide barcode sequences from the other nucleotide sequences further. An equalizing oligonucleotide can be biotinylated to facilitate easy further processing, such as isolation through streptavidin-coated beads.

As used herein the term "highly parallel sequencing" refers to high-throughput approaches of DNA sequencing using the concept of massively parallel processing. Many highly parallel sequencing platforms differ in engineering configurations and sequencing chemistry. They mostly share the technical paradigm of massive parallel sequencing via spatially separated, clonally amplified DNA template or single DNA molecules in a flow cell. Synonymous terms used are, for example, next-generation sequencing (NGS), second-generation sequencing, third-generation sequencing, massive parallel sequencing, massively parallel sequencing.

Different highly parallel sequencing chemistry and platforms for example, but not limited to, are: pyrosequencing, GS FLX (454 Life Sciences, Roche); Sequencing by Synthessis, Reversible Dye Terminator, HiSeq, MiSeq (Illumina); oligonucleotide chained ligation, SOLiD ((Thermo Fisher Scientific), Ion Semiconductor Sequencing based on proton detection, Ion PGM™, Ion Proton™, Ion S5™ (Ion Torrent, Thermo Fisher Scientific) and GenapSys, Ion Semiconductor Sequencing based on fluorescence detection by photodiodes, Firefly (Illumina), Oligonucleotide Unchained Ligation (Complete Genomics, BGI), Reversible Dye Terminator, Heliscope (Helicos Biosciences), phospholinked fluorescent nucleotides, Real-Time SMRT® DNA sequencing, Pacbio RS, (Pacific Biosciences), Nanopore Sequencing, MinION™, PromethION™, GridION™, (Oxford Nanopores Technologies), NanoTag nanopore-based Sequencing (Genia Technologies/Roche), Sequencing By Xpansion (SBX, Stratos Genomics). It will be appreciated by any person skilled in the art that transferable molecular identification barcodes find an application in any parallel sequencing method of nucleic acids in which the detection of nucleic acids, or by-products thereof, is based on any physical, chemical, and/or enzymatically processing or properties thereof.

As used herein the term 'nucleotide barcode sequence identifier sequence', also abbreviated as 'identifier sequence', refers to one or more adapter sequences in one or both flanking constant sequences of a nucleotide barcode sequence to identify a DNA molecule, or sequenced sequence thereof, as a nucleotide barcode sequence. A nucleotide barcode sequence identifier sequence is a sequence not encoded in any naturally occurring genome, bacterial or viral DNA (and thus not found in cloning vectors, or more specifically cloning vector backbones), or have a sequence that is less than 1%, less than 2%, less than 3%, less than 4%, less than 5%, less than 10%, less than 15%, less than 20%, less than 25%, less than 30%, less than 40%, less than 50% homologous to a sequence encoded in any naturally occurring genome, viral, bacterial DNA. Different batches of transferable molecular identification barcodes might have a different nucleotide barcode sequence identifier sequence, and respectively used in different applications, and/or different steps in the same application, so that the nucleotide barcode sequence identifier sequence identifies the different batch, and thus the application and/or step in an application.

As used herein the term 'extracting sequence' refers to one or more adapter sequences in one or both flanking sequences to the minimal barcode sequence in a nucleotide barcode sequence to extract the actual minimal barcode sequence. An extracting sequence is a sequence not encoded in any naturally occurring genome, bacterial or viral DNA (and thus not found in cloning vectors, or more specifically cloning vector backbones), or have a sequence that is less than 1%, less than 2%, less than 3%, less than 4%, less than 5%, less than 10%, less than 15%, less than 20%, less than 25%, less than 30%, less than 40%, less than 50% homologous to a sequence encoded in any naturally occurring genome, viral, bacterial DNA.

An extracting sequence may be identical, or overlapping, with the nucleotide barcode sequence identifier sequence. Typically, the bioinformatic analysis of sequenced nucleotide barcode sequences, requires two steps, or even two informatic pipelines or programs. The first program isolates sequenced nucleotide barcode sequences from all sequenced sequences through the nucleotide barcode sequence identifier sequences, the second program extracts the minimal nucleotide barcode sequences in these sequenced nucleotide barcode sequences through the extracting sequences. In case that the extracting sequences are identical between different batches of transferable molecular identification barcodes, but not the nucleotide barcode sequence identifier sequences, a different first bioinformatic program (are a different setting in the program) has to be used for each batch of transferable molecular identification barcodes depending on the identifier sequence, but the same second informatic program (are a same setting in the program) could be used for extraction of all minimal nucleotide barcode sequences from different batches of transferable molecular identification barcodes (having different nucleotide barcode sequence identifier sequences).

As used herein the term "carrier(s)" refers to substrates and containers containing transferable molecular identification barcodes. A carrier could be used for collecting biological samples. A carrier could be used for transferring its content to another carrier that collects a biological sample.

Part of the present invention makes use of the genetic code (the sequence of As, Cs, Ts, Gs, Us representing the bases present in nucleic acids, i.e. adenine, cytosine, tyrosine, guanine and uracil, respectively) to create unique codes, which are herein called as nucleotide barcodes. These can be used for identifiers of items of a particular kind, origin, processing or treatment, such as a biological sample, of human, animal, plant, bacteria, virus or fungus origin, and are used as transferable molecular identification barcodes. Such biological samples may be obtained from any suitable location, including from organisms, whole cells, single cells, cell preparations and cell-free compositions from any organism, tissue, cell, or environment. A biological sample may be also cell-free, such as circulating nucleic acids (e.g. DNA, RNA), such as circulating tumor DNA in the blood, or circulating fetal DNA in the blood of a pregnant woman. A biological sample may be obtained from environmental biopsies, aspirates, formalin fixed embedded tissues, air, agricultural samples, soil samples, petroleum samples, water samples, or dust samples. In some instances, a sample may be obtained from bodily fluids, which may include blood, urine, feces, serum, lymph, saliva, mucosal secretions, perspiration, central nervous system fluid, vaginal fluid, or semen. Samples may also be obtained from manufactured products, such as cosmetics, foods (such as meat, milk, wine, olive oil), personal care products, and the like. Samples may be the products of experimental manipulation including recombinant cloning, polynucleotide amplification, polymerase chain reaction (PCR) amplification, purification methods (such as purification of genomic DNA or RNA), and synthesis reactions.

Short DNA molecules or oligonucleotides can be made to have any desired sequence of the "letters" of the genetic code, and particular combinations of those letters of a DNA molecule can be designated to have particular meaning.

One preferred way for the production of small oligonucleotides is by chemical synthesis using building blocks that are protected phosphoramidites of natural or chemically modified nucleosides or, to a lesser extent, of non-nucleosidic compounds. The oligonucleotide chain assembly proceeds during synthesis in the direction from the 3'- to 5'-terminus by following a routine procedure referred to as a synthetic cycle. Completion of a single synthetic cycle results in the addition of one nucleotide residue to the growing chain. A less than 100% yield of each synthetic step and the occurrence of side reactions set practical limits of the efficiency of the process so that the maximum length of synthetic oligonucleotides hardly exceeds 200 nucleotide residues. With this procedure oligonucleotides are produced one by one.

Oligonucleotides can be also produced in parallel on microarrays using a variety of technologies, such as photolithography using pre-made masks, photolithography using dynamic micromirror devices, ink-jet printing, electrochemistry on microelectrode arrays.

The number of different oligonucleotides that can be synthesized is enormous. For example, a total of 1,024 ($4^5$) different oligonucleotides can be generated when oligonucleotides of 5 nucleotides long are produced. More than 1 million ($4^{10}$) different oligonucleotides can be produced when oligonucleotides of 10 nucleotides long are produced (Table 1).

TABLE 1

Number of different nucleotide sequences depending on the length of the DNA sequences.

| Length | Number of different nucleotide sequences |
|---|---|
| 1 | 4 |
| 2 | 16 |
| 3 | 64 |
| 4 | 256 |
| 5 | 1024 |
| 6 | 4096 |
| 7 | 16384 |
| 8 | 65536 |
| 9 | 262144 |
| 10 | 1048576 |
| 15 | 1073741824 |
| 20 | 1099511627776 |
| 25 | 1125899906842620 |

Each such nucleotide barcode sequence could be used as a transferable molecular identification barcode for labelling one single item, such as a biological sample. The synthesis of such a high number nucleotide barcodes is, however, quiet time demanding and costly.

A more economic favorable way would be the use of more than one DNA molecule to compose a transferable molecular identification barcode that can be used to mark a sample or item. When 3 nucleotide barcodes are used per transferable molecular identification barcode, 30 different nucleotide barcodes allow the generation of 1,000 different unique transferable molecular identification barcodes. When 6 nucleotide barcodes are used per transferable molecular identification barcode, 60 different nucleotide barcodes allow the generation of 1 million different unique transferable molecular identification barcodes, and so on (Table 2).

TABLE 2

Number of different transferable molecular identification barcodes that can be prepared in function of the number of nucleotide barcodes used per transferable molecular identification barcode.

| Different nucleotide barcodes per transferable molecular identification barcode (a) | Number of nucleotide barcodes needed | Number of different transferable molecular identification barcodes |
|---|---|---|
| 2 | 20 | 100 |
| 3 | 30 | 1000 |
| 4 | 40 | 10000 |
| 5 | 50 | 100000 |
| 6 | 60 | 1000000 |
| 7 | 70 | 10000000 |
| 8 | 80 | 100000000 |
| 9 | 90 | 1000000000 |
| 10 | 100 | 10000000000 |
| 15 | 150 | 1000000000000000 |
| 20 | 200 | 100000000000000000000 |
| 25 | 250 | 10000000000000000000000000 |

(a) Sets of 10 nucleotide barcodes are used; for each nucleotide barcode, one can choose between 10 nucleotide barcodes Using a mixture of nucleotide barcodes for the generation of transferable molecular identification barcode is thus most economical. The more nucleotide barcodes are used per transferable molecular identification barcode, the more economical the process. To produce a lot of transferable molecular identification barcodes each consisting of 6 nucleotide barcodes, only 60 different nucleotide barcodes will be needed for the generation of 1 million different transferable molecular identification barcodes that are built of all combinations of 6 nucleotide barcodes. This in contrast to 30,000 different nucleotide barcodes that will be needed for the construction of 1 million different transferable molecular identification barcodes that are only built of 3 DNA molecules (Table 3).

ferable molecular identification barcode is unique as long as the combined mixture of nucleotide barcodes is unique. When a transferable molecular identification barcode is built up of x nucleotide barcodes, two transferable molecular identification barcodes can be still unique when they have x−1 nucleotide barcodes in common, but differ for the $x^{th}$ nucleotide barcode.

In order to make use of transferable molecular identification barcodes, one should at the end detect, identify and/or characterize the nucleotide barcodes in the transferable molecular identification barcode. When transferable molecular identification barcodes are used as such, only the nucleotide barcodes need to be characterized. When transferable molecular identification barcodes are used in more

TABLE 3

Number of different transferable molecular identification barcodes needed to produce a given million transferable molecular identification barcodes depending on the number of nucleotide barcodes in a transferable molecular identification barcode.

| Different nucleotide barcodes per transferable molecular identification barcode (a) | Number of nucleotide barcodes needed | Number of different transferable molecular identification barcodes | For 1 million transferable molecular identification barcodes | For 10 million transferable molecular identification barcodes | For 100 million transferable molecular identification barcodes |
|---|---|---|---|---|---|
| 2 | 20 | 100 | 200000 | 2000000 | 20000000 |
| 3 | 30 | 1000 | 30000 | 300000 | 3000000 |
| 4 | 40 | 10000 | 4000 | 40000 | 400000 |
| 5 | 50 | 100000 | 500 | 5000 | 50000 |
| 6 | 60 | 1000000 | 60 | 600 | 6000 |
| 7 | 70 | 10000000 | | 70 | 700 |
| 8 | 80 | 100000000 | | | 80 |

(a) Sets of 10 nucleotide barcodes are used; for each nucleotide barcode, one can choose between 10 nucleotide barcodes The technical and economic feasibility of preparing and using unique transferable molecular identification barcodes lies thus in the combinational effect of different nucleotide barcodes. One transferable molecular identification barcode is then a mixture of different nucleotide barcodes. A transcomplex applications, such as in genetic tests, both the nucleotide barcodes and other nucleic targets under investigation need to be characterized. This can be done by molecular techniques as known to a person skilled in the art and described in: Molecular Cloning: A Laboratory Manual, by Sambrook and Russel, 3rd Edition, Cold Spring Harbor Laboratory Press, 2001 (the disclosure of which is incorporated herein by reference), such as DNA synthesis, polymerization, ligation, PCR, RT-PCR, sequencing.

Processing of single stranded oligonucleotide barcodes for characterization purposes requires at some stage their conversion to double stranded DNA molecules. One preferred way, as described in FIG. 1, is the ligation of two, at least partly, double stranded ligation adapters. The double stranded adapters may carry other adapter sequences for specific downstream processing. The partly double stranded may also carry other features, such as hairpin structures and looped structures. The nucleotide barcodes are first phosphorylated. Alternatively, already phosphorylated nucleotide barcodes are used for the preparation of transferable molecular identification barcodes. One double stranded adapter has a 5' nucleotide overhang which can bind to one end of a single stranded nucleotide barcode, and the second double stranded adapter has a 3' nucleotide overhang which can bind to the other end of a nucleotide barcode. In the former double stranded adapter, the DNA strand with the 5' nucleotide overhang is phosphorylated at its 5' end. In the latter double stranded adapter with the 3' overhang, the opposite strand without the 3' overhang is phosphorylated at its 5' end. After hybridization of these double stranded adapters to a single stranded nucleotide barcode sequence, a new complementary DNA strand can be synthesized with a DNA polymerase in which the DNA strand with the 3' nucleotide overhang in de 3' overhang adapter is extended, using the bound nucleotide barcode as template until it reaches the 5" nucleotide overhang of the adapter at the other end. A DNA ligase is then used to ligate the three open nicks so that complete double stranded nucleotide barcodes are obtained. The overhangs in both double stranded adapters can be 1 or more nucleotides long. The length of the overhang of both adapters can be identical or different in length. When double stranded ligation adapters are used that have only 1 nucleotide overhang, one needs 4 different adapters, i.e. one with an A overhang, one with a C overhang, one with a G overhang and one with a T overhang. They can of course be mixed. When both the 5' and 3' overhang double stranded ligation adapters have 1-nucleotide overhangs one thus needs a mixture of 8 different adapters in order to make any nucleotide barcode with any sequence double stranded.

Rather than using single stranded nucleotide barcodes for the generation of transferable molecular identification barcodes, double stranded nucleotide barcodes are used from the onset to produce transferable molecular identification barcodes. They may carry adapter sequences for specific downstream processing functions and applications. The advantage is that some or all necessary features for their processing, characterization and/or identification are then already present in the nucleotide barcode molecules, rather than attaching these features by ligation afterwards during their processing for characterization.

Figure 2:
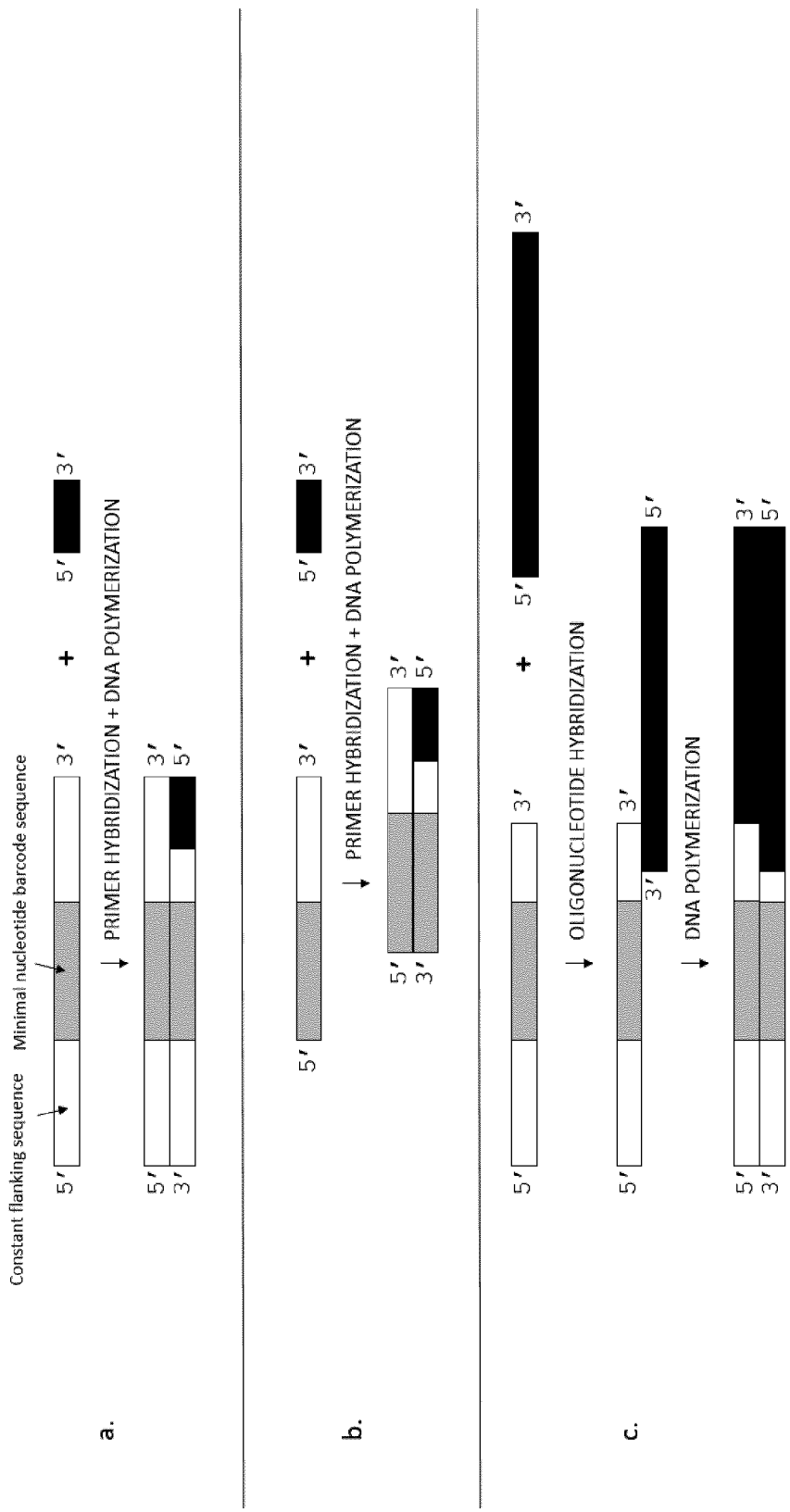
FIG. 2. Preparation of double stranded nucleotide barcodes from single stranded oligonucleotides.

FIG. 2 describes three preferred ways of constructing double stranded nucleotide barcodes. In a first strategy (FIG. 2a), longer single stranded oligonucleotides are used which carry a different unique minimal nucleotide barcode sequence $N_x$ (N being any nucleotide, x being the number of nucleotides), which is flanked by constant sequences in common for each oligonucleotide. In each oligonucleotide, the unique sequence will in the end be the minimal nucleotide barcode sequence. The constant sequences, or part thereof, may have other adapter functions for specific downstream processing functions. These oligonucleotides can then be rendered doubled stranded by a DNA synthesis reaction using a primer having a primer binding site in the flanking constant sequence region 3' to the $N_x$ sequence, so that a new complementary DNA strand is synthesized over the $N_x$ sequence until the end of the other second constant sequence region. When the primer binds right at the complete end of the 3' constant sequence region, a complete double stranded DNA molecule is obtained, otherwise the obtained double stranded nucleotide barcode molecules will be sticky at one end. In a second strategy (FIG. 2b), single stranded oligonucleotides are used which carry a different unique minimal nucleotide barcode sequence $N_x$ characteristic for each type of oligonucleotide followed by a constant sequence, so that the minimal barcode sequence region is only flanked at one (3') site with a constant sequence region. Again here, the constant sequences, or part thereof, may have other adapter functions for specific downstream processing functions. These oligonucleotides can then be rendered doubled stranded by a DNA synthesis reaction using a primer having a primer binding site in the flanking constant sequence region 3' to the minimal barcode sequence, so that a new complementary DNA strand is synthesized over the minimal barcode sequence alone and ends there. When the primer binds right at the complete end of the 3' constant sequence region, a complete double stranded DNA molecule is obtained, otherwise the obtained double stranded nucleotide barcode molecules will be sticky at one end. Very likely such double stranded DNA molecules will still require downstream processing, such as a ligation step with a double stranded ligation adapter to add in the end also constant sequences at the site were constant sequence regions were originally not present. A third strategy (FIG. 2c) is an alternative to the first strategy in which again longer single stranded oligonucleotides are used which carry a different unique minimal nucleotide barcode sequence $N_x$, which are flanked by constant sequences in common for each oligonucleotide. In each oligonucleotide, the unique sequence $N_x$ will be minimal nucleotide barcode sequence. The 3' constant sequence may have a smaller or larger size compared to the 5' constant sequence sufficient for hybridization with another oligonucleotide. A second single stranded oligonucleotide is combined that carries at its 3' end a sequence complementary to the constant sequence region, or part thereof, 3' to the minimal barcode sequence region of the first single stranded oligonucleotide, but which carries additional 5' constant sequences. Again here, the constant sequences in either single stranded oligonucleotides, or part thereof, may have other adapter functions for specific downstream processing. After hybridization of both types of single stranded oligonucleotides at their complementary shared constant 3' sequence regions, new DNA strands are synthesized extending from each oligonucleotide in which the other hybridizing oligonucleotide is used as template, so that complete double stranded nucleotide barcodes are obtained. Optionally one or more additional rounds of DNA synthesis reaction may be performed by (an) additional oligonucleotide(s) with a constant sequence, that may carry adapter functions for specific downstream processing, which carries at its 3' end a sequence complementary to the constant sequence region located 3' in the DNA molecules generated in the previous round. In this way nucleotide barcodes can be generated with long constant adapter regions that may exceed the typical length of single oligonucleotides. Rather than adding each new oligonucleotide in serial new reactions, all such oligonucleotides can be also mixed in one single reaction and DNA synthesis can be performed for a number of cycles with a thermostable DNA polymerase. Double stranded barcodes containing a minimal barcode sequence and the complete flanking sequences can be also synthesized in one run using methods used in synthetic biology, such as gBlocks® Gene Fragments (Integrated DNA Technologies).

Examples, but not limited to, of single stranded or double stranded nucleotide barcodes having different adapter functions that are obtained in this way are shown in FIG. 3.

One or both flanking constant sequences are an artificial sequence not found in nature (not found in human, animal, plant, bacterium, virus, fungus, even not in cloning vectors (vector backbone) used in molecular biological protocols and tools. When, in a sequencing application, a nucleotide sequence is found that is identical to a constant flanking sequence, or (a) part(s) thereof, it can be concluded that it originates from a nucleotide barcode sequence and in this way nucleotide barcode sequences can be identified. Especially when transferable molecular identification barcodes are mixed with other target nucleic acids, the sequence reads originating from the nucleotide barcode sequences can be identified. Indeed, sequence reads obtained from nucleotide barcodes can then be differently processed, e.g. by different bio-informatic pipelines (e.g. a pipeline for identification and quantitation of the nucleotide barcodes, a pipeline for mapping and variant calling of the sequence reads originating for the other target nucleic acids). The constant flanking sequences preferentially have a small GC % content variation, preferentially in the range of 35-65%. For example, any continuous sequence of X nucleotides (X nucleotides being 18, 19, 20, 21, 22, 23, 24, 25, 30, 35, 40, 45 and/or 50) of this flanking sequence having a preferential GC-content between between 35-60%, between 40-60%, between 45-60%, between 50-60%, between 55-65%. For example, any continuous sequence of X nucleotides (X nucleotides being 18, 19, 20, 21, 22, 23, 24, 25, 30, 35, 40, 45 and/or 50) of this flanking sequence having a preferential Tm between 50° C. and 75° C., between 55° C. and 75° C., between 60° C. and 75° C., between 60° C. and 70° C. In this way, any desired oligonucleotide binding site (e.g. for a primer for amplification or capturing) can be designed in the most flexible and efficient way. Indeed, many types of genetic NGS tests (from different companies) are available using different technologies in which target regions of a genome of interest are enriched for sequencing, e.g. through multiplex PCR, primer-extension-ligation, etc. Each type of test uses their specific test conditions. For example, one type of test may use a multiplex amplification in which all primers have a given about the same Tm, while another vendor uses primers with another Tm. Also the obtained amplicons in a test that are obtained may have a given specific size range so that all amplicons are most equally amplified, and the selected size might vary between different tests. Indeed, smaller amplicons are in general more efficiently amplified than larger amplicons so that the length of the obtained amplicons is also kept to a certain range which might be specific characteristic of a given test. If these tests want to make use of transferable molecular identification barcodes for quality control, primers have to be added or included in their assay that enrich nucleotide barcode sequences. The primer(s) used for enrichment of the nucleotide barcode in their given assay should then preferentially have the same characteristics, such as Tm, as the other primers in their assay. By having a more continuous GC content range in the constant flanking region, the selection and addition of (a) primer(s) that allow enrichment of transferable molecular identification barcodes are most easily integrated in any test. If there would be sequence blocks with very low (<20% or very high (>70%) GC criteria, the criteria of finding (a) primer(s) binding site having a given Tm (which is mostly in the range of 30-55° C.), and position so that amplicons of a given specific size range are obtained, might be difficult to obtain, or even impossible for some tests.

Figure 4:
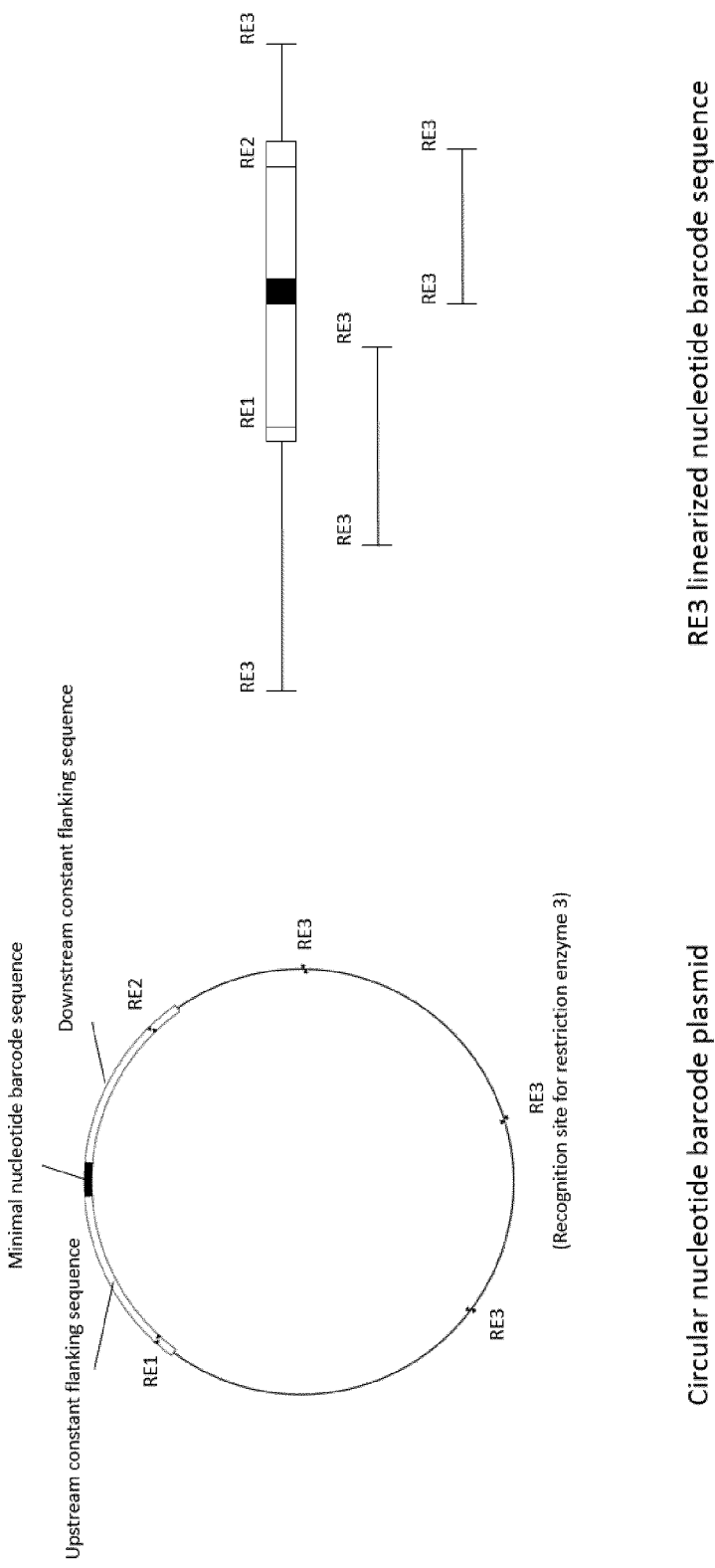

Examples of isolated upstream constant flanking sequences, as described for example in FIGS. 3 and 4, starting from restriction enzyme recognition site RE1 and ending before the minimal nucleotide barcode sequence, are sequences [SEQ ID NO:1], [SEQ ID NO:2], [SEQ ID NO:3], [SEQ ID NO:4], [SEQ ID NO:5], [SEQ ID NO: 6], [SEQ ID NO: 7], [SEQ ID NO: 8], [SEQ ID NO: 9], [SEQ ID NO:10]. Examples of isolated downstream constant flanking sequences, as described for example in FIGS. 3 and 4, starting after the minimal nucleotide barcode sequence and ending at restriction enzyme recognition site RE2, are sequences [SEQ ID NO:11], [SEQ ID NO:12], [SEQ ID NO:13], [SEQ ID NO:14], [SEQ ID NO:15], [SEQ ID NO:16], [SEQ ID NO:17], [SEQ ID NO:18], [SEQ ID NO:19], [SEQ ID NO:20]

Variants of the sequences [SEQ ID NO:1] to [SEQ ID NO:20] have alternative restriction site recognition sequences, depending on the cloning site in a vector.

Alternatively, [SEQ ID NO:1] to [SEQ ID NO:10] are downstream constant flanking sequences and [SEQ ID NO:11] to [SEQ ID NO:20] are upstream constant flanking sequences.

Alternatively, one or more of the [SEQ ID NO:1] to [SEQ ID NO:20] sequences can be the reverse complement sequence of the respective [SEQ ID NO:1] to [SEQ ID NO:20] sequences.

Alternatively, upstream and/or downstream constant flanking sequences are sequences [SEQ ID NO:1] to [SEQ ID NO:20] are sequences showing more than 70%, more than 80%, more than 90%, more than 95%, more than 97% or more than 99% sequence identity with the sequence identity of the respective sequences [SEQ ID NO:1] to [SEQ ID NO:20]. Differences in sequence identity can be e.g. the result from adding or deleting recognition sites for restriction enzymes.

Yet alternatively, upstream and/or downstream constant flanking sequences comprising the sequences [SEQ ID NO:1] to [SEQ ID NO:20], by the presence of additional nucleotides sequence between the indicated restriction enzyme recognition sequences and the constant sequences and/or between the constant sequence and the minimal nucleotide barcode sequence.

Yet alternatively, upstream and/or downstream constant flanking sequences comprise or consist of a fragment of the sequences [SEQ ID NO:1] to [SEQ ID NO:20], namely a fragment of at least 200 nucleotides, of at least 300 nucleotides, of at least 350 nucleotides, of at least 375 nucleotides, or of at least 390 nucleotides.

These double stranded DNA molecules may be also further cloned in plasmids or in other replicative constructs. Adapters that harbor recognition sites for restriction enzymes in the constant flanking sequences of these double stranded DNA molecules may facilitate cloning of these double stranded DNA molecules in plasmids. For example, both constant flanking sequences might harbor a recognition site for the same restriction enzyme, or for two different restriction enzymes. Recognition sites for two different restriction enzymes in each flanking site, which produce sticky DNA ends after digestion, are preferred since they would allow efficient directional cloning of the double stranded DNA molecules in plasmids.

The use of plasmids to produce transferable molecular identification barcodes has the advantage that complete lots of many transferable molecular identification barcodes can start from only one single oligonucleotide or one synthetic DNA fragment. Indeed, when single oligonucleotides having a given unique nucleotide barcode sequence, or oligonucleotides that are used for the construction of double stranded nucleotide barcode molecules having a given nucleotide barcode sequence, are flanked by the same constant sequences, one needs to synthesize these different oligonucleotides one by one. This can be circumvented, and will be more economically, when transferable molecular identification barcodes in a replicative molecule, such as plasmids, are used. Then only one single oligonucleotide synthesis reaction is needed. During an oligonucleotide synthesis reaction, more than one nucleotide, or even all four possible nucleotides can be added during a given cycle in the synthesis step and incorporated in the oligonucleotide. When all four building blocks (N) are added over a continuous number of cycles, all possible sequences of a length (x) that equals the number of these cycles will be synthesized and thus oligonucleotides having all possible random sequences of that length $N_x$ will be obtained in a single synthesis reaction. When single nucleotides are added and incorporated during the preceding and following cycles of the cycles when more than one nucleotide was added, a mixture of oligonucleotides will be obtained in a single tube having random nucleotide barcode sequences ($N_x$), all flanked with the same constant sequences. Analogously, a complete mixture of synthetic DNA fragments can be produced, which contain a different minimal barcode sequence and the same complete flanking sequences, such as gBlocks® Gene Fragments (Integrated DNA Technologies).

The length of the actual minimal nucleotide barcode can be any suitable length, depending on the application. When all possible nucleotides are allowed over a stretch of 10 cycles, $4^{10}$ (1,048,576) different nucleotide barcode sequences can be synthesized in a single oligonucleotide synthesis reaction. When all possible nucleotides are allowed over a stretch of 25 cycles, $4^{25}$ (1,125,899,906,842,620) different nucleotide barcode sequences can be synthesized in a single oligonucleotide synthesis reaction (Table 1). In some case, the actual minimal barcode sequences can be about 2 to about 500 nucleotides in length, about 2 to about 100 nucleotides in length, about 2 to about 50 nucleotides in length, about 2 to about 25 nucleotides in length, about 6 to about 25 nucleotides in length, or about 4 to 25 nucleotides in length. In some case, a minimal barcode sequence is greater than about 10, 20, 100, 500, 750, 1000, 5000 or 10000 nucleotides in length.

Identical adapters located in the constant flanking sequence regions to the minimal barcode $N_x$ sequence of such a mixture of single stranded oligonucleotides allow their conversion to double stranded DNA molecules in a limited number of reactions, or even a single reaction, as described above. From this mixture or library of double stranded DNA molecules having theoretically all possible minimal barcode $N_x$ sequences, plasmid libraries can be prepared as described above containing all these possible minimal barcode $N_x$ sequences. Such a plasmid library carrying containing all these possible minimal barcode $N_x$ sequences can then be used for the transformation of bacterial cells so that a bacterial library is obtained which carry these different plasmids with all these possible minimal barcode $N_x$ sequences. From such a bacterial library, glycerol stocks can be generated for future use. At each level, i.e. the oligonucleotides with any possible minimal barcode $N_x$ sequence, double stranded DNA molecules thereof, plasmids thereof, bacterial cultures thereof, are obtained in a single tube for lifetime use, with straightforward methods as known to a person skilled in the art and described in: Molecular Cloning: A Laboratory Manual, by Sambrook and Russel, 3rd Edition, Cold Spring Harbor Laboratory Press, 2001. Each of the nucleotide barcode composition formats can be used for the generation of transferable molecular identification barcodes. Even bacterial cells carrying nucleotide barcodes can be used to produce transferable molecular identification barcodes and used as such in applications. Bacteria transformed with plasmids are here described, but any replicative construct and host for a replicative construct can be used.

Individual plasmids carrying one given minimal nucleotide barcode sequence of all available $N_x$ random sequences can be easily obtained from such bacterial cultures after agar plate culturing whenever needed, from which individual colonies can then be picked and further grown up for harvesting sufficient amounts of plasmid carrying a given minimal nucleotide barcode sequence using methods as known to a person skilled in the art. Only 60 bacterial colonies should be picked, isolated and grown up and plasmid prepped for generating 1 million different transferable molecular identification barcodes, if each transferable molecular identification barcode is buildup of 6 different nucleotide barcode plasmids (see table 2).

In applications of transferable molecular identification barcodes, the nucleotide bar sequences have to be characterized and identified in the end. Highly parallel sequencing could be a method for characterization of these sequences. The minimal barcode sequence will be identifiable by its location between the constant flanking sequences. Typical sequence read lengths obtained by the current mostly used commercial highly parallel sequencing technologies are 100-150 nucleotides, or even more, long. Also at least some part of the flanking sequences of the minimal barcode sequence region should be sequenced in order to identify and process nucleotide barcode sequences, especially if they are present in a mixture that contains other target nucleic acids for sequencing.

Possibly also pooling barcode sequences should be sequenced. After subtraction of these sequences in sequence reads that are typically 100-150 nucleotide long, this still allows minimal nucleotide barcode sequences of 50-100 nucleotides long, i.e. allow up to $4^{50}$-$4^{100}$ unique nucleotide barcode sequences. For practical reasons, it might be of interest to use minimal nucleotide barcode sequences that have a relative lower length range. First at all, the number of different unique nucleotide barcode sequences that can already be obtained with minimal nucleotide barcode sequences of 25 nucleotides long already exceeds the number of nucleotide barcode sequences that might be ever needed. Secondly, certain highly parallel sequencing applications will even not require 100-150 nucleotide long sequence reads. For example, in highly parallel sequencing transcriptome studies only short sequence reads of 25-35 nucleotide longs may be needed to allow transcript identification. Although longer minimal nucleotide barcode sequences can still be used in such applications, by simply neglecting the nucleotide barcode sequence obtained beyond nucleotide positions 25-35, since the first 25 nucleotides of the minimal nucleotide barcode sequence will be very likely already unique, the analysis of such data may be more complex and will require additional (bio-)informatic processing tools. Given the already sufficient number of different nucleotide barcodes that can already be obtained with minimal nucleotide barcode sequences that are 25 nucleotides, additional (bio-)informatics processing is then an unnecessary additional effort.

Rather than simply identifying which nucleotide sequences are derived from nucleotide barcodes, e.g. through a nucleotide barcode sequence identifier sequence that is located in one or both constant flanking sequences, the actual minimal barcode sequence may be needed to be identified, such as for qualification (identity) and/or quantification (number) purposes. Such as in genetic test where transferable DNA barcodes are mixed for quality control with other nucleic acids to be analyzed for mutations.

The minimal nucleotide barcode sequence can be identified by its location in/between extracting sequences located in both constant flanking sequences, or starting from, or ending at an extracting sequence located in one constant flanking sequences.

Any sequence in the constant flanking sequences could be used, however the most efficient ones are the nucleotides directly flanking the minimal nucleotide barcode sequence. For example, when the minimal barcode sequence is 25 nucleotide sequences long, the preceding 7 nucleotides can be used as a first extracting sequence, and the following 7 nucleotides can be used as a second extracting sequence. More specifically, all sequence reads are verified for the two extracting sequences separated by 25 nucleotides, after which the sequence of 25 nucleotides is extracted and is determined as the minimal barcode sequence. Of course, also some of the other target nucleotide sequences derived from the mixed target nucleic acids might fulfill these criteria so that a wrong minimal barcode sequence is extracted. The chance that two given extracting sequences of 7 nucleotides long are separated by 25 nucleotides is 1 in 16807 (Table 4).

TABLE 4

Probability that a given extracting sequence, based on its length, when flanking either at one or both sides to the minimal barcode sequence, is found.

| Length extracting sequence | Probability of extracting sequence at one site | Probability of extracting sequence at both sites |
| --- | --- | --- |
| 1 | 1 | 1 |
| 2 | 16 | 32 |
| 3 | 81 | 243 |
| 4 | 256 | 1024 |
| 5 | 625 | 3125 |
| 6 | 1296 | 7776 |
| 7 | 2401 | 16807 |
| 8 | 4096 | 32768 |
| 9 | 6561 | 59049 |
| 10 | 10000 | 100000 |
| 15 | 50625 | 759375 |
| 20 | 160000 | 3200000 |
| 25 | 390625 | 9765625 |
| 30 | 810000 | 24300000 |
| 35 | 1500625 | 52521875 |
| 40 | 2560000 | 102400000 |
| 45 | 4100625 | 184528125 |
| 50 | 6250000 | 312500000 |

The probability of having these false positives decreases by increasing the length of the extraction sequence. In order to prevent such false positive, a longer extracting sequence is preferred (Table 4); the best one being the complete constant flanking sequence.

The finding of false minimal barcode sequences increases with the complexity with the other mixed target nucleic acids, and with decreasing sizes of the extracting sequences. The more complex (e.g. when transferable molecular identification barcodes are mixed with fragmented complete genomes versus target enrichment of one or a few genes) the mixed target nucleic acids, the higher the chance that certain fragments may fulfill the criteria of extracting sequences. Of course, in a mixture of nucleotide barcodes sequences and other target nucleotides sequences the target nucleotide sequences derived from the nucleotide barcode sequence can be first isolated through a nucleotide barcode sequence identifier sequence (might be identical to the extracting sequence), and in a second phase characterize/process the actual minimal barcode sequences in the isolated nucleotide barcode sequences only. In this way one might even prevent the extraction of false minimal barcode sequences, in case when smaller extracting sequences are used.

Since the extraction of a minimal barcode sequence may be based on the exact sequence of the extracting sequence(s), DNA synthesis, amplification and sequencing errors introduced in the constant flanking sequencing, more specifically in the extracting sequence region, will result in no exact match so that the minimal barcode sequence can therefore be not extracted. Here, the shorter the length of the extracting sequence, the lower the chance that amplification and/or sequencing errors will occur in the region of the extracting sequence. The quality of the sequenced bases in a sequence decreases to the end of a fragment, so that at the end of a sequenced fragment nucleotides with a low signal will be trimmed away. When genomic DNA under investigation, and therefore also nucleotide barcodes added to a sample, will be fragmented for preparation of a sequencing library (e.g. through ligation of adapters), the relative start and end of a sequencing fragment derived from a nucleotide barcode sequence varies. When the end is located in the minimal barcode sequence, the minimal barcode sequence is not completely sequenced and therefore can even not be determined. When the end of a sequence is located only a few nucleotides after the minimal barcode sequence, only a small part of the constant flanking sequence will be determined. When the length of the extracting sequence is larger than the sequence obtained at the end, the minimal nucleotide barcode sequence, although completely sequenced, one can also not determine the minimal barcode sequence since the extracting sequence is not recognized. This also means that the extracting sequences are best located immediately next to the minimal barcode sequences, i.e. immediate in preceding and following the minimal barcode sequence.

Thus, a too long extracting sequence might miss the identification of minimal barcode sequences because of amplification and sequencing errors, and/or bad quality of sequenced nucleotides. A too short extracting sequence might result in the finding of false positive minimal barcode sequences. In the end, a balance has to be found between both pitfalls, and thus in the length of extracting nucleotide sequence to be used.

Rather than determining the minimal nucleotide barcode sequence by its location in/between the left and right constant extracting sequences, one could also use only one constant extracting sequence. When the upstream extracting sequence is used, a given length downstream this extracting sequence is used to determine the minimal nucleotide barcode sequence, when the downstream extracting sequence is used, a given length upstream this extracting sequence is used to determine the minimal nucleotide barcode sequence. Indeed, in the above example of 7 nucleotide long upstream and 7 nucleotide long downstream extracting sequences to the minimal nucleotide barcode sequence, the same stringency/accuracy of specific analysis of sequenced sequences derived from nucleotide barcode sequences versus aspecific analysis of sequenced sequences from other nucleic acids in that sample under investigation, for the determination of minimal nucleotide barcode sequences is obtained when using only one (upstream or downstream) extracting sequence of 14 nucleotides long ($1/4^{14}=1/268435456$).

The place at which linearization is performed might also a means, even when the same amount/concentration of transferable molecular identification barcodes is used, of recovering more minimal nucleotide barcode sequences in a given sequencing experiment. For example, the ends of DNA fragments are less prone to fragmentation by sonication then internal fragments. When target sequencing templates are prepared by capturing, and the capturing oligo is located internal to the fragments, the read depth at the nucleotides to which the capturing oligo was directed, and its flanking sequences, will have a Gaussian distribution. When target sequencing templates are prepared by capturing, and the capturing oligo is located at the end of such fragments (e.g. because of linearization by a restriction enzyme), the read depth at the nucleotides to which the capturing oligo was directed, and its flanking sequences, will have no Gaussian distribution. A much higher read depth will thus be obtained starting from the linearization point, and if the minimal nucleotide barcode sequences are located close to this starting point, a higher number om minimal nucleotide sequences will be obtained for the same amount of nucleotide barcodes, and thus for the same amount of transferable molecular identification barcode.

Preferentially, the different minimal nucleotide barcode sequences in transferable molecular identification barcode have the same length (e.g. 25 nucleotides long). When all minimal nucleotide barcode sequences have the same length, their downstream (bio)-informatic processing is more simple. The minimal nucleotide barcode sequences in transferable molecular identification barcode may have, however, different lengths, allowing more complex applications, but also more complex downstream processing. If transferable molecular identification barcodes contain minimal nucleotide barcodes sequences with a different length, but if the smallest of them is still sufficient long to allow the generation of an unlimited number of different minimal molecular identification of barcodes, less complex (bio-) informatic processing might still be used by ignoring the nucleotides in the longer minimal molecular barcodes. For example, if transferable molecular identification barcodes contain minimal nucleotide barcodes of 25 nt and 30 nt long, one might analyze 25 nucleotides only (thus all nucleotides in the 25 nt minimal nucleotide barcode sequences and only the first 25 nucleotides in the 30 nt minimal nucleotide barcode sequences). In case that a mixture of nucleotide barcodes having minimal nucleotide barcode sequences of the same and different lengths are used, in which the length of the longer minimal nucleotide barcode sequences are trimmed away by (bio-)informatic means; from the moment that at least 2 of the minimal nucleotide barcode sequences have the same length only (parallel) sequencing can be used to discriminate and identify the minimal nucleotide barcode sequences having the same length.

Two different minimal nucleotide barcode sequences for the generation of transferable molecular identification barcodes are in theory different sequences when they only differ for a nucleotide at one nucleotide position. Most DNA synthesis, amplification and sequencing technologies used for the characterization of DNA sequences are, however, error prone. Highly parallel sequencing technologies have sequencing error rates of up to 0.1%-15%. If a given lot of transferable molecular identification barcodes is built from nucleotide barcodes, in which for example two minimal nucleotide barcode sequences only differ for a nucleotide at one nucleotide position, then one of these nucleotide barcode sequences can be erroneously typed as the other nucleotide barcode sequence because of a sequencing error at the nucleotide position for which the two minimal nucleotide barcode sequences differ so that the sequence of the other minimal nucleotide barcode sequence is wrongly concluded.

The different nucleotide barcodes that are used for the generation of a given lot of transferable molecular identification barcodes therefore need to be sufficient different in their minimal nucleotide barcode sequences, so that it is very unlikely that one nucleotide barcode sequence is converted to another nucleotide barcode sequence because of amplification and/or sequencing errors. If single stranded oligonucleotides, or double stranded constructs thereof, are used as described above as such, such distantly unrelated sequences should be designed right from the beginning before the actual synthesis of each oligonucleotide. When for example nucleotide barcode plasmids are used, nucleotide barcode plasmids that have sufficiently distantly unrelated sequences should be selected from the library of plasmids that carry all possible nucleotide barcode sequences.

Therefore, when for example, 60 nucleotide barcode plasmids are needed to produce a lot of 1 million transferable molecular identification barcodes, more than 60 plasmids will in practice be needed in order to be able to select from so that the best 60 plasmids that have sufficiently different sequences can be selected.

The selection of sequences that are most different can, for example, be obtained by phylogenetic analysis (De Bruyn et al., 2014). A phylogenetic tree is a branching diagram or tree showing the inferred relationship among a set of sequences based upon similarities and differences in their physical or genetic characteristics. From such phylogenetic trees, the sequences having the most genetic change or having the highest genetic distance can be selected.

Besides selecting nucleotide barcode sequences that are sufficiently different, sequences could be selected in which errors from amplification and/or sequencing errors can be corrected. This can be achieved through the use of error correcting algorithms and codes. Two popular sets of error-correcting codes are Hamming codes (Hamady et al., 2008) and Levenshtein codes (Buschmann and Bystrykh, 2013).

Nucleotide barcode sequences can thus be identified by highly parallel sequencing. If a transferable molecular identification barcode is built up of 6 nucleotide barcode sequences, sequencing should reveal those 6 nucleotide barcode sequences, as well as other sequences which deviate from these 6 nucleotide barcode sequences because of amplification and/or sequencing errors. When the number of times that each sequence is found is determined (e.g. in a histogram), the true 6 nucleotide barcode sequences will be found at a much higher frequency than the sequences with sequencing errors. A threshold level for frequency can be set for retaining or discarding nucleotide barcode sequences. The sequences with sequencing errors will be found at a lower frequency below the threshold level, so that they are neglected and discarded for further analysis for determining the nucleotide barcodes, and therefore transferable molecular identification barcodes, that are actually present, will be only concluded.

Of the available sequences, a small fraction of sequences is lost in the analysis because they carry amplification and/or sequencing errors. The output of number of sequence reads from highly parallel sequencing, however, is enormous so that still sufficient sequence reads will be obtained without amplification and sequencing errors, so that the actual nucleotide and transferable molecular identification barcodes can still be determined.

When the nucleotide barcode sequences for generating a lot of transferable molecular identification barcodes were selected that can be error-corrected, the sequences with sequencing errors can be possibly corrected by error-correcting algorithms, so that there is only a small loss of sequences because of amplification and/or sequencing errors.

But even if the nucleotide barcode sequences for generation of a given lot of transferable molecular identification barcodes were not selected with methods that would allow error correction, sequences with amplification and/or sequencing errors can still be recovered in the analysis. For example, if a sequence is observed at a low count, but has a neighboring sequence at a high count, it is most likely that the low count sequences have arisen through amplification and/or sequencing errors of a sequence with a high count based on the estimated mutation rate, then the count of the less abundant sequence can be attributed, converted and counted to the higher abundant neighboring sequence (Akmaev and Wang, 2004).

Figure 5:
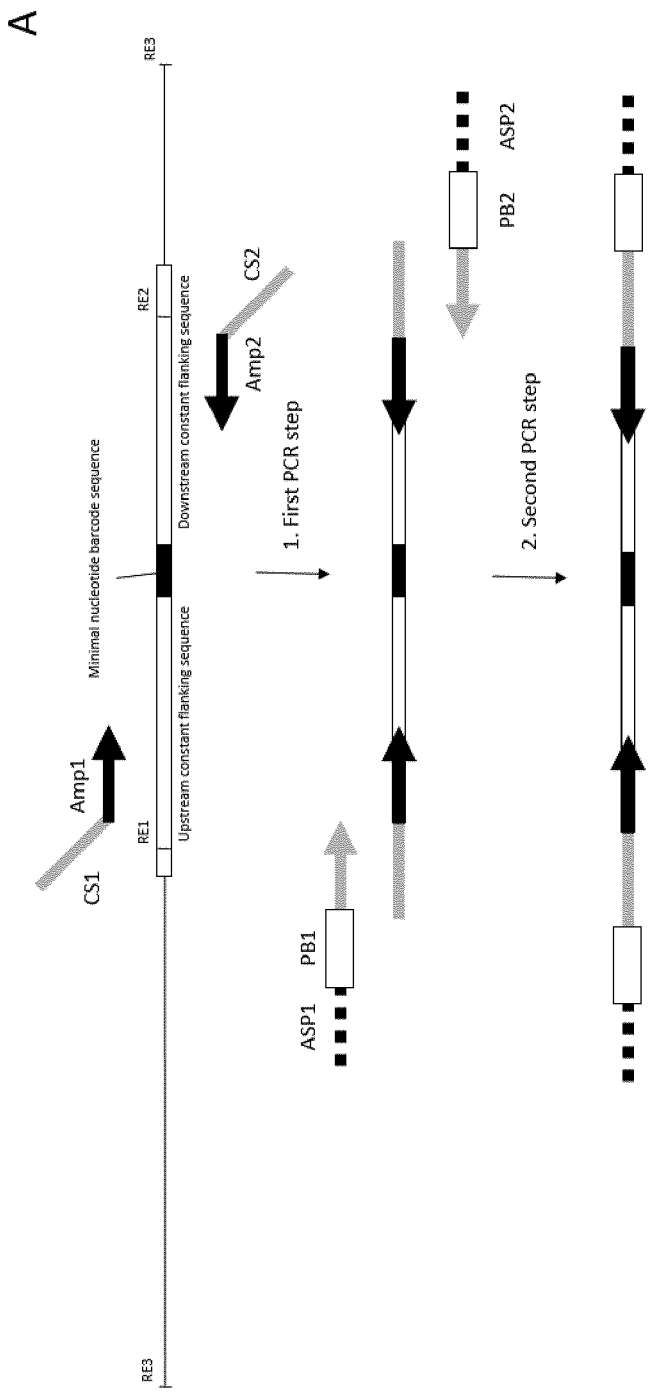
FIG. 5. Preparation of sequencing template from linearized nucleotide barcode plasmid for highly parallel sequencing: A. in a 2-step PCR protocol; B. in a primer-extension-ligation/PCR protocol; C. in a fragmented DNA ligation method followed by capturing by hybridization of the barcode nucleotide sequences.
Figure 5:
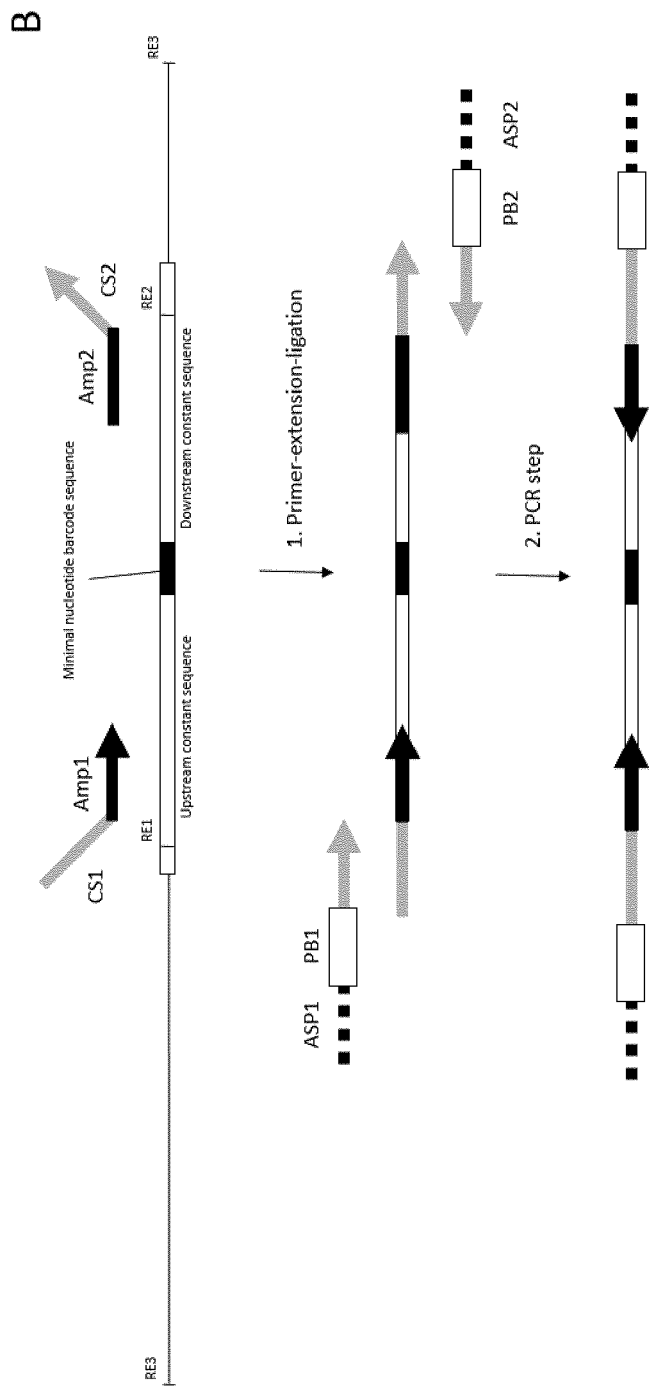
Figure 5:
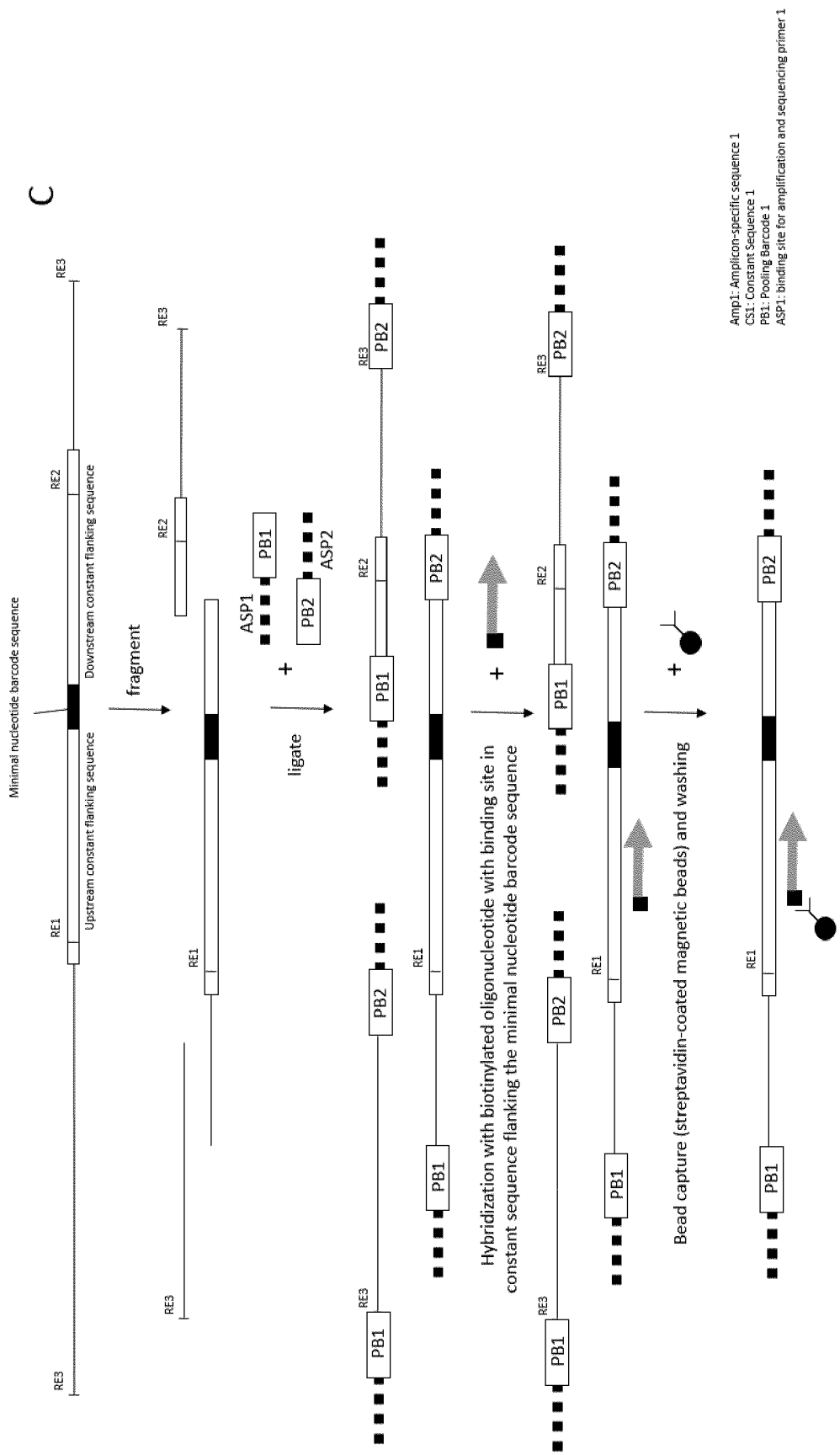

Nucleotide barcode plasmids that are used to produce a given lot of transferable molecular identification barcodes are optionally linearized after production and used in linearized form in practical applications. In this way, accidental replication of plasmids is prevented. Moreover, the use of transferable molecular identification barcodes build of linear nucleotide barcode sequences may be more efficient in applications of samples barcodes over circularized, possibly supercoiled, nucleotide barcode sequences. It is more economical to linearize the limited number of nucleotide barcode plasmids before mixing them to transferable molecular identification barcodes, rather than to linearize the huge number of transferable molecular identification barcodes that consist of nucleotide barcode mixes produced afterwards. Linearization of nucleotide barcode plasmids can be obtained by digestion with one or more restriction enzymes that cut at one or more sites in the plasmid, but outside the minimal nucleotide barcode sequence and its (partly) flanking nucleotides (FIG. 4). If plasmids would be only cut with one restriction enzyme that cuts at only one site in a plasmid, traces of plasmids that failed to be cut remain circular and present. This is prevented by using one or more restriction enzymes so that more than one site is cut in the plasmid. The chance that all sites fail to be cut in a single plasmid is then highly unlikely. Preferentially the restriction enzyme(s) is heat-inactivated after digestion. Indeed, when transferable molecular identification barcodes are used in genetic tests and mixed with genomic DNA, still active restriction enzyme could still digest the genomic DNA. When nucleotide barcode plasmids are cut at more than one site, different linear fragments will be obtained, of which only one fragment contains the actual minimal nucleotide barcode sequence. All digestion fragments of nucleotide barcode plasmids can be used as such in applications. Alternatively, only the digested fragment containing the minimal nucleotide barcode sequence might be isolated and used in applications. Preferentially the DNA concentration of the nucleotide barcodes molecules is determined, either before or after digestion, so that the nucleotide barcodes can be normalized to the same concentration so that transferable molecular identification barcodes are produced in which the different nucleotide barcodes are found at more equimolar levels. Restriction enzymes can be chosen so that the actual minimal nucleotide barcode is located in a large, medium or small sized fragment after digestion of the nucleotide barcode plasmid. For example, when transferable molecular identification barcodes will be used for labelling blood samples from which genomic DNA will be isolated to be used in genetic tests, the actual minimal nucleotide barcode sequence may be preferably located in a larger DNA fragment. Indeed, the genome of such a biological sample will be represented in larger genomic DNA fragments which might be more efficiently extracted with genomic DNA extraction kits. Smaller fragments might not be retained efficiently with such genomic DNA extraction kits since shorter fragments are considered as fragmented DNA that are eliminated in the DNA extraction protocol. When highly parallel sequencing technologies are used that generate longer sequence reads, such as by Real-Time SMRT® DNA sequencing and nanopore sequencing, the minimal barcode sequence is preferentially also located in a longer linearized fragment so that it is more compatible with these respective DNA sequence template preparations. When transferable molecular identification barcodes are used for labelling blood samples obtained from pregnant mothers for non-invasive prenatal testing (NI PT), for example for trisomy 21, fetal circulating DNA will be isolated. Since free circulating DNA is small sized fragmented DNA from the fetus, the minimal nucleotide barcode sequence may be preferentially located on a small digestion product so that they can be extracted together with the fetal DNA. The same considerations are needed for tests analyzing circulating tumor DNA. Also DNA obtained from formalin fixed paraffin embedded tissue (FFPE) contains rather small amplifiable sized DNA fragments, so that in this application the minimal nucleotide barcode sequence may be also preferentially located on a small digestion product so that they can be extracted together with FFPE DNA. Nucleotide barcode plasmids used to produce transferable molecular identification barcodes may thus be differentially digested on the basis of the application, so that a given lot of transferable molecular identification barcode is produced for a given set of applications, even one given application only. FIG. 5 show examples how molecular nucleotide sequences are prepared as templates for NGS sequencing.

An important application of transferable molecular identification barcodes is thus the labelling of biological samples on which genetic tests will be performed. Samples may come from or be in the initial form of one or more biological matter, e.g. blood, plasma, serum, urine, saliva, sputum, feces, mucosal excretions, tears, synovial fluid, cerebrospinal fluid, peritoneal fluid or other fluid. Samples may include cells, or may be free of cells. Transferable molecular identification barcodes allow absolute quality assurance of the genetic tests to prevent sample switching and contaminations. More specifically, sample switches and contaminations are not prevented, but transferable molecular identification barcodes enable them to be detected if they do occur. Preferably a transferable molecular identification barcode is added to the genetic test process as early as possible. The transferable molecular identification barcode sequences should be found at the end of the complete process, and this guarantees quality assurance. In this way the whole process is quality assured from the moment the transferable molecular identification barcode is added. The earliest possible moment would be when the specimen for analysis is collected, e.g. the transferable molecular identification barcode is already present in the collector tube (e.g. collecting tube for a blood sample). Apart from the quality-assurance, such transferable molecular identification barcodes allow automation of the laboratory and reporting protocols. Indeed, the sequencing apparatus not only reads a mutation in the target nucleotide acids under investigation, but also the name of the patient that carries this mutation to the added and associated transferable molecular identification barcodes to the sample, when the physical barcode on the item containing the transferable molecular identification barcode is linked to the LIMS system in which all information of a sample is stored.

The method may include a step of transporting the sample while it is contacted with transferable molecular identification barcodes from a site where the biological sample was taken to a clinical laboratory (e.g., one located at least 100 meters, 1000 meters, 10,000 meters, 100,000 meters from the site where the biological sample was taken) at which a sample analysis will occur. In this way the actual testing can be outsourced to a centralized lab without any problems, since a customer still keeps full control of the obtained data of his/her sample. When a customer receives the sequencing data of such a centralized lab, the customer knows which nucleotide barcode sequences should be present in the sequencing data of that sample, so that the customer is sure that he/she receives the data from his/her sample that were sent to the outsourced or centralized lab. The finding of any other nucleotide barcode sequences will conclude that the sequencing data are not from his/her sample, and/or that the sequencing data are contaminated with sequences from another sample.

Even before a DNA sample moves into sequencing, it can already be contaminated by DNA from another sample. In a study in which 217 complete genomes were sequenced, 7 samples (3.2%) were found to contain contaminating DNA (Taylor et al., 2015). In tests that only are looking for a mutation in a given fraction of DNA of the total DNA, such as circulating fetal or tumor DNA, such contaminations might negatively interfere with the test result and even result in a wrong test result. DNA extractions are often performed in automated systems, such as the Chemagic™ instrument (PerkinElmer), the QIAcube instrument (Qiagen). During DNA extraction, sample and/or processing tubes are open at certain moments or even open in such DNA extraction systems throughout the complete process. Solutions are transferred between, stirred in, these tubes and might generate aerosols which can contaminate between samples. All these processes are confined to a small chamber of the system isolated from the environment, even when not in use. When such systems are making use of a centrifuge, the aerosols are even spread in the confined chamber. Given the confined volume of the chamber, the fraction of contaminating aerosols can thus become much higher than in an open lab. Continuous use of these instruments over years can thus result in a gradual buildup of contaminating DNA in the confined chamber that might contaminate newly processed samples. Use of transferable molecular identification barcodes might thus allow one to quantify and score the quality of the extracted DNA samples. Especially in tests that analyze small fractions of target DNA, such as circulating fetal or tumor DNA, transferable molecular identification barcodes might in the end thus provide a quality score of the tested DNA and therefore a quality score for the total test.

Transferable molecular identification barcodes that are used in quality control or assurance applications require that the transferable molecular identification barcodes themselves are produced under the best quality assured conditions. Given the fact that only a small number of nucleotide barcode sequences are needed to produce up to 1 million, or more, unique transferable molecular identification barcodes, only a small number of tubes and/or plates containing these nucleotide barcode molecules need to be handled. Moreover, they can be easily labeled with a macroscopic paper 1D or 2D barcode label during production which can be identified by scanning during production. The preparation of tubes, or any recipient containers, with transferable molecular identification barcodes prepared from this small number of tubes and/or plates containing the nucleotide barcodes can be performed with a rather basic robotic system. When this complete production process is also connected to a LIMS system, the different recipient tubes or containers of transferable molecular identification barcodes can be produced with a very low risk of error.

The fact that, for example, 1 million different recipients with different transferable molecular identification barcodes are produced from a limited number of 60 nucleotide barcodes even allows quality testing of transferable molecular identification barcodes after production. Indeed, if in each lot of 1 million transferable molecular identification barcodes the production of all combinations of 1 million transferable molecular identification barcodes is performed in a fixed ordered predetermined process, one can select specific tubes of a complete lot or batch in order to verify if the expected nucleotide barcodes are present in the selected tubes, after which it then can be concluded that all the 60 nucleotide barcodes ended individually up in each of the expected 1 million different tubes or recipient containers.

Such a quality control after production would not be possible if a single nucleotide barcode sequence was used as a transferable molecular identification barcode, since quality control after production would then mean that every tube containing a single nucleotide barcode sequence should be tested in order to make sure that the correct nucleotide barcode sequence was present, which in turn would mean that each transferable molecular identification barcode container needs to be sacrificed and can therefore not be used anymore; if used, the transferable molecular identification barcode would then not be used once. By using a mixture of nucleotide barcodes to produce transferable molecular identification barcodes from a limited number of nucleotide barcodes, only a minimal number of transferable molecular identification barcode tubes or recipient containers thus need to be sacrificed for quality control. When 60 nucleotide barcodes are used for generating 1 million different soluble barcodes, even less than 60 transferable molecular identification barcode tubes or recipient containers need to be sacrificed since each container contains 6 nucleotide barcode sequences so that sacrificing 1 transferable molecular identification barcode container already provides information of 6 nucleotide barcode sequences. In practice, a lot of 1 million transferable molecular identification barcode tubes or recipient containers will not be produced in one time but in smaller number, e.g. 10.000 tubes per production round. A given number of transferable molecular identification barcodes containers will therefore likely be tested from each production round, so that the total number of tested transferable molecular identification barcodes for all production rounds combined will in practice exceed the number of 60, thereby further increasing redundancy and therefore better quality control testing of the produced transferable molecular identification barcodes. When for the production of 1 million transferable molecular identification barcode tubes or recipients, a total of 100 smaller lots of 100×100 transferable molecular identification barcodes are produced, and for each smaller lot 40 transferable molecular identification barcodes are verified after production, 4000 transferable molecular identification barcodes are then verified after production of the complete lot of 1 million transferable molecular identification barcodes. This is still a small fraction of all transferable molecular identification barcodes of the total lot that are only verified and sacrificed after production, in order to obtain a very complete and redundant quality control process of the production process of that lot of 1 million transferable molecular identification barcodes.

In this example, a set of 60 nucleotide barcodes thus allows the generation of 1 million transferable molecular identification barcodes that each are built up of 6 nucleotide barcodes. This also implies that each of the 60 nucleotide barcodes will be found in 100 transferable molecular identification barcodes. This also implies that any combination of 5 given nucleotide barcodes will be found in 100 transferable molecular identification barcodes, but each of the latter 100 transferable molecular identification barcodes will differ for the 6th nucleotide barcode. When a transferable molecular identification barcode needs to be characterized, for which amplification such as for example PCR is needed, a given nucleotide barcode in a transferable molecular identification barcode might not be amplified so that the corresponding target nucleotide sequence (amplicon) derived from that nucleotide barcode will not be found; a phenomenon which is known as amplicon dropout. If in the above example the 6th nucleotide barcode fails to be amplified and/or sequenced, so that only 5 nucleotide barcode sequences can be characterized, one might not be able to determine which one of the possible 100 transferable molecular identification barcodes was present. This potential problem applies for every nucleotide barcode, i.e. when a particular nucleotide barcode fails to be detected because of amplicon dropout, there are 100 potential transferable molecular identification barcodes for which it cannot be concluded which transferable molecular identification barcode was in fact present. The above described toleration of amplification and/or sequencing errors, such as the use of error correcting tools, cannot correct for amplicon-dropouts.

Failure to characterize and identify the exact transferable molecular identification barcode because of an amplicon-dropout can be circumvented by working with pairs of nucleotide barcodes, instead of single nucleotide barcodes to produce transferable molecular identification barcode mixes, making the system more redundant. When one nucleotide barcode of a pair of nucleotide barcodes fails to be amplified and/or sequenced, the other nucleotide barcode of that given pair might still be characterized and identified. Finding either one of the nucleotide barcodes of a given pair of nucleotide barcodes, or both nucleotide barcodes of that given pair of nucleotide barcodes allows one to determine unequivocally which of the pair of nucleotide barcodes was present. For the generation of 1 million unique sample barcodes, which each are built up of 6 pairs of nucleotide barcodes (12 nucleotide barcodes in total), one needs 120 nucleotide barcodes to build a complete lot of 1 million different unique transferable molecular identification barcodes (see Table 5). For the generation of 1 million transferable molecular identification barcodes, using and preparing 120 nucleotide barcodes (i.e. plasmid preps) is hardly a significant additional effort compared to the effort needed when 60 nucleotide barcodes need to be prepared.

TABLE 5

Number of different transferable molecular identification barcodes that can be prepared in function of the number of nucleotide barcode pairs used per transferable molecular identification barcode.

| Different nucleotide barcode pairs per transferable molecular identification barcode (a) | Number of nucleotide barcode pairs needed | Number of different transferable molecular identification barcodes |
|---|---|---|
| 2 | 40 | 100 |
| 3 | 60 | 1000 |
| 4 | 80 | 10000 |
| 5 | 100 | 100000 |
| 6 | 120 | 1000000 |
| 7 | 140 | 10000000 |
| 8 | 160 | 100000000 |
| 9 | 180 | 1000000000 |
| 10 | 200 | 10000000000 |
| 15 | 300 | 1000000000000000 |
| 20 | 400 | 100000000000000000000 |
| 25 | 500 | 1000000000000000000000000 |

(a) Sets of 10 pairs of nucleotide barcodes are used; for each nucleotide barcode pair, one can choose between 10 nucleotide barcode pairs An additional advantage of using pairs of nucleotide barcode sequences is that a contamination can be concluded with much higher, to even complete, certainty. Indeed, when very low contaminations are present and found, the finding of both minimal nucleotide barcode sequences of nucleotide barcode sequence pairs confirm each other in detecting the contamination.

Since sample switches will result in a high proportion of unexpected nucleotide barcodes (and disappearance of expected nucleotide barcodes which should be present at a higher proportion), and a contamination typically results in a much smaller proportion of unexpected nucleotide barcodes than the expected nucleotide barcodes, informatic pipelines could be programmed so that the nucleotide barcodes found at a high proportion are analyzed in a 'non-pair mode' so that amplicon dropouts can be detected, while nucleotide barcodes found at a low proportion are analyzed in a pair-mode so that both minimal nucleotide barcode sequence of a nucleotide barcode pair need to be detected to conclude a contamination.

Rather than working with pairs of nucleotide barcodes, one might even use triple, quadruple combinations, or more, of nucleotide barcodes sequences, in order to make the system even more redundant and robust.

When nucleotide barcode plasmid preps are used from a $N_x$ random library, the nucleotide barcodes need to be first sequenced in order to identify the minimal nucleotide barcode sequences. The amplification and sequencing step of individual nucleotide barcodes will in fact already be a first selection step for obtaining suitable nucleotide barcodes for the production of transferable molecular identification barcodes, over nucleotide barcodes that might be difficult to amplify and/or sequenced and which could result in amplicon dropouts when the transferable molecular identification barcodes are characterized in applications.

For nucleotide barcodes that pass this selection criterion, even further selection criteria could be used. For example, nucleotide barcode sequences that are picked up and characterized as having a high GC and/or AT content might not be included for further production of transferable molecular identification barcodes. Indeed, it is known that such sequences are difficult, or fail, to be amplified and may result in amplicon dropout and/or fail to be sequenced. While a given nucleotide barcode already might have passed an amplification and/or sequencing control step during the first criterion described above, it might have only done so because it was present in a homogeneous DNA prep containing only one nucleotide barcode at a high concentration, which is not the case anymore when practically used in applications where it is combined with other nucleotide barcodes and/or used at lower concentrations. In its latter true environment of the applications, a given nucleotide barcode might still fail to be amplified and/or sequenced.

Other selection criteria against certain nucleotide barcode sequences for the production of transferable molecular identification barcodes might be sequences carrying stretches of identical nucleotides, such as, for example, a row of identical nucleotides (6, 7, or more; or even 5, 4, 3 or 2). Indeed, certain highly parallel sequencing technologies that might be used for the characterization of nucleotide barcodes in transferable molecular identification barcodes, such as pyrosequencing and ion semiconductor sequencing, the exact number of nucleotides in a stretch of identical nucleotides cannot always be correctly determined. Although such sequences might generate more than 1 type of sequence, i.e. sequences with sequencing errors, which can be corrected as described above, it might be preferred not to include such nucleotide barcodes in a lot for the production of transferable molecular identification barcodes if this can be done at a minimal effort by picking some additional nucleotide barcodes for the generation of a pool of nucleotide barcodes to select the most nucleotide barcodes from.

Any transferable molecular identification barcode will be only used once for labelling an item or sample, so that each item or sample is uniquely labelled, in order to obtain a watertight quality assured labelling system. Once that 1,000,000 transferable molecular identification barcode tubes or recipient containers have been produced, it is only a minimal effort to select and prepare 120 new nucleotide barcode plasmid preps for the production of the next lot of transferable molecular identification barcodes.

Every transferable molecular identification barcode also needs to get an identification name or code that will be used in downstream processing, which will be stored in a database. This database is optionally located at a central location and can be accessed cloud-based. When a given lot contains 1,000,000 transferable molecular identification barcodes, this database will contain 1 million different rows and will thus be rather large. Very likely, software programs (such as algorithms) will be used in downstream processing. The actual nucleotide barcode sequences or transferable molecular identification barcodes then need to be processed with these software programs and/or linked to these databases. For this purpose, for example, for each lot number a file (such as a txt.file, a csv.file) listing the 120 names and minimal nucleotide barcode sequences of the nucleotide barcodes could be generated. Since that all 1,000,000 transferable molecular identification barcodes of a given lot will be produced in the same fixed predetermined order, the 12 nucleotide barcode sequences in any transferable molecular identification barcode can be deduced by a software algorithm, using this small file which carries that given lot number in its filename and listing the 120 names and minimal nucleotide barcode sequences of the nucleotide barcodes that were used for the production of that lot number of transferable molecular identification barcodes in the same predetermined order. Such a smaller database with 120 rows, in combination with an algorithm which can deduce the actual minimal nucleotide barcode sequences present in each of the 1,000,000 transferable molecular identification barcodes, will be more practical than generating and using for each lot a table of 1 million rows in which each row describes the 12 molecular nucleotide barcodes in each of the 1 million transferable molecular identification barcodes. Instead of using one table per lot, one single table (such as a txt.file, a csv.file) listing all minimal nucleotide barcode sequences used in all lot numbers might be used. Such a single table requires then a third column, besides the columns listing the names and respective minimal nucleotide barcode sequences, which describes the respective lot number in which each of the minimal nucleotide barcode sequences are used. Even additional columns, such as adapter information (e.g. nucleotide barcode sequence identifier sequences, extracting sequences) in the constant flanking sequences might be added. Even when the information of lot numbers (generating extra rows and an extra column in the table), and possibly additional information (generating extra columns in the table), is combined in a single table, this single table is still much smaller than tables listing all transferable molecular identification barcodes and their associated minimal nucleotide barcode sequences.

If one needs to select, for example, 120 nucleotide barcodes that have the most different minimal nucleotide barcode sequences and therefore most unrelated sequences, one needs a larger number of nucleotide barcodes to select from. The larger the number of minimal nucleotide barcode sequences from which one can select, the more perfect optimal unrelated sequences can be selected. However, the gain in selecting the most unrelated sequences decreases when more sequences are added to the pool of minimal nucleotide barcode sequences to select from. A simulation analysis, which is based on Manhattan distance, m-medoid clustering, for selection of 120 minimal nucleotide barcode sequences that are 25 nucleotides long that differ as much as possible in sequence for the production of a given lot of 1 million transferable molecular identification barcodes each built up of 12 nucleotide barcodes, concluded that about 400 nucleotide barcodes would be practically needed to select from. Adding additional minimal nucleotide barcode sequences to the pool to select from did result in hardly any further improvement in obtaining the most optimal unrelated sequences.

The preparation of 400 nucleotide barcodes, rather than 120 nucleotide barcodes is still a limited effort for the production of about 1 million unique transferable molecular identification barcodes, especially since this extra effort is only needed for the production of the very first lot of 1 million transferable molecular identification barcodes. Indeed, if 1 million transferable molecular identification barcodes have been produced, a next lot of 1 million transferable molecular identification barcodes needs to be produced. The same 120 nucleotide barcodes that were used for the production of the first production lot can be produced for the second lot of 1 million samples barcodes. This is, however, not preferred since identical transferable molecular identification barcodes will then be produced across different lots and used more than once. Even if the same nucleotide barcodes would be produced for the production of a second lot, their preps used for the production in the previous lot are most likely exhausted, so that new plasmid preps need to be prepared anyway. For the production of a new lot of transferable molecular identification barcodes, 120 new nucleotide barcodes are preferred. The additional effort of performing plate colony of the bacterial glycerol stock and colony picking is thus minimal. Moreover, for the production of a new lot of transferable molecular identification barcodes with new nucleotide barcodes, 400 new nucleotide barcodes will not be needed. Only 120 new nucleotide barcodes will be needed which will be added to the 280 nucleotide barcodes plasmids that were not selected for the production of the previous lot of nucleotide barcodes. From these 280+120 nucleotide barcodes, again the 120 mostly unrelated nucleotides barcodes will be selected for the production of a new lot of transferable molecular identification barcodes, and so on.

Parallel sequencing processing methods of transferable molecular identification barcodes, possibly combined with other target nucleic acids, is conditional in order to obtain absolute quality control. This in contrast to Sanger sequencing, which only sequences one type of sequence. Sanger sequencing of each nucleotide barcode, and possibly (each of) the other target nucleic acid(s) such as one or more exons of one or more genes, will require separate sequencing reactions. Splitting up different single Sanger sequencing is not guaranteed to be performed correctly, especially if many transferable molecular identification barcodes and/or samples are processed simultaneously. Indeed, at the end, the different split Sanger sequencing processes, or the obtained characterized data thereof, need to be combined again. Since each Sanger sequencing reaction also needs enrichment of the sequencing template, such as PCR, the initiation of the split processes already starts at a much earlier moment in the complete process than the actual sequencing, so that even many more steps are involved in each split process at which a switch and contamination errors can occur. If the splitting in processes was not performed correctly, then a wrong recombined process and/or result will be obtained.

In our example where 1 million different transferable molecular identification barcodes are built from 60 different nucleotide barcodes, every nucleotide barcode sequence will be found in 100 transferable molecular identification barcodes of that lot. When a non-parallel sequencing method is used for characterization of these transferable molecular identification barcodes, a switch between split processes can in the end, after combining the results of the different split sequencing reactions, result in a valid combination of nucleotide barcode sequences and therefore valid transferable molecular identification barcode, but a transferable molecular identification barcode that is not correct.

On the other hand, the transferable molecular identification barcodes described here and used in parallel sequencing processing methods still allow the splitting up of certain processes in the overall process, and still obtain absolute quality control. The split-up processes, however, need to have in turn (the same) parallel processing features (e.g. multiplex format) and have one feature in common (minimal barcode sequence). For example, the Ion AmpliSeq™ Exome assay (ThermoFisher Scientific) uses about 300,000 primer pairs across 12 primer pools. Several GeneRead DNAseq Targeted assays (Qiagen) use more than 2,000 primer pairs across 4 primer pools. Each of these split pools are still complex multiplex amplifications and have thus still a parallel nature. When to each of these pools 2 primers are added for enrichment of nucleotide barcodes, and when transferable molecular identification barcodes, built up of 6 nucleotide barcodes, were present in the original biological sample, a test result is valid if only all expected 6 nucleotide barcode sequences are found at the end. When one or more multiplex reactions in a given set of multiplex reactions for an assay are switched between different biological samples that are processed, more than 6 expected nucleotide barcode sequences will be found, so that the test can be marked as not valid. If in an assay that uses a pool of 4 multiplex amplifications, one multiplex was switched between different biological samples that do not share any nucleotide barcodes in their transferable molecular identification barcodes, the expected 6 nucleotide barcodes will represent about 75% of all obtained nucleotide barcodes sequences, while up to 6 additional nucleotide barcodes will represent about 25% of all obtained nucleotide barcode sequences. After the amplification enrichment step (before sequencing), the up to expected 6 nucleotide barcode sequences will not be found in that switched pool, but the up to non-expected 6 nucleotide barcodes sequences will represent 100% in that switched pool. Since that before sequencing all 4 pools are equally mixed, in which in the 3 non-switched pools the expected 6 nucleotide barcodes are present at a 100% fraction each, the overall up to non-expected 6 nucleotide barcodes will represent about 25% in the end. Such a switch of a single pool cannot be discriminated from a more overall contamination of the total sample, such as a DNA contamination of about 25% of one sample with another sample. In that case, in all 4 amplification enrichment pools the up to non-expected 6 nucleotide barcodes will represent about 25%, hence also at about 25% when all 4 amplification enrichment pools are combined before sequencing. When an NGS assay only uses 2 pools, a switch of a single pool between two biological samples that do not share any nucleotide barcode in their transferable molecular identification barcodes, both the expected and non-expected nucleotide barcodes will represent about 50% of all nucleotide barcode sequence reads. The more pools that are used in a given overall assay, the less sensitive a contamination detection becomes, possibly to an extent were molecular nucleotide barcodes do not guarantee absolute quality control anymore with respect to contamination detection. This can be overcome by proportional higher enrichment, and therefore relative deeper sequencing of the nucleotide barcodes over the other nucleic acid target sequences.

Figure 6:
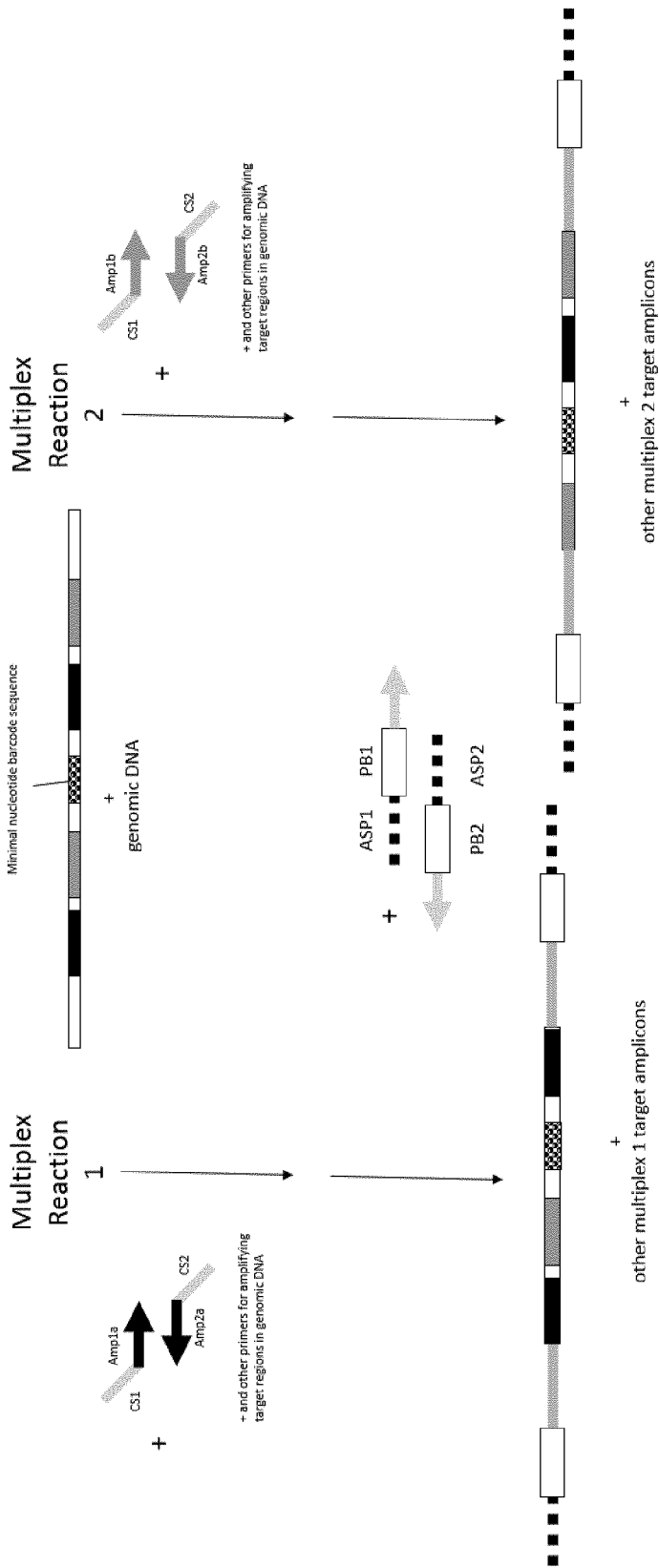
FIG. 6. Use of transferable nucleotide barcodes in an assay that uses split multiplex reactions. In this example, two split multiplex reactions are performed. At least one of the two primers directed to the nucleotide barcode sequences added to each of the multiplex PCR reactions have a different primer binding site in the flanking sequence(s) to the minimal barcode sequence. The nucleotide barcode amplicons obtained in each multiplex reaction have a different length and/or flanking sequence composition in one or both flanking sequences to the minimal barcode region, so that their origin can be determined. When the expected barcode is observed at the end of the assay, and both amplicons with correct lengths and/or flanking sequence compositions are observed, no sample switch did occur between samples and between split reactions. When the expected barcode is not observed at all, both multiplexes where switched with two multiplexes of another sample. When besides the expected barcode, another barcode is observed, but the expected barcode is observed in an amplicon with the expected length and/or flanking sequence composition of one multiplex only, but the non-expected barcode is observed in an amplicon with the correct length and/or flanking sequence composition of the second multiplex only, only the second multiplex was switched with a second multiplex of another sample.

This can be also overcome when for assays that use different pools for target enrichment, to each of the pools not the same two primers are added for enrichment of the nucleotide barcode. The actual minimal nucleotide barcodes sequences are flanked by constant sequences. In a multiplex amplification assay, by targeting one or both primers that are added to a given pool to a different binding site in the flanking constant sequences, each of the nucleotide barcode sequences derived from each pool will have its given characteristic given different length of flanking sequences, and/or sequence context (FIG. 6). When at the end of an NGS test that uses 4 primer enrichment pools, the given 6 nucleotide barcode sequences are found, and when all expected 4 types of flanking sequences are found in all these nucleotide barcode sequences, it can be concluded that the expected 6 nucleotide barcodes were indeed present in each of the 4 split pools, so that a switch of single pools between different samples can be also excluded. One of the two primers used in a given pool might be even shared between different pools. It is the given combination of primers that will determine the extent of combined flanking sequences that will be enriched in a given pool from which it can be discriminated from other pools.

This format will not only allow more sensitive contamination detection in NGS assays that use primer pools for target enrichment, but allow discrimination between a switch of one or more pools in a split testing process between different samples only from an overall contamination in the total DNA sample.

Transferable molecular identification barcodes can be added to a solid substrate or container, such as the collection substrates of kits used for sample collection in medical and forensic applications. Or even better, transferable molecular identification barcodes are already produced in such collection containers. The transferable molecular identification barcodes can be added directly to a component of the kit which is suitable for receiving a nucleic acid sequence. This component is generally the same as or similar to a component that will also receive the unknown DNA sample that is being analyzed. The transferable molecular identification barcodes can be applied as an aqueous solution, powder, gel, resin, laminate, spray or in a form such as a capsule, trapped in a zeolite, or in any other suitable form. Of course, when not applied as an aqueous solution, the nucleotide barcodes are at a given moment not soluble. They become however again soluble and transferable during processing. Transferable molecular identification barcodes may also be coated or spotted onto the walls of a collection container, or impregnated into a swab or other component of a kit. For example, transferable molecular identification barcodes may be added to a vessel such as the Vacutainer® used for blood collection (Becton Dickinson), to a microtube, to the wells in a microtiterplate. Transferable molecular identification barcodes may be also spotted on a card, such as a FTA™ classic card manufactured by Whatman PLC. Kits of this type include FTA™ paper to which the transferable molecular identification barcodes may be added, either during manufacturing or subsequently when used for sample collection. Analogously it may be spotted on Guthrie cards. The substrates and containers mentioned in this paragraph are referred to as "carrier(s)"

The transferable molecular identification barcodes can be combined with agents or processes used in sample preparation, storage or processing, such as (a) solution(s) containing (a) stabilization(s), preservative(s), detergent(s), neutralizing agent(s), inhibiting agent(s), reducing agent(s), quenching agent(s), or a combination thereof. These components might have their affect through a direct (primary) interaction with the biological sample, such as the nucleic acids thereof, or with secondary products that are the result of this primary interaction, or even with more downstream interactions such as (a) component(s) generated because of secondary or tertiary interactions.

For example, such a compound could be an anticoagulant selected from the group consisting of heparin, ethylenediamine tetraacetic acid (EDTA), citrate, oxalate, heparin and any combination thereof, that prevent clotting of whole blood cells, which is thought to reduce DNA release from leukocyte cell populations.

For example, such a compound could be a nuclease inhibitor selected from the group consisting of diethyl pyrocarbonate, ethanol, aurintricarboxylic acid (ATA), formamide, vanadyl-ribonucleoside complexes, macaloid, 2-amino-2-hydroxymethyl-propane-1,3-diol (TRIS), ethylenediamine tetraacetic acid (EDTA), proteinase K, heparin, hydroxylamine-oxygen-cupric ion, bentonite, ammonium sulfate, dithiothreitol (DTT), beta-mercaptoethanol, cysteine, dithioerythritol, tris(2-carboxyethyl) phosphene hydrochloride, a divalent cation such as $Mg^{+2}$, $Mn^{+2}$, $Zn^{+2}$, $Fe^{+2}$, $Ca^{+2}$, $Cu^{+2}$, and any combination thereof.

For example, such a compound could be a formaldehyde releaser preservative agent such as one selected from the group consisting of: diazolidinyl urea, imidazolidinyl urea, dimethoylol-5,5-dimethylhydantoin, dimethylol urea, 2-bromo-2.-nitropropane-1,3-diol, oxazolidines, sodium hydroxymethyl glycinate, 5-hydroxymethoxymethyl-1-1 aza-3,7-dioxabicyclo[3.3.0]octane, 5-hydroxymethyl-1-1 aza-3,7dioxabicyclo[3.3.0]octane, 5-hydroxypoly[methyleneoxy]methyl-1-1 aza-3,7dioxabicyclo[3.3.0]octane, quaternary adamantine and any combination thereof, may be used (U.S. Pat. No. 5,459,073). Formaldehyde is often used to stabilize cell membranes and its use could therefore reduce cell lysis. Formaldehyde has also been thought to inhibit DNase and RNase thereby increasing the preservation and stability of the cell-free nucleic acids.

For example, a quenching compound could be a compound that includes at least one functional group capable of reacting with an electron deficient functional group of formaldehyde (e.g., an amine compound that reacts with formaldehyde to form methylol and/or imine Schiff base, or a cis-diol compound that reacts with formaldehyde to form a cyclic acetal). Such a quenching compound could be an ingredient selected from amino acids, alkyl amines, polyamines, primary amines, secondary amines, ammonium salts, or a combination thereof. More specifically selected from glycine, lysine, ethylene diamine, arginine, urea, adinine, guanine, cytosine, thymine, spermidine, or any combination thereof. Such a quenching compound is useful in removing any free formaldehyde.

Transferable molecular identification barcodes may be added to a combination of a preservative agent, an anticoagulant, and a quenching compound.

Again here transferable molecular identification barcodes may be already produced in collection containers that contain the stabilizing solution. For example, transferable molecular identification barcodes may be produced in a Cell-Free DNA BCT® blood collection tube used for collecting blood samples in which nucleated blood cells of the samples are stabilized and that are used in tests analyzing circulating fetal or tumor DNA (Streck or CFGenome), a PAXgene Blood ccfDNA tube (PreAnalytiX), a PAXgene Blood RNA collecting tube (PreAnalytiX) in which the RNA is stabilized, an Oragene-DNA saliva collecting system in which DNA of saliva is stabilized (DNA Genotek Inc.), and so on.

Together with transferable molecular identification barcode, other molecules for quality purposes other than detecting sample switches and/or contaminations, might be present. The carrier containing transferable molecular identification barcode may also contain, for example trisomy controls (e.g. Trizo21 from CFGenome) for testing for trisomy's in NI PT tests, for example Spike-in RNA Variant (SIRV) controls used in RNA tests (Lexogen)

A container or recipient that contains transferable molecular identification barcodes has preferentially a unique optical macroscopic 1D or 2D barcode paper label attached with a code that is one to one linked to the actual transferable molecular identification barcode and therefore also nucleotide barcode sequences thereof. For practical reasons, the actual sequence of, for example, twelve 25-nucleotide long sequences cannot be printed on a smaller paper label. Apart from this practical reason, it might be of interest that the person who is processing the samples, at least during certain phases of the process, is blinded from this information so that the transferable molecular identification barcodes are used in an unbiased process. Such a format leaves ample room for manipulation of the samples and the processes thereof. Only at the very end of the process the actual sequences of the nucleotide barcodes are needed for interpretation, validation of that process.

The attached optical macroscopic barcode label could have different formats. The label may be, for example, perforated, may be removable, may be printed in two (partly) identical parts of which one part is removable. A label that can be removed can then be placed on the patient's sample container or recipient at the time the sample is collected, in case a sample container is used that still does not contain the transferable molecular identification barcodes.

One could think of different protocols by which the information of the actual sequences of the transferable molecular identification barcodes is transferred from the production site to an application (customer) site. A possible way is that the customer should at some moment contact a server through the cloud, most likely located at the entity that also produces the transferable molecular identification barcodes. Preferentially, the transferable molecular identification barcodes, and therefore associated nucleotide barcode sequences are secured in the cloud and during data transfer, for example according to the OWASP (The Open Web Application Security Project) recommendations. Possibly they should be also compliant with the HIPAA (Health Insurance Portability and Accountability Act) legislation that provides data privacy and security provisions for safeguarding medical information. It should however be noted that, given the properties of the transferable molecular identification barcode system described above, patient privacy information is already guaranteed, since the transferable molecular identification barcode server does not need any patient information or local customer (e.g. hospital) code or information. For example, only the obtained nucleotide barcode sequences obtained at the customer site, as well as the paper identification code that the customer received are transferred from customer site to the transferable molecular identification barcode production and/or management site or company for verification in the central nucleotide barcode database, after which the transferable molecular identification barcode production and/or management site sends information back to the customer if there is a match between the paper code and the obtained nucleotide sequence reads, or not. Or either the obtained paper identification code is sent by the customer to the transferable molecular identification barcode production and/or management site or company, after which the production site does sent, for example, the actual minimal nucleotide barcode sequences associated with that paper identification code to the customer in which the determination of the presence of a match, or not, is performed at the customer site. The patient information, patient code at customer site, and the association with a transferable molecular identification barcode remains thus exclusively at the customer site, such as a hospital.

Obtaining such information from a cloud server could be free or restricted. The optical macroscopic barcode label on the tube provides sufficient information for the server to provide the correct transferable molecular identification barcode sequences. This code could already be sufficient for obtaining access to such a cloud server. However, an additional code, again a unique code for every transferable molecular identification barcode, might be given to a customer and required in order to gain access, so that an additional security level for obtaining the actual sequences of transferable molecular identification barcodes is in place. Indeed, since every lot of transferable molecular identification barcodes is built of a limited number of nucleotide barcode sequences which are produced and coded in the same fixed predetermined protocol for each lot, it would be possible when a given number of transferable molecular identification barcodes and the associated code names from a lot were used and therefore known to a given customer to determine the sequences of any transferable molecular identification barcode of that given lot. With such an additional code, a customer request can be indeed identified as requested by the holder and owner of the given macroscopic barcode label and transferable molecular identification barcode (combination).

Rather than obtaining the information of the sequences of the nucleotide barcodes of the transferable molecular identification barcodes on request on a list one by one, another option would be to obtain from the cloud server all the different sequences of the nucleotide barcodes and their associated names that were used for production of that given lot from which the transferable molecular identification barcodes originate. Indeed, given the fact that each lot of transferable molecular identification barcodes is built from a small number of individual nucleotide barcode molecules in a fixed predetermined protocol in a fixed order, including the naming of the containers containing each transferable molecular identification barcode, an algorithm, customized to this predetermined protocol, possibly in, or part of, a software package, could be also provided to the user. This algorithm, in combination with a file (e.g. a csv or txt file) containing the sequences of the nucleotide barcodes and their linked names for a given lot, can then be used by the customer to obtain the actual sequence of the nucleotide barcodes of a given transferable molecular identification barcode. However, a customer would then be also able to deduce the sequences of the nucleotide barcodes of all transferable molecular identification barcodes of that same lot. Of course, providing the sequences of additional nucleotide barcode or transferable molecular identification barcodes that were not used for that sample provides a less secured format platform since anybody skilled in the art can then easily deduce the sequences that are present in a given container containing a transferable molecular identification barcode on the basis of the optical macroscopic barcode label that is attached to that transferable molecular identification barcode container.

Different software tools could thus be developed for use of transferable molecular identification barcodes, either as a standalone tool to be used by a customer, are part of cloud server tool, in which information of single transferable molecular identification barcodes is obtained only, information of some or all transferable molecular identification barcodes of a given transferable molecular identification barcode lot is obtained, or even information of all transferable molecular identification barcodes of all lots of transferable molecular identification barcodes are obtained. Having information of transferable molecular identification barcodes that is actually not used in a given sample might indeed be of interest in certain applications. An example of such an application is the detection of a contamination. When transferable molecular identification barcodes codes are used which are built of 12 barcode sequences, the identification of additional barcode sequences would allow a software tool to detect and report a contamination. When a sample is contaminated by another sample, which for example do not share any of the 12 nucleotide barcode sequences, and if the contamination is less or more than 50%, the additional barcodes belonging to each of the transferable molecular identification barcodes can be determined. For example, if additional barcodes are found at a frequency of about 1% compared to the other nucleotide barcodes, these will very likely belong to the contaminating transferable molecular identification barcode. The proportion by which the nucleotide barcodes are observed thus provide additional information about the degree of contamination. In practice two different transferable molecular identification barcodes might share some nucleotide barcodes. Indeed, two different transferable molecular identification barcodes are unique and different if they share all but one minimal barcode sequence. A contamination is then only detected through the non-shared minimal barcode sequence. The customer might thus be interested in the source of contamination, in order to improve the processing of their samples and assay so that such contaminations do not occur anymore in the future. Another software tool could provide information about the contaminated sequences, even if the sequences are observed to be part of a different lot. For this purpose, a customer should than be able to obtain the sequences of transferable molecular identification barcodes not used for that respective sample, or maybe not used in any sample of that customer and therefore an external source of contamination is involved.

When an item or biological sample container is only labelled with a label at the outside of the sample, for example, with a paper label on a blood collector tube for forensic analysis purposes or a urine collector container for doping analysis purposes, on the outside wall of the collector container, the label can be easily manipulated, such as removal of the label, or even replacement with another label. This has led to a concern on the part of those who provide the samples that errors or malicious intent could lead to their samples being mishandled, thus implicating them in fraud or criminal activity. While even DNA in a biological sample for forensic analysis serves as an individual identification of the donor, it says nothing of the way and when the sample was obtained. Such an 'inside'-labelling would be extremely valuable in forensic, paternity, doping tests, and so on, after which manipulation of the label is much more difficult or even not possible anymore. The 'inside'-label even does need not to be determined at the time of the test itself, such as in a doping test were the actual doping test is a different test than the test that would detect the 'inside'-label, and were the Inside-label is only determined in cases where there are doubts. In cases when sample test result is questioned, even much later than the actual test was performed, such as before a court, regarding the way and/or when the sample was taken and transported, one could go back to test the identity of the 'inside label'.

Optional two different molecular identification barcodes can be added, even at the same moment, even providing further security measures. For example, a molecular identification barcode present in the recipient and which represents the party isolating the sample, and an extra molecular identification barcode representing the person that provided the biological sample in the recipient, is used. This could be of high interest when molecular identification barcodes are added to samples used for doping testing, in which the sportsman/woman owns also molecular identification barcode (e.g. as a solution in a tube) which he/she adds to his/her isolated biological sample at the moment that he/she provides it. In this way, transferable molecular identification barcodes are used as a (molecular) signature tool in which a sportsman/woman signs her/his taken biological sample with his/her signature and thus approval, being it a signature in the form of a molecular identification barcode.

Different types of information, or combinations of different types of information, can be assigned to transferable molecular identification barcodes: for example, information of an individual, patient, doctor, customer, hospital, provider; telephone number, email address, spatial information (location at which the transferable molecular identification barcode was added to an item), time (time at which a transferable molecular identification barcode was added to an item), sample type (blood, saliva, urine, stool), test ordered, test identification.

Transferable molecular identification barcodes can be also assigned to a processing pipeline to be used for analyzing the target nucleic acids, such as a bioinformatic processing pipeline for a DNA or RNA based test and trigger even automatic (bio-informatic) protocols. Bio-informatic analysis of whole genomes takes, even with high capacity hardware, hours of CPU time per sample and is thus very time-consuming. With the development of smaller quicker sequencing systems there are many applications in which not the whole genome is analyzed but only target regions such as a single gene or set of genes. Bio-informatic analysis of smaller target regions is less demanding. However, in a typical eukaryotic genome there are at least 20.000 different genes. One therefore needs to specify to which gene the obtained sequencing reads should be analyzed. When transferable molecular identification barcodes are assigned to each of these genes, the bio-informatic pipeline becomes even more automated because the system will then read also the information of target DNA, such as a gene or set of genes, that needs to be analyzed. In essence, DNA transferable molecular identification barcodes become then what one could call DNAware which is needed besides the sequencing hardware and software. Especially when NGS sequencers become more miniaturized and in the end becomes small hardware that needs to be stuck into a notebook or smartphone in order to perform the sequencing, any added layer such as DNAware makes the sequencing assays more automated and accessible.

Different transferable molecular identification barcodes might does have different functions, which might be used in a single assay and therefore combined. For example, transferable molecular identification barcodes that label a sample in order to detect sample switches and contaminations, and another type of transferable molecular identification barcodes that provide information which bio-informatic pipeline to be used in an assay can be combined.

A more secure form of obtaining sequences from which transferable molecular identification barcodes are built up could be obtained if nucleotide barcode molecules were used for building of transferable molecular identification barcodes that contained 2, or more, minimal barcode sequences instead of one minimal barcode sequence. These 2 minimal barcode sequences could be of the same length or different lengths. Such nucleotide barcodes having two unique sequences can be adjacent to each other, separated by a linker, or could be overlapping. Nucleotide barcodes having one minimal nucleotide barcode sequence are mostly flanked by constant adapters and sequences at both sites. These adapters are in the end needed for amplification and/or sequencing of the nucleotide barcodes. All different nucleotide barcodes thus carry the same adapters. The actual minimal barcode sequence of any nucleotide barcode having these adapters can then be easily determined by a person skilled in the art. This can be circumvented by using 2 unique barcode sequences in the nucleotide barcode. One barcode sequence could be used as a binding site for amplification and/or sequencing primers to characterize and identify the second barcode sequence. For the preparation of a given transferable molecular identification barcode, the different nucleotide barcodes carry the same first barcode sequence, while the second barcode is not constant and equivalent to the minimal barcode sequences described above for nucleotide barcodes that carry only one barcode. A user then needs to know the exact sequence of the first barcode sequence to be used as a primer binding site for amplification and/or sequencing in order to know the primer that is needed for characterization of the (second) minimal barcode sequence. It can be only determined when the sequence of the first barcode sequence is known. The information of the first barcode sequence (in this case primer sequence) could then be restricted and secured to certain persons and/or applications. When such constructs with two minimal barcode sequences are constructed in plasmids, a person skilled in the art might still unravel the actual first barcode sequence by constructing primers for amplification and/or sequencing that flank also the first barcode sequence region, such as in the vector backbone of a plasmid. When such nucleotide barcodes having a given secure first barcode sequence and different possible second barcode sequences are concealed within a mixture of plasmids having random sequences at both the first and second barcode region, the first barcode can be hardly unraveled, especially if these constructs are present at a concentration of each of the different plasmids with random first sequences, even not by a person skilled in the art.

Another application of using nucleotide barcode sequences with two unique minimal barcode sequences would be an application in which the first given unique sequence is used for a given application while another given first sequence is used for another application.

Transferable molecular identification barcodes could be produced, provided and used in applications having either one of these different levels of application, accessibility and/or security. Indeed, when different lots are produced, a different application, accessibility and/or security level could be assigned to a given lot.

An item, sample and/or process is completely quality-assured from the moment that a transferable molecular identification barcode is added. The earlier that a transferable molecular identification barcode is added in a process, the earlier, and therefore more, the process is completely quality-assured. If another transferable molecular identification barcode, or a mix of transferable molecular identification barcodes is found at the end of a process, a sample switch and/or contamination is concluded somewhere in the total process. However, the exact place in the process where the sample switch and/or contamination occurred will not be known. One could narrow down the search for the exact place in a process where a sample switch and/or contamination occurred by spiking processed items or samples at different time points again with transferable molecular identification barcodes. One therefore adds transferable molecular identification barcodes to an item/sample, and the processing thereof, at 2 or even more time points in the total process. For example, when a transferable molecular identification barcode was added at the start to an item or sample, and another transferable molecular identification barcode was added to that processed item or sample in the middle of that process, and the correct second transferable molecular identification barcode is found at the end of the process but not the first transferable molecular identification barcode, it can be concluded that no switch occurred in the second phase of the process. A typical genetic test is built up of several sub-processes, each in turn in general built up of different steps. In a first process, DNA is extracted from a biological sample such as blood, in a second phase a search of DNA mutations is performed by enriching the target region and sequencing. DNA extraction and sequencing are often performed at different locations in a lab, or even in different labs at the same institute/company, or even in different labs at different institutes/companies. In each of the different labs, different persons are involved and have their responsibilities. Adding transferable molecular identification barcodes at different steps in a process, such as when the (processed) sample arrives in a different lab, allows to track a sample switch or contamination to a given sub-process and lab. In this way there will be no discussion where the error has been made and which lab is responsible and has for example to take the charges for doing a new test. This will be of extreme value to NGS sequence core facilities/companies to which many labs outsource their sequencing.

In case that transferable molecular identification barcodes are built up of 6 pairs of nucleotide barcodes, each of the 12 nucleotide barcodes has a fraction of about 8.3% (if no contamination is present). If 2 transferable molecular identification barcodes are added in a given process that do not share any nucleotide barcode sequence, each of the 24 nucleotide barcodes will be only found at a fraction of about 4.15%. The fraction of each nucleotide barcode becomes even smaller when more transferable molecular identification barcodes are added in a given process. The smaller the fraction of each nucleotide barcode found at the end of a process, the less sensitive contamination detection becomes. The use of transferable molecular identification barcodes from different batch productions in which one or both constant flanking sequences, partly or completely, differ between the batches, such as the presence of a different nucleotide barcode sequence identifier sequence per batch, added at respective different steps in a complete process would overcome this problem. In that case, for each transferable molecular identification barcode added at a given time point in the process, the fraction of each nucleotide barcode will remain at 8.3% at the end of the process.

Rather than that different transferable molecular identification barcodes with different constant flanking sequences are used at different steps in a given process, such different transferable molecular identification barcodes with different constant flanking sequences might be added at the same point in a sample. For example, a blood sample that is taken might be used in different tests using different transferable molecular identification barcodes with different constant flanking sequences. Each of these tests might use a given transferable molecular identification barcode with given constant flanking sequences. In that case mixtures of transferable molecular identification barcodes with different constant flanking sequences will be used. For example, next-generation sequencing labs might have a different vision, workflows and protocols for the level of contamination that they want to detect. For example, this information may not be known at the moment when the blood sample is taken by a doctor. For example, this information may not be known until the DNA of the sample is extracted and the quality is known. In that case, transferable molecular identification barcodes with given constant flanking sequencing in which nucleotide barcodes at high amounts allowing very sensitive contamination detection, and transferable molecular identification barcodes with other given constant flanking sequences in which nucleotide barcodes at low amounts are used allowing less sensitive contamination detection, are added to a blood sample. Another example could be that a blood sample is used for DNA and RNA analyses. In that case, a mixture of a DNA-type transferable molecular identification barcode and a RNA-type transferable molecular identification barcode may be added to a biological sample, such as blood.

If transferable molecular identification barcodes are added to a sample, the nucleotide barcodes should not overwhelm the other target nucleic acids under investigation in that (processed) sample. Indeed, one wants to obtain the highest number of sequence reads of the target nucleic acids in order to obtain the highest sensitivity for mutation detection and at the lowest cost. On the other hand, a too low number of each nucleotide barcode in a transferable molecular identification barcode would not allow one to detect or deduce the correct transferable molecular identification barcode, since each nucleotide barcodes should be preferentially present at equimolar amounts to the target nucleic acid(s) under investigation. Biological samples from eukaryotic origin are diploid (2N). If transferable molecular identification barcodes are used that are built up of 6 pairs of nucleotide barcodes they should be practically present at 6N in order to be equimolar to the target nucleic acids. If a blood sample is taken in a 10 ml Vacutainer® tube, the volume of blood that is taken is not always 10 ml. More importantly, the number of white blood cells, which is the source of DNA in blood samples, varies between individuals when measured in cells per ml. So even when exactly the same volume of blood is taken between individuals, the amount of available DNA and extracted DNA in the end can vary to great extent between samples. One fixed amount of transferable molecular identification barcodes will thus not be the most optimal amount for all samples. For example, the amount of circulating DNA in plasma of a blood sample is much lower than the amount of DNA in white blood cells from that blood sample. Preferentially a lower amount of transferable molecular identification barcode is thus added to carriers used for collection of cfDNA than to carriers used for collection of genomic DNA.

Most template preparations for sequencing of samples requires enrichment by capturing of target nucleic acids through capturing oligo's, or by amplification techniques using oligonucleotides. Also the nucleotide barcodes need then to be enriched, respectively enriched by a capturing oligo directed against nucleotide barcodes or primers directed for amplification of the nucleotide barcodes. The number of nucleotide barcodes that are enriched can be normalized to an optimal amount through these capturing oligonucleotides or primers, or more specifically through the concentration of these capturing oligonucleotides or primers. In case that, for example capturing oligonucleotides are present at a lower concentration than their nucleotide barcode targets, once that all these oligonucleotides have found a nucleotide barcode, the unreacted nucleotide barcodes are not captured and washed away. In this way an excess of nucleotide barcode sequences relative to the other target nucleic acids can be removed. Analogously, limiting amounts of primers for amplifying nucleotide barcode sequences in an amplification enrichment protocol relative to the primers directed against amplification of the other target nucleic acids will result in the fact that not all, i.e. excess of, target nucleotide barcodes will find their primer and will not participate in amplification. In this way, a fixed concentration of oligonucleotides directed against nucleotide barcodes will skim of an excess of nucleotide barcodes.

In practice, in a standard capturing or amplification protocol, the concentration of the oligonucleotides is already much higher than the concentration of the targets they need to capture or amplify. Indeed, the oligonucleotides and their respective DNA targets are not present in a one to one molecule relation. In order to skim of an excess of nucleotide barcodes, the concentration of oligonucleotides directed against these nucleotide barcodes sequences for capturing or amplification are then reduced relative to the concentration of the oligonucleotides directed against the other target nucleotide acids. Relative equalization of nucleotide barcode sequences versus other target nucleotide sequences is then not achieved through limiting the number of target nucleotide barcodes participating in the enrichment but by making the finding of a nucleotide barcode sequences kinetically less favorable.

In case when the nucleotide barcodes sequences are present at a lower concentration than the other target nucleotide sequences, with the risk that not sufficient nucleotide barcode sequences will be obtained after sequencing in order to deduce the transferable molecular identification barcode that is present, an optimal nucleotide barcode sequence versus target nucleic acid ratio can be obtained by relative increasing the concentration of oligonucleotides (capturing oligonucleotides or amplification primers) used for enrichment of the nucleotide barcode sequences.

In case that one wants to develop sequencing protocols that are very sensitive for detecting contaminations, this can be achieved by increasing the concentration of the oligonucleotides for enriching the nucleotide barcodes sequences by capturing or amplification, without increasing the amount of transferable molecular identification barcode concentration, such as using other sample containers for biological samples that contain a higher amount (concentration) of transferable molecular identification barcodes.

In case that whole genomes are sequenced, such as in whole genome sequencing and non-invasive prenatal testing, testing for circular tumor DNA, no oligonucleotides are added for enrichment by capturing or amplification. Nevertheless, a capturing oligonucleotide directed against the nucleotide barcode sequences can be used to skim off possibly excess nucleotide barcode sequences versus the whole genome sequences.

Transferable molecular identification barcodes might even be used in highly parallel sequencing applications without preparing them in a NGS template preparation assay. This can be achieved when all primer binding sites for amplification and/or sequencing by highly parallel sequencing are already present in the constant flanking sequences of the transferable molecular identification barcodes and thus need not to be attached during NGS template preparation. Then only a minimal template preparation assay might be performed such as the incorporation of pooling indexes for analyzing different samples in a single experiment.

In many applications, especially in targeted sequencing, different samples/libraries are pooled in a single sequencing experiment. In such pooled libraries, the library to library variability should be as low as possible. If one library is present at a less concentration, a lower amount of sequencing data (in the worst case resulting in insufficient read depth) will be obtained for such a sample/library so that mutations might be missed in that sample, so that that sample possibly needs to be sequenced again in order to obtain additional sequencing reads it order to obtain the desired read depth. This will also increase the cost for sequencing of that sample. If for one sample/library too much sequencing data (and therefore a too high read depth) is obtained than needed, the test is more expensive since more sequenced sequences will be obtained and paid while not needed. Pooled samples/libraries should therefore be equalized. This can be done through determination of the concentration, and therefore the number of DNA molecules, when the molecular weight of the DNA fragments to be sequenced is taken into consideration, or estimated for each library. In case that different libraries have different target nucleic acids (and therefore very likely different sizes of the DNA fragments that will be sequenced) the number of molecules needs to be corrected for the target size. These concentration measurements, calculations and subsequent dilution experiments of each library, and subsequently mixing of the libraries accordingly, is very time consuming.

Equalizing different sequencing libraries to be pooled can also be achieved by a(n) equalizing oligonucleotide(s). This is a simple and seamless bead-based solution replacing the need for library quantification and library dilutions for library normalization as required for any next generation sequencing workflow and which minimizes library-to-library variability. An equalizing oligonucleotide can bind to all target nucleotide sequences. In most applications, such a binding site for an equalizing probe is incorporated during enrichment of the target nucleic acids by amplification in which the primers carry an adapter with such a binding site for an equalization oligo, or during the preparation of a sequencing library by fragmentation and ligation of adapters in which the adapters carry a binding site for an equalization oligo. The equalization binding site might be identical to the binding site for an amplification and/or sequencing primer. When the equalization sequence was present in a primer or ligation adapter, unreacted primers or ligation adapters need to be first removed, so that only true sequencing templates are equalized. When a sample contains target nucleotide sequences derived from transferable molecular identification barcodes and other target nucleic acids, equalization of target nucleotide sequences derived from transferable molecular identification barcodes alone can be achieved by an equalizing oligonucleotide directed in the constant flanking sequence of the nucleotide barcodes. A combination of equalizing oligonucleotides, the first equalization oligonucleotide directed to a constant sequence in the nucleotide barcode sequences, and the second equalization oligonucleotide directed to a sequence incorporated during amplification by a primer or during a ligation by a ligation adapter, may allow to further fine-tune the relative proportion of target nucleotide sequences derived from nucleotide barcode sequences versus other target nucleotide sequences from other target nucleic acids under investigation. When an equalizing oligonucleotide is biotinylated, one can perform an easy bead-based solution for obtaining sequencing libraries with minimized library-to-library variability by adding the same number of such equalizing oligonucleotide(s) to each of the sequencing libraries, and in case that this number of equalizing oligonucleotides is below the number of target nucleotide sequences that can be obtained, the excess number of sequencing template molecules in each sequencing library will be skimmed away and in this way the different sequencing libraries pooled in a sequencing experiment will be equalized in a more optimal way.

Also the Read Until sequencing in real time, as applied in Oxford Nanopore sequencing, would be another way to obtain the most optimal ratio of sequence reads of the nucleotide barcodes sequences versus the other target nucleotide sequences. In Read Until sequencing it is monitored what is being sequenced in each pore, which gives users the option whether to continue and finish sequencing. Since each nanopore channel is individually addressable, the sequencing reaction in each pore can simply be stopped so that a new DNA strand can access that pore for sequencing. Since that each minimal barcode sequence is flanked by constant flanking adapter sequences, the Read Until sequencing can monitor the presence or absence of the constant adaptor sequence of a nucleotide barcode sequence to keep track of the number of nucleotide barcode sequences that are sequenced.

By adjusting the concentration of oligonucleotides for capturing or amplification of nucleotide barcode sequences in the library preparation protocol, or by selective sequencing, there might be no need to produce too many containers for collection of biological samples that each have a different amount of transferable molecular identification barcodes optimized for a given application or technology. If case that still containers need to be produced having different concentrations of transferable molecular identification barcodes for specific downstream processing it is expected that this number is limited to two (high or low) or three (high, moderate, low) concentration types.

Transferable molecular identification barcodes might thus prepared and used at different amounts, depending on the contamination level that needs to be detected. Indeed, the smaller the contamination level that one wants to detect, the deeper NGS sequencing that is needed, and therefore also the higher the amount of nucleotide barcodes that should have been added to an item or sample.

When transferable molecular identification barcodes detect a contamination in a genetic test, the contamination can originate from any substance used in the test. Indeed, besides contaminations between biological samples (blood samples, DNA samples, or processed products thereof in a test process), the contamination could also originate from any product used in that test (DNA extraction, NGS template preparation and/or sequencing reaction). For example, when different samples are combined in a single sequencing experiment through the use of pooling barcodes, pooling barcodes could be also contaminated between each other. Pooling barcodes can be incorporated in sequencing templates through the use of oligonucleotide primers. If a series of different pooling barcode primers is produced, any slight remnants from a former pooling barcode oligonucleotide during synthesis, solubilizing, in the following pooling barcode oligonucleotide results in a contaminated pooling barcode primer (e.g. pooling barcode primer 2 became contaminated with pooling barcode primer 1). When two different samples are processed and sequenced in one experiment, using pooling barcode primers 1 for sample 1 and pooling barcode primers 2 for sample 2, and where pooling barcode primer 2 was contaminated with pooling barcode primer 1. When after sequencing the different sequenced sequences for each of the two samples are grouped and processed according to the respective pooling barcodes in bio-inform atic processes, some reads of sample 2 will show up in the file containing the reads of sample 1 because they were linked with the contaminated pooling barcode 1. After analysis it will thus appear that sample 1 was contaminated by sample 2 during processing, but it might be well possible that both samples were correctly processed during preparation by a technician and no contamination did occur between the samples, while in fact the pooling barcodes were contaminated. Transferable molecular identification barcodes might thus be also used by manufacturing companies of DNA extraction kits, NGS template preparation kits, oligonucleotides to quality control their production processes and end products.

A capturing oligonucleotide for nucleotide barcode sequences will be very likely also needed in protocols in which DNA extraction is not performed on total biological samples. Here, any DNA, being it genomic DNA present in the cells of the biological sample as well as added DNA nucleotide barcodes will be analyzed. When miniaturizing assays, such as on (microfluidic) systems, DNA isolation might not be performed on the total biological sample. For example, DNA extraction may be performed on isolated cells, pathogens (bacteria, viruses) only. When transferable molecular identification barcodes are present in such biological samples, they might not be retained at the step of the cell isolation. A capturing oligonucleotide directed against, and therefore for capturing, nucleotide barcodes can be bound to a pathogen- or cell-sized bead(-structure) so that the nucleotide barcodes will be also retained. In case that, for example, such cells, bacteria or viruses are captured via polyclonal antibodies bound to magnetic beads, these beads can be easily mixed with magnetic beads to which capturing oligonucleotides directed to nucleotide barcodes are bound so that the protocol or assay hardly needs to be modified in order to allow the use of transferable molecular identification barcodes in such assays.

DNA-type transferable molecular identification barcodes can also be used in RNA tests from the moment that RNA has been converted to cDNA. Indeed, many RNA extraction protocols from biological samples destroy (residual) DNA, e.g. with DNase, so that DNA-type transferable molecular identification barcodes, when present in a biological sample, would be destroyed, so that they can be only added when the RNA has been converted to cDNA. In order to quality assure the upstream processing steps preceding the conversion of RNA to cDNA in RNA tests, RNA-type transferable molecular identification barcodes built up of a mix of RNA-type nucleotide barcodes, should be used.

RNA-type nucleotide barcodes can even be made from DNA-type nucleotide barcodes if the upstream constant flanking sequence to the minimal nucleotide barcode region in the DNA-type nucleotide barcodes contains a promoter for priming RNA synthesis. Such an adapter could be, for example a T7 promoter. If the downstream constant flanking sequence to the minimal nucleotide barcode region in RNA-type nucleotide barcodes also contain a stretch of A-residues (e.g. 20, 25, 50, 75, 100, 150, 200, or more A residues), the RNA-type nucleotide barcodes of RNA-type transferable molecular identification barcodes can be also processed in RNA tests that require an mRNA isolation so that the RNA-type nucleotide barcodes are also isolated with m RNA in the m RNA isolation step.

Apart from the application in diagnostic tests, transferable molecular identification barcodes might be also used in research tests. For example, research projects where biological samples (e.g. cell lines) are used that are transfected with expression vectors and studied by highly parallel sequencing assays. This is another reason why the flanking constant sequences should not be encoded in bacterial or viral DNA (and thus not found in cloning vectors, or more specifically cloning vector backbones), or have a sequence that is less than 1%, less than 2%, less than 3%, less than 4%, less than 5%, less than 10%, less than 15%, less than 20%, less than 25%, less than 30%, less than 40%, less than 50% homologous to a sequence encoded in any naturally occurring genome, bacterial or viral DNA. Otherwise they interfere in the highly parallel sequencing and will be also sequenced thereby generating sequenced sequences from the expression vectors which are not needed at the expense of the sequenced sequences that one wants to analyze and money because more sequencing is needed in order to obtain the number of sequenced sequences that one wants.

Apart from their application in tests at the genome and/or transcriptome level, transferable molecular identification barcodes may also find an application in tests of any species. An example are tests that determine the quality and composition of food, even the complete production chain, regarding to their meat, plant, bacteria, fungi content. This would, for instance, allow the detection of fraud in which meat of another animal is present, are mixed with, the meat of a given animal that is indicated on the food product. This can be done at the molecular level through sequence analysis of genomic and/or mitochondrial DNA regions that are highly divergent among species and therefore allow the discrimination among, and therefore detection of a, species. Again here, when food samples are taken for such molecular sequencing tests, food sample switching and/or contamination between food samples can be analogously prevented/monitored by the use (addition) of transferable molecular identification barcodes.

Transferable molecular identification barcodes may be also used for the labelling industrial products, works of art, antiquities, securities and environmental pollutants, quality control of industrial production processes, and so on. Transferable molecular identification barcodes used at higher concentrations would even eliminate the need for amplification, so that the transferable molecular identification barcodes could be directly sequenced on single molecule sequencing devices so that there is hardly any need for sequencing template preparation. This format may become very attractive in portable and handheld single molecule sequencing devices. Such transferable molecular identification barcodes might have additional properties to facilitate easy isolation and/or purification, such as an attachment of a biotin group so that transferable molecular identification barcodes can be easily isolated from (complex) mixtures.

Molecular identification DNA barcodes could be also used in protein assays when aptamer(s) are available that detect the protein(s) under investigation.

Example 1. Use of Transferable Molecular Identification Barcodes in an NGS

Figure 7:
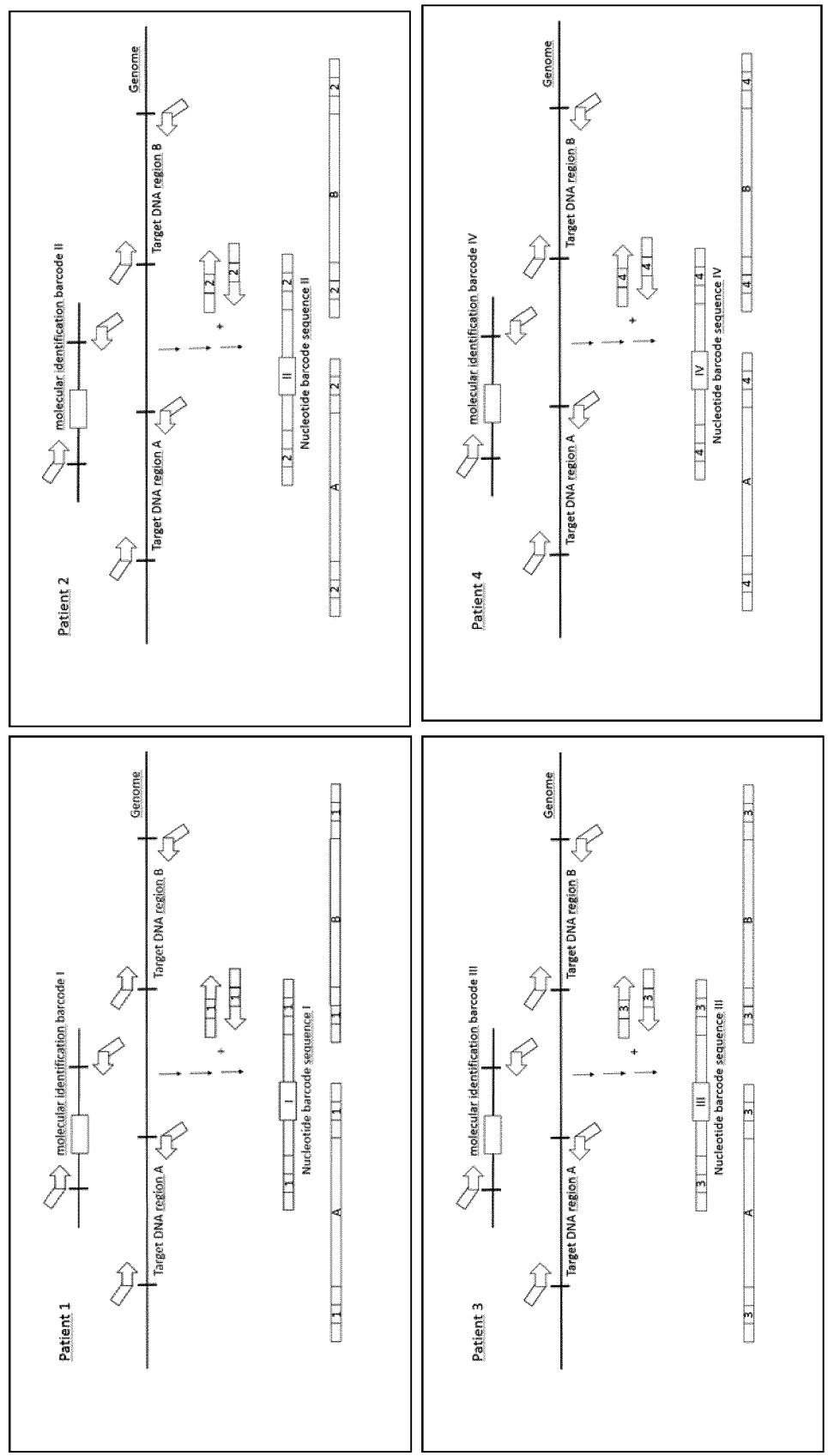
FIG. 7 Use of transferable molecular identification barcodes in an NGS assay using a 2-step PCR protocol for enrichment of target region under investigation; 7A. no sample switch, no contamination, 7B. sample switch, 7C. sample contamination.
Figure 7:
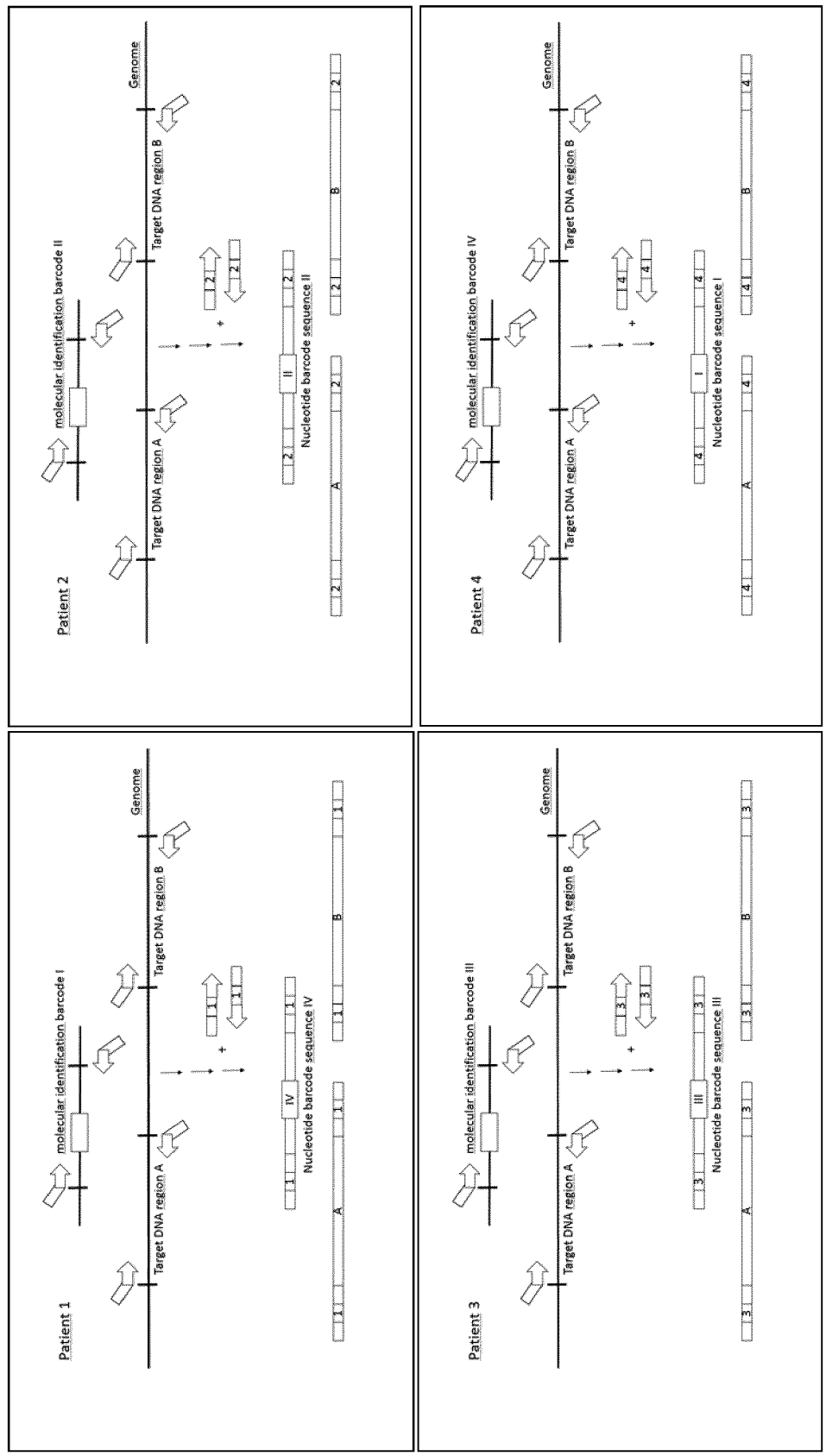
Figure 7:
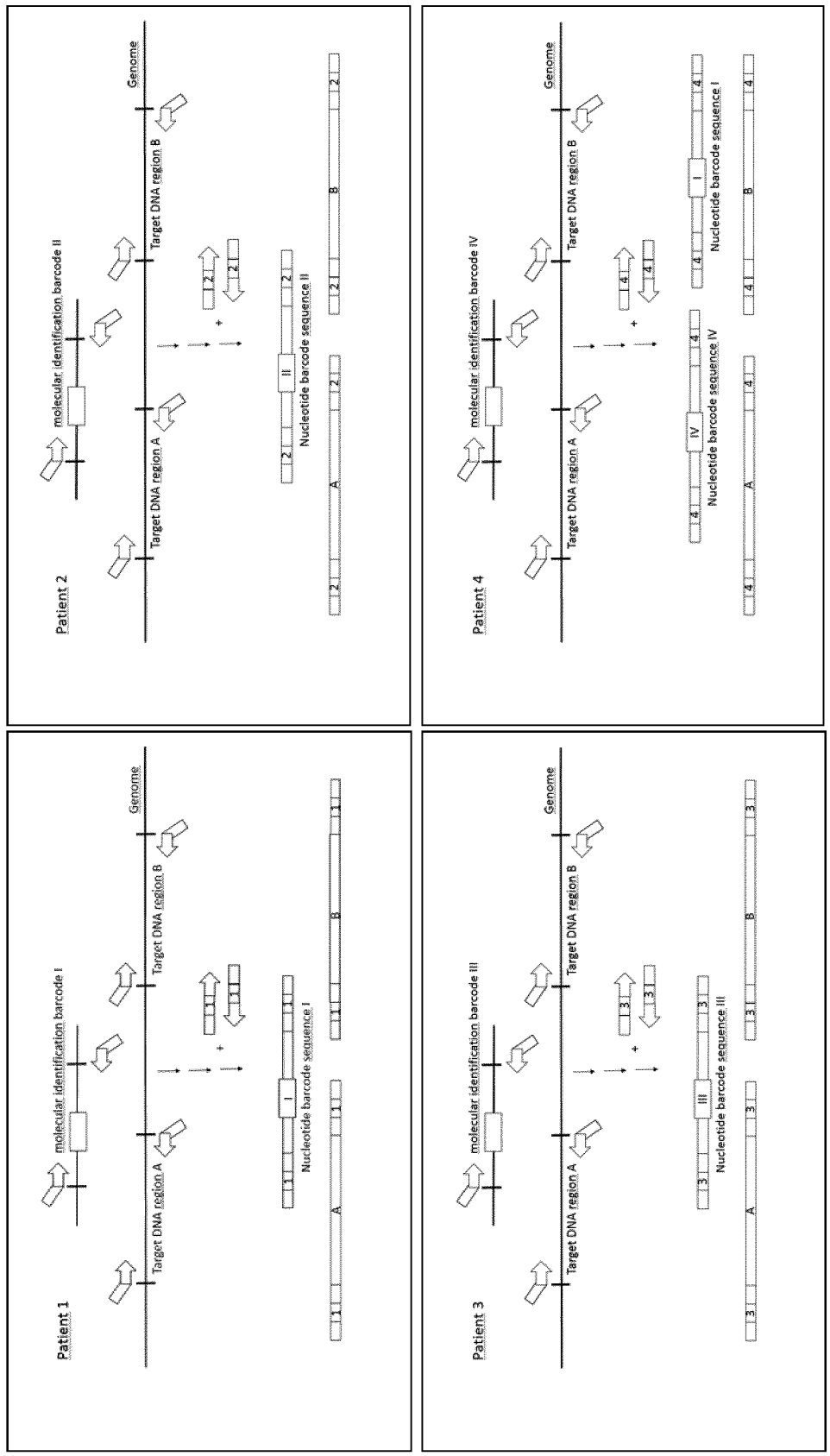

For illustrative means, FIG. 7 shows how the use of transferable molecular identification barcodes in an NGS assay using a 2-step PCR protocol for enrichment of the target regions of nucleic acids under investigation will detect a sample switch or contamination.

A transferable molecular identification barcode was added to patient samples, of which two target nucleic acid regions A and B are of interest. By a two-step multiplex PCR protocol, the two target nucleic acid regions and the minimal nucleotide barcode and its flanking sequences of the transferable molecular identification barcode are amplified. For this purpose, amplicon-specific primers directed to primer binding sites flanking all 3 target nucleic acids regions are amplified. All the amplicon-specific primers carry a 5' universal adapter sequence (one type of universal adapter sequence for the forward primers and another type of universal adapter sequence for the reverse primers). In a second PCR step a pooling barcode is incorporated in all amplicons obtained in the first PCR step. Only one pair of different pooling barcode primers is used per sample. The pooling barcode primers have a primer binding site in the universal adapter sequences that were incorporated in the 3 types of amplicons after the first PCR step, an index sequence, and 5' adapter sequences needed for further processing of the samples for NGS sequencing. For each sample, a different pooling barcode is used. In all 3 amplicons (derived from the two target nucleic acids under investigation and the transferable molecular identification barcode) the same index is incorporated in a given sample. Then all different samples are mixed and sequenced in order to make full economical use of a sequencing chip and reagents. After sequencing, all sequenced sequences are obtained in one or a few large files. By (bio-)informatic means, all sequenced sequences are separated in different files according to the pooling barcode sequence. All sequences with the same pooling barcode sequence, specific for each patient sample, are thus grouped and saved in separate files and individually processed further. For each index/patient file, the minimal nucleotide barcode sequences will be characterized if order to see if there was no sample switch are contamination. If no sample switch and/or contamination is found, the genetic test, i.e. mutations found in the two target nucleotide sequences in that sample, is valid.

Four patient samples are shown. To the first sample transferable molecular identification barcode I was added, and pooling barcodes 1 were used; to the second sample transferable molecular identification barcode II was added, and pooling barcodes 2 were used; to the third sample transferable molecular identification barcode III was added, and pooling barcodes 3 were used; and to the fourth sample transferable molecular identification barcode IV was added, and pooling barcodes 4 were used. In FIG. 7A, no sample switches or contaminations are observed, in FIG. 7B, sample switches did occur during processing between the first and fourth sample, In FIG. 7C, the fourth sample is contaminated with the first sample during processing.

Example 2. Genetic Test Workflows

Figure 8:
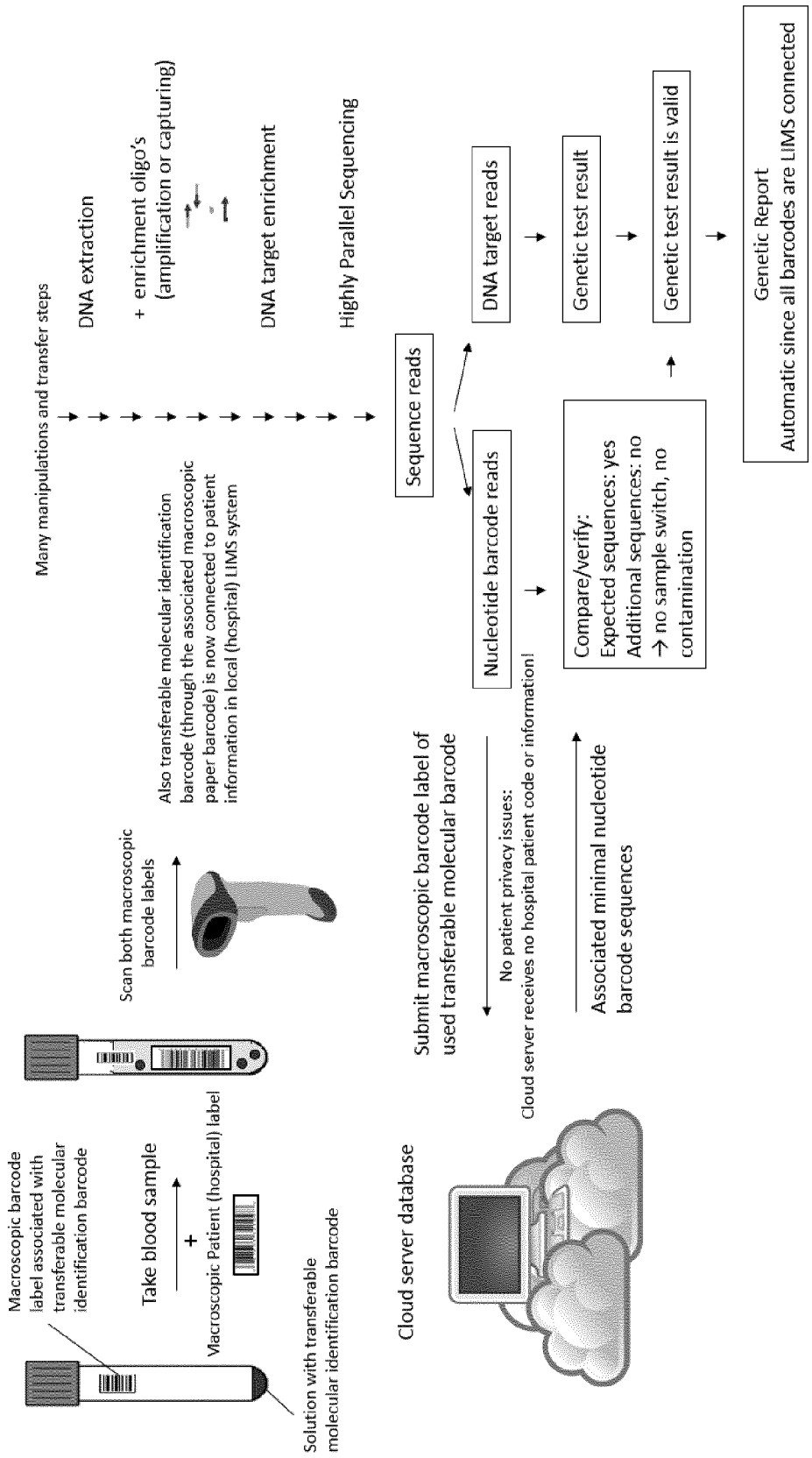
FIG. 8 shows a possible workflow in a genetic test, starting from a blood collector tube that contains a transferable molecular identification barcode until the final valid genetic test report. The bioinformatic processing of both the sequenced sequences derived from the nucleotide barcode sequences and sequenced sequences derived from the target nucleic acids under investigation are performed in parallel.

FIG. 8 shows a workflow in a genetic test, starting from a blood collector tube that contains transferable molecular identification barcode to a final valid genetic test report.

A blood collector tube contains a unique transferable molecular identification barcode and a one to one linked optical macroscopic barcode label. The unique molecular identification barcode and optical barcodes, and their one to one link, are stored in a database, which is accessible through the cloud. From a patient, blood is collected in this blood collector tube. To this blood collector tube another (second) optical barcode paper label from the patient (e.g. generated by the hospital) is attached so that the blood collector tube now has two optical barcode paper labels attached. When the patient optical barcode label is linked to a LIMS system, and when both optical barcode paper labels are scanned, the information of the first optical barcode label becomes also connected to the LIMS, and given its one to one link with a transferable molecular identification barcode, also the transferable molecular identification barcode. The minimal barcode sequence in the transferable molecular identification barcode thus is a transferable alias for the name of the patient. This sample is then processed for sequencing, more specifically a DNA extraction is performed, the target nucleic acid regions of interest (DNA regions of genome under investigation and nucleotide barcode sequences) are enriched, the enriched sequences are prepared as sequencing templates. When whole genome sequencing or circular DNA sequencing is performed, no enrichment is performed. During the preparation of the sequence templates of each sample, pooling barcodes are incorporated. All sequencing templates are then pooled and sequenced. After sequences, all sequences with the same pooling barcode are grouped in single files and further analyzed. Sequence reads derived from the transferable molecular identification barcodes can be identified through the presence of the nucleotide barcode sequence identifier sequence. These sequence reads can be subgrouped and the minimal nucleotide barcode sequences can be characterized, e.g. through their 'extracting' sequences. The other sequences derived from the target nucleic acids under investigation will be characterized for mutations, through mapping and variant calling, so that a genetic test result is obtained. The cloud database is then contacted by presenting the original first optical barcode label paper code, after which the cloud server sends the associated minimal nucleotide barcode sequences to the customer lab. These sent minimal nucleotide barcode sequences will be verified with the obtained minimal barcode sequences from the sequence reads. If the expected minimal barcode sequences are found in the sequence reads, and no additional minimal barcode sequences are found, no sample switch or contamination did occur during processing of the sample, so that the genetic test results are valid. It should be noted that no patient information, even not the hospital generated patient optical paper label code, is transferred outside the lab/hospital, only the optical barcode paper label code that was attached to the original blood collector tube in which blood of the patient was collected.

Figure 9:
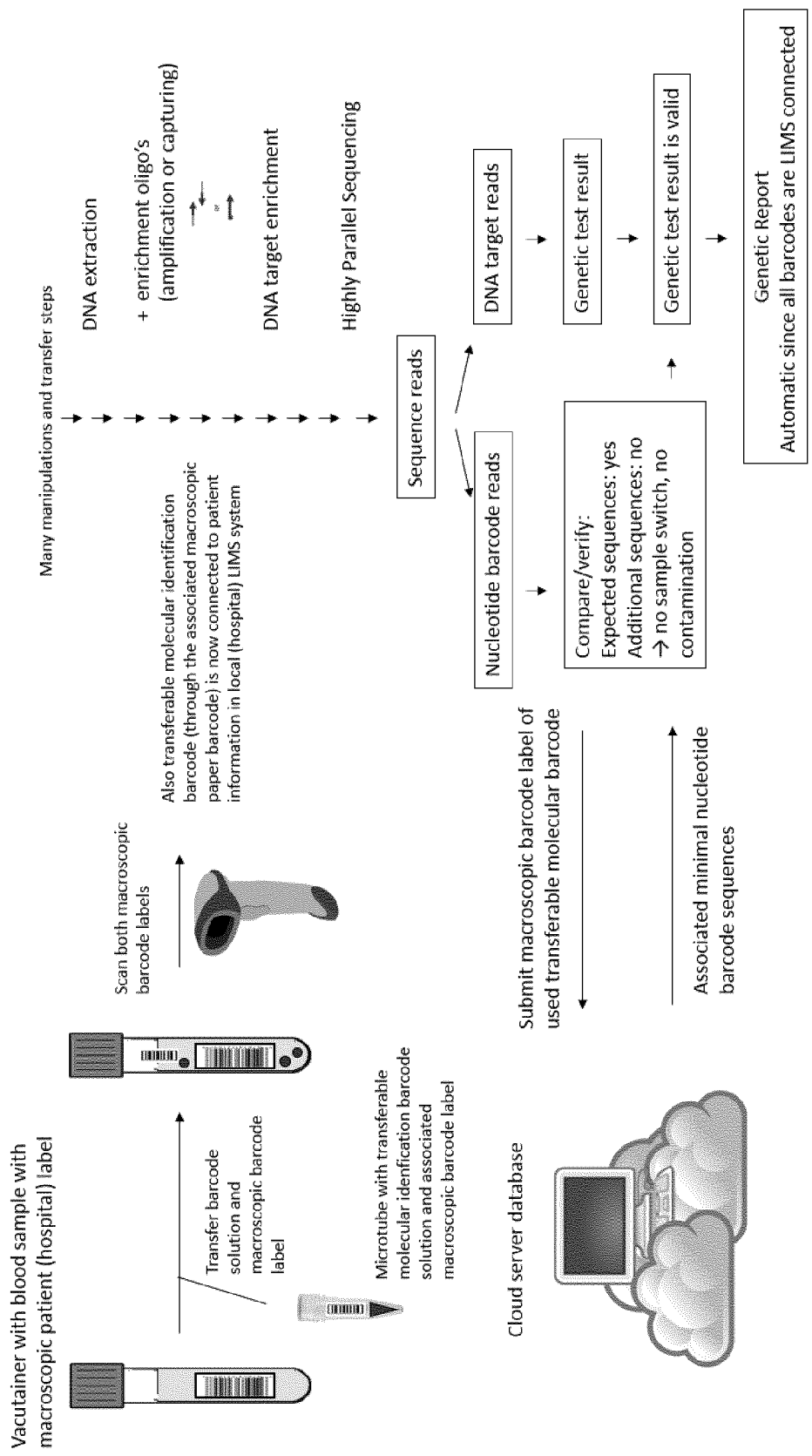
FIG. 9 shows a possible workflow in a genetic test, starting from a microtube that contains a transferable molecular identification barcode that is transferred to a biological sample until the final valid genetic test report.

FIG. 9 shows a workflow in a genetic test, starting from a microtube that contains a transferable molecular identification barcode to a final valid genetic test report.

A microtube tube contains a unique transferable molecular identification barcode and a one to one linked optical macroscopic barcode label. A blood sample is taken in a standard Vacutainer. Immediately afterwards, or when the Vacutainer arrives at a genetic lab, the transferable molecular identification barcode solution of the microtube, and the associated macroscopic barcode label are transferred to the Vacutainer with the blood sample. An alternative is that the associated macroscopic barcode label is not transferred but immediately scanned. The test then proceeds analogous as described in FIG. 8.

Figure 10:
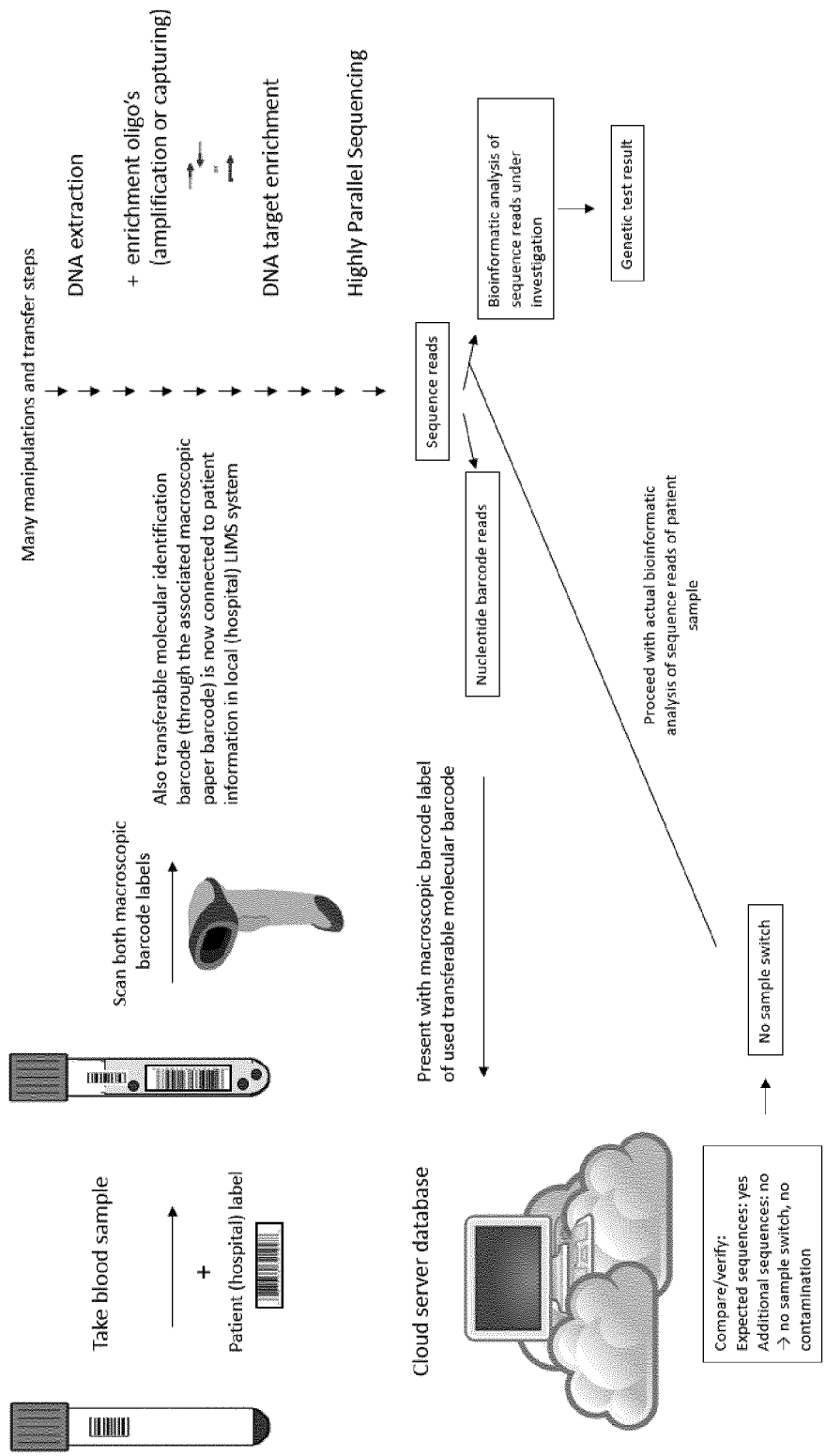
FIG. 10 shows a possible workflow in a genetic test, starting from a blood collector tube that contains a transferable molecular identification barcode until the final valid genetic test report, but in which the bioinformatic processing of the sequenced sequences derived from the nucleotide barcode sequences is first performed, and the bioinformatic processing of the sequenced sequences derived from the target nucleic acids under investigation is only started depending on the result outcome analysis of the sequence reads derived of the nucleotide barcodes, i.e. whether there is no sample switch and/or contamination.

FIG. 10 shows an analogous workflow as described in FIG. 8, but in which the processing of the sequenced sequences differs. Sequenced sequences derived from the nucleotide barcodes and sequenced sequences of the target sample nucleic acids are not analyzed in parallel as described in FIGS. 8 and 9. Only the sequenced sequences of the nucleotide barcodes are analyzed, moreover completely on the cloud, and only if no sample switch is detected, the bioinformatic analysis of the sequenced sequences of the target sample nucleic acids is initiated. Also when a contamination is detected, the bioinformatic analysis of the sequenced sequences of the target sample nucleic acids is initiated and the results are detected and analyzed, but interpreted in the context of the contamination level detected. It is clear that the bio-informatic pipelines can be ordered in different serial and/or parallel steps (algorithms), and can be either partly or completely performed on the cloud of the institution providing the minimal nucleotide barcode sequences, or at the client site (e.g. hospital).

Figure 11:
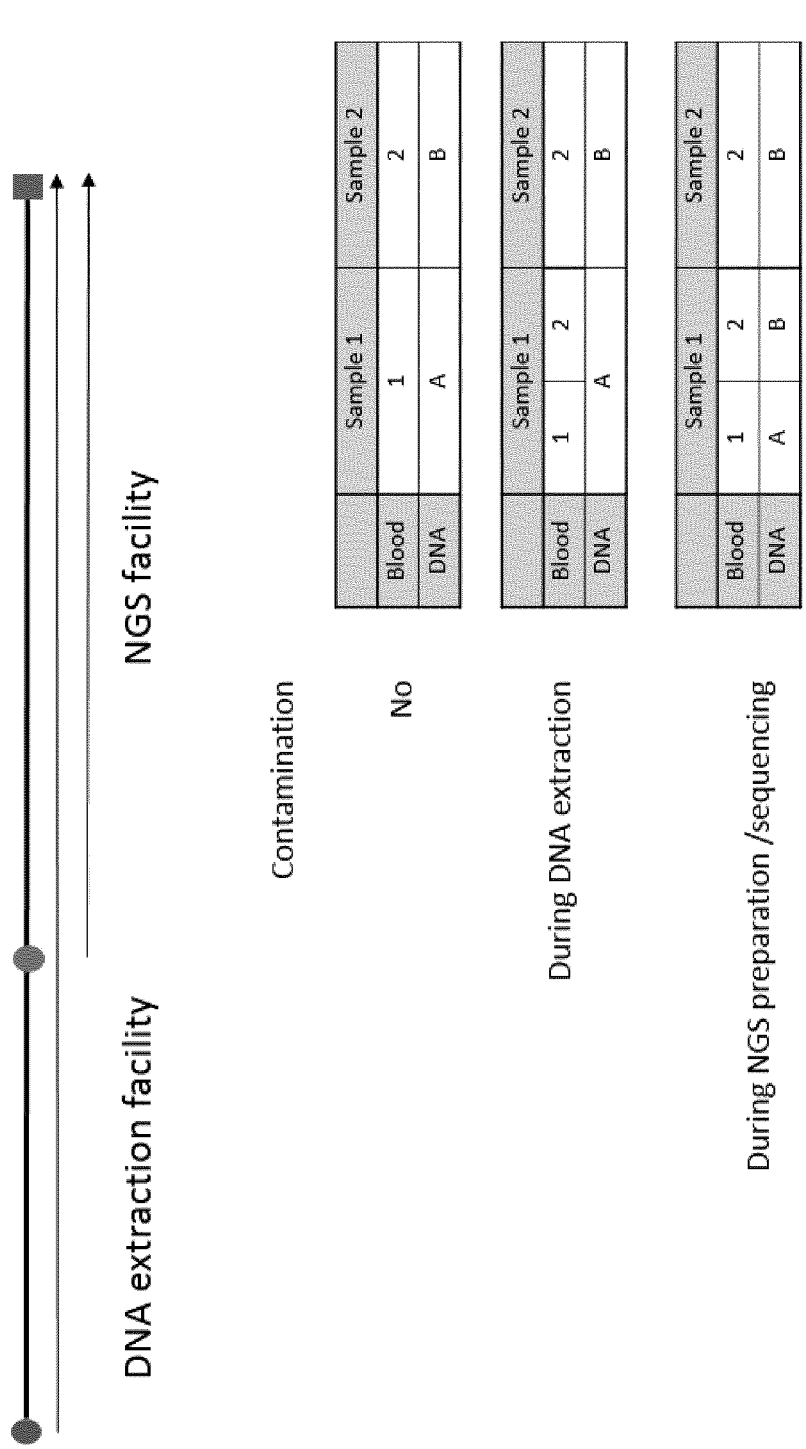
FIG. 11 shows a possible workflow in a genetic test in which a biological sample, or derivates thereof, are twice spiked with different transferable molecular identification barcodes at two different steps in the total test process in order to quality control subprocesses of the total process.

Example 3. Spiking a Sample Testing Process at Different Subprocesses with Transferable Molecular Identification Barcodes FIG. 11 shows two samples that are labelled with transferable molecular identification barcodes when the blood is taken. Blood sample 1 is labeled with transferable molecular identification barcode 1, blood sample 2 is labeled with transferable molecular identification barcode 2, The DNA of both samples is extracted in a DNA extraction facility. Then, the extracted DNA samples are again labelled with transferable molecular identification barcodes. DNA sample 1 is labeled with transferable molecular identification barcode A, DNA sample 2 is labeled with transferable molecular identification barcode B. The DNA samples are then sent to a next generation sequencing facility. The transferable molecular identification barcodes respectively used for labelling blood or DNA are built up of nucleotide barcodes that have respectively different nucleotide barcode sequence identifier sequences through which they can be discriminated. If a sample switch, and/or contamination, did occur, the subprocess (and lab) were the sample switch and/or contamination occurred can now be traced.

When no sample switch or contamination did occur in/between samples 1 and 2, minimal nucleotide barcode sequences 1 and A will be found in sample 1, and minimal nucleotide barcode sequences 2 and B will be found in sample 2, When sample 1 was contaminated with sample 2 during DNA extraction, minimal nucleotide barcode sequences 1, 2 and A will be found in sample 1, When sample 1 was contaminated with sample 2 during NGS template preparation and sequencing, minimal nucleotide barcode sequences 1, 2, A and B will be found in sample 1.

Example 4. Upstream and Downstream Constant Sequences

The example shows embodiments of isolated upstream and downstream constant sequences as described in the present application and depicted for example in FIGS. 3 and 4.

The upstream constant "Sequence 1" [SEQ ID: 1], depicted below, with reference to FIG. 4, shows a sequence located from restriction site RE1 (underlined) till the minimal barcode sequence indicated in black.

The downstream "Sequence 2" [SEQ ID NO: 11], depicted below, with reference to FIG. 4, shows a sequence located from the minimal barcode sequence indicated in black until the restriction site RE2 (underlined).

SEQ ID NO: 2 and 12 are variants without poly A tail.

Variants thereof have alternative restriction site recognition sequences, depending from the cloning site in a vector.

Alternatively, "sequence 1" is the downstream sequence and "sequence 2" is the upstream sequence.

Alternatively, one or both downstream sequences can be the reverse complement sequence of the below depicted sequences.

In alternative embodiments the depicted downstream and/or upstream sequence is a sequence showing more than 70%, more than 80%, more than 90%, more than 95%, more than 97% or more than 99% sequence identity with the sequence identity. Differences in sequence identity can be e.g. the result from a result of adding or deleting recognition sites for restriction enzymes.

Yet alternative embodiments are constant sequences comprising the below depicted sequences, by the presence of additional nucleotides sequence between the indicated restriction site and the constant sequences and/or between the constant sequence and the minimal barcode sequence.

Yet other embodiments are constant sequences comprising or consisting of a fragment of the depicted "sequence 1" and "sequence 2", namely a fragment of at least 200 nucleotides, of at least 300 nucleotides, of at least 350 nucleotides, of at least 375 nucleotides, or of at least 390 nucleotides.

These sequences and a non-limiting set of alternative sequences is depicted in SEQ ID NO: 1 to 20. The above specifications as formulated for "sequence 1" and "sequence 2" [SEQ ID NO 1 and 1] are equally applicable for the other depicted sequences.

[SEQ ID NO: 1]
aagctttgtggatgtacaagtccacaccatgtacactagacgcagcctgt acagatatccatccagtgtactcactgtcgacacggatccaatgcccggg ttctgatagacgaacgacgagatgtgcagtgacttcgaggatcccagatg tgcacgtagtgcaggtagcttgaatgactactacgcctgtagcatcatca cgtagactcgtacagctacatgacggtagctagattgacgactcaagcat gctagtgtcgttactgacctgatgacacagtcgatgcgaccttaatacga ctcactatagggtcaacaagaccctgcagatcccgggatccgcctcttaa gctgcgcaggccaggaattgcacgtcagagcactaaggccgccaccatgg c

[SEQ ID NO: 2]
aagctttgtggatgtacaagtccacaccatgtacactagacgcagcctgt acagatatccatccagtgtactcactgtcgacacggatccaatgcccggg ttctgatagacgaacgacgagatgtgcagtgacttcgaggatcccagatg tgcacgtagtgcaggtagcttgaatgactactacgcctgtagcatcatca cgtagactcgtacagctacatgacggtagctagattgacgactcaagcat gctagtgtcgttactgacctgatgacacagtcgatgcgaccttaaatgct gagagattagggtcaacaagaccctgcagatcccgggatccgcctcttaa gctgcgcaggccaggaattgcacgtcagagcactaaggccgccaccatgg c

[SEQ ID NO: 3]
aagcttctctcgccagctatttaaagtacgagtcgggaggccttagcacg aactgattttccagcctgagtgctgttcttgcatgtaccttctatctaa cgacgtccgtaataggaagtataccaggtcgaactaacgactcctttgcc gtagcgagtgtttcgccaaaagtgtctgggtctactggccaccgtccagc atttctatgcccgtaccaggacccttcgtgtaatcccccatggattttca agaattgaggaaaagtcacgtctccaaggccctacagggccagcggatac tttgaaagcgacgataatatggtcgcttatttcatccaagcccgcgcta aacatggatttttgggatgctatcccgaaagtacgacttggctccaaaggc c

[SEQ ID NO: 4]
aagcttaacttcagctgaagacccgttttcgatccgcggcgagcccggag tgtaaaacgatagacgtgatgcttcggtcttctcaccccttcgaggtcat aacattttgtcatgattgccgtagtgctgatagtcctgagtctaaggca ttcaatacaacgtacctcaggtcaattagactgtccatgactcatcttcc gaagcgcagaatgatacgcagttctcactagttgggacctgctcgacgtc cggttaaggcggatttaactaagcatagggtaccgtcacctgggcaactg aaaatggcctctgtgacgcaagatgcatgttcggtcagctcgttcaaaga cggtatgaaatagagtagacatcagtacatcactcggacaggagcaccta t

[SEQ ID NO: 5]
aagcttgcgcaactttgacgaaatgttggccaatagcatacccgaacacc
gcagggttaatgcctacagctagtgttagtcgttccggtagacatctgtt
aaagccggaagctcgcccgactgtacgaaatcacatctaactatacaact
gcgccactttgcaaatcgagtcacgacgacctgtcccttacggtgcccat
ttgcgctgtaatgccgatcacttcacacaaacaaggcgcttgagagctcg
aacttaggcgatgagggacaagtggtacccaagctccaatagtagaatgt
gtaccatagggccgcggcgagccgcctttgtatcctgaaaaaattctcat
cggcagcgcagtttattatttagttggaagcattagtgaacataacagcg
c

[SEQ ID NO: 6]
aagcttccgtggtgggcagaagagcctagcttactctttatttaaaaacg
ccagtagaatttggtcgggaggatacgatccactgtccaacataaataac
ccgctgtagcctttacacattcacgggttaagtgtagtgcgtgttctgtg
tttctggtttgaataactgttcccactgtcttgaggatcgattctggcca
aaatgtatgaccctctacataggatgtaccccctggggtaggacggaatcg
attacgacccctgatgataatgaccaatcgtgacggtcggtgtctactga
cttcgcctacatccgacgatcctggctaggcgggttgagaacatcacggt
attggggatcgggatgcgcgatcgcgataatgtggacttcgcaggtagta
g

[SEQ ID NO: 7]
aagcttggtggagcgcaaattctatttctgagttgcggcgtcagttgcca
ttgaagtgcccgagctgcatagtctcacggtgagtcctcttgtacgacca
ctagatgcaatgaagcgtgcatggagcgccactctgcaataaaaagccgaa
acgctctgtaaacaagattaatgtctcgtgatgctctgaaaccgtttacc
taacacgaacgataagacgcaacatcttccagagatgattacccgacacg
ctaatgaccgttatcactccccgcacatctgagcgtacttttttgaagtcc
cgaggattgtcacggactaaatacctcgaatatcctgaactacctttgcc
aatggagggaaggacagggacacgctgtcggtactttgtaggcatttggg
t

[SEQ ID NO: 8]
aagcttagctcgacgcacaatccaacaagtagcactgctgtctactaagc
aacgtaatgatccattcagacgagtttggaatgatctgcctcacccaaag
cattaggcagcccctagctttctataggagaccgaaagagcatgagaga
gaactccctgatgacttactgactgcgtgatggttggctccgggacgcgc
aacgcaacactttgtgtggcacgtaacttgtcgcacatatgtaatagctt
caaacccgcctcgtcttctggtgtgcgctcgttcatttaatcgaatagat
tcctctctctactgctggtcaagggcgtattggaaataacaagcaagctc
ctccgagctgagctacgagtcgatccgcccatgttccctcattatcgtct
g

[SEQ ID NO: 9]
aagcttgacctgtagcaccgcaaataatcattgctaatacgattcaagaa
tcgccctcgttatttgtattcacaggtgaccottggcttctactctaaca
cctaaggctgatccaactcagacttaagcggcgcagccgcaaatgtaata
tgttcactgagagagagacgacggctccgtaggtcgaacattcaggtagc
tggagagatcattgcttagcatggcgctcgcggatctgttactgcaaatg
gcaacagactagaaaacaggcctaatatgatctcggaattttcgcctaac
acgctcctttgactggctgtgaggcctaagcgattctggcagcgctgtga
cttatcaagacacgcatgtcactacttgaccggcatcgtgccactctacg
c

[SEQ ID NO: 10]
aagcttttctctgcaacaggcgactatcggggccgggtgccaatctttca
aaagtgtgtaaacgtgcgaccgccagatgtcatgattcaatgtcttacct
cgggctatcgtcataataagtttctaccgtaaggcacgccctaaggacgt
tccgaataaacacgcaccccccgtcgtttcagaaatctcattaccggct
gacatgcctttagatacctcagagaaatctaaccacgtgtgttacgactg
acgtctcaaagagacgagctgctcctagctttcctattggagtatctgtg
cctcttgtgtcgggatttagtggatcaatatgctcccctacgataggtaa
gatttacccgttcgtcaattagagagccgggttttattattcggtcggca
g

[SEQ ID NO: 11]
catcatcaccatcaccattgatctcccagctgtgacacaaataagctagc
ccggggcagcatggaggttaaaattgtgcatccgaccggccaggatacgt
aatattaatgcgcaccgcgcactgaagaatatgatcgaggctcgctgtag
cagcactcagaaaaaaaaaaaaaaaaaaaaaaaaaaaagagtgaataacactc
agatctcgggggcgtgaatgctaaacatacacagagcacgcggtgatgta
taccgctatgtcggtcatgtgctacctacagaagagctaggagtggatga
gcactacacggtttcgggctaagaccatactctcacacgtgtggatgact
cgagacagcagtgtcagagcatgtagctctagagatgacacgatgaattc

[SEQ ID NO: 12]
catcatcaccatcaccattgatctcccagctgtgacacaaataagctagc
ccggggcagcatggaggttaaaattgtgcatccgaccggccaggatacgt
aatattaatgcgcaccgcgcactgaagaatatgatcgaggctcgctgtag
cagcactcagaaccgtaataggaagtataccaaaagagtgaataacactc
agatctcgggggcgtgaatgctaaacatacacagagcacgcggtgatgta
taccgctatgtcggtcatgtgctacctacagaagagctaggagtggatga
gcactacacggtttcgggctaagaccatactctcacacgtgtggatgact
cgagacagcagtgtcagagcatgtagctctagagatgacacgatgaattc

[SEQ ID NO: 13]
cctctacggctccgtatcttaagacaaatgcgttctcgtaggtttgcttc
tacgtgatcatccggggtggtaatccgccctcgatctcctaaggatgaaa
agggttagtttgggccgaatttagttgatcgataagctgacggaaatcttt
actagcggataagctcatcccttcctgggtcaagatgcgagctagtacgg ccgcgtcgctaatctcaatgaccattaactttgcgtagccatgtgtgctg
ctgcggagcgatactattaattgccctttcagttctggttccattgcact
ctgaaggatctccagtttgtcggaatatcacgtaagaacgcttggcagaa
aaagtctctatgctgtaacgcctcgacgtgaaactcgacaatgtgaattc

[SEQ ID NO: 14]
cgtgaggggcacggcgagggagatcacaatatactgtcgtcgtttgattt
cggaacagagccaacgggttcgggtgtcttgtgtgcttcactacatgacc
tcggtaaccagcagatttggtccaccgggtttgtgctggatttaggacaa
ggcgaaatatcatgatatacacagcatcgctttgccgttacattttggc
agccaaatggatcagaggctggtggggattacaccaccttgcccttacat
tggctaacgttttcaacacgtgttcctaaaatgtcagtcatgtcccccca
cacactatagcgctgagtcgatggagatcaaatgaggaatcgaccggaaa
ccttggtgtcactgcctatgcgccggcaatgaacaaaccgaagtgaattc

[SEQ ID NO: 15]
aagctggtagcatatggatagctggcatgttcagataattgctatctggt
atccccacggatgctgatggctgatctttaaggtaaatgacattcgttgt
ctttacgcgccacagtgttgggccaagcagtctagtcatccagggtcatg
ctgagtctgcctcgtagcttaaactgttctaccattacgcggtcacgagc
cgtgacatctcctatttacctggcacggttgcggtggcttgtaccgctcc
agatattataggagtcaagtctaatgtcttatttatgcgagcgtcatagg
accttgtccaataaattgaaaggatacgcccgagctgtggtagctgttag
tgacggcatattgccgagggagccatcgaatgcaatgttgattcgaattc

[SEQ ID NO: 16]
gtgctgttttgttcctcagttcgatacgacctaggaactgatggcgggct
acccggatgatctcgatttgttctctcatgatagcaacggcgtcaagcgt
cagtcttgtctcgatggagggtcgagtagatttggcttggatcttttctcg
tgtaaagtaaatccctgccagaggaccgagctggacggcgaagaagtttt
tttatctctgcacttcgaacgataagcgtcgtctccctggtcgcaaacat
gggcccaaattggcttgcgattgttaaactaccggagttttaatcgcct
aaaccgcggagttaatccatgcaaccaagccagtaggatgaagaagtgcg
tccagtcgatcgttagtgcctggaatttctcttatcggcatcaagaattc

[SEQ ID NO: 17]
tgtccgctctctagcagaagttgtaagttttaactcagtaggctgctact
gaggggattgaacgcatgttatttgggttagtggtaataaatgactgtct
caggcgccatgctagagaacaattttgctggtttgcttacatggagacac
tagtctggtaccgcaccactcatggaatcaagcgtggtaggcccattgtt
tacgtacgagccggctgcatgagggcacatagcatctggataaggcccga
gagacagaggtctgccgagttttacgataccatagctgttgcgccttgca
ttgctatcggttttacctgtcgtctccggcagacggtttattcctcactc
aattaattggctagtgcggctggttatccaacaagcgcattagtgaattc

[SEQ ID NO: 18]
ccggtaacttgctcctgggacgcttaaatggcaatttttaaaggaggcgac
cgaccccctaacctaaggatggtacttggtgaatactatcaaccacctc cgtgacggcggccaattcaatcctgtaacgcgtgtcgtaaaagttcagtt
tgtcgcagggtcgagttacccgtaatcctgggaacgccccccaatccgc
ttcagggctatatgccacacttgaaatcggaagtatcttggcttgagtat
agtctggcgtggtaccacacatctacagtgaggtgaaaggcgcttctggc
aaggtacgttctgcctgacagaattattcgcattagtggatgcgtccctg
gagtgcgtaaagcacactcggcagatgagtgctcggagcggactgaattc

[SEQ ID NO: 19]
tagatgttgtacctgacaaccttctccctgcaaagcgggtgcctaaagat
gttgttacatactccaggcctcgatatggtccaatcaaaatcccatcgga
ccagcgttggaaagtagcacataagcgtgagacctcaggagatccgtgta
taagtgaatactggcattgggggtagttactagtgccgttcaatcgggga
atgactcgggacataacgtctctaatctatatgagggtaccatattcacc
gtaaaagactagagtccaatttggcctttcctcttagggaagagagtaca
aaccgaaaacctggcgatcacgcctgcacagcagaatcttgcctcgtttg
tgtatcattgtggcagaggagcctttaagacatgcgaatagatcgaattc

[SEQ ID NO: 20]
gattttgtcgtaaaacgatcatcatgagatcaagttcgtagaagccctgt
catatttaggagtttgatgatcggcgcgagtgtaagtagcacaccgtatt
ccaccgtgtttacctaacgcgactgcacagtactggcaggtaacgtacaa
actcatacaagggtttccacctctggcatgcttcttcggtatctcgttcg
atgtcgcattaatgcgttgaggaatggggttcatctggtcagggtctgac
cgtttgtaaactaggtgacgagcctgcggacctgatgtttaatctagcgc
cctttatggaaatctgttacgcgcagccagatgtgttgtatcgagggatg
tctaggtcctacacgcgacgatgaaacgggttcgtgtcggataggaattc

REFERENCES

All patents and publications cited before are incorporated herein by reference in their entirety.

23andMe. http://blog.23andme.com/23andme-and-you/update-from-23andme/

Akmaev V R, Wang C J. (2004) Bioinformatics 20:1254-1263.

De Bruyn A, Martin D P, Lefeuvre P. (2014) Methods Mol. Biol. 1115:257-277.

Hamady M, Walker J J, Harris J K, Gold N J, Knight R. (2008) Nat Methods 5:235-237.

Buschmann T, Bystrykh L V. (2013) BMC Bioinformatics 14:272.

Sambrook and Russel: 'Molecular Cloning: A Laboratory Manual', 3rd Edition, 2001, Cold Spring Harbor Laboratory Press.

Norton et al., (2015) N. Engl. J. Med 372:1589-1597.

Taylor et al. (2015) Nat. Genetics 47:717-726.

The invention claimed is:

1. A method of labelling and identifying a plurality of biological samples comprising one or more target sequences of one or more nucleic acids, the method comprising:
   (a) mixing each biological sample from the plurality of biological samples with a unique transferable molecular identification barcode (TMIB) in a carrier from a plurality of carriers at a first time point to form a batch of biological samples, the TMIB comprising a unique combination of at least 2 molecular identification barcodes, wherein said at least 2 molecular identification barcodes do not hybridize to the one or more nucleic acids of the biological samples and are not incorporated in the one or more nucleic acids of the biological sample, wherein each molecular identification barcode comprises:
      (i) a unique minimal nucleotide barcode (MNB) with a length of at least 4 nucleotides, and
      (ii) a constant sequence flanking the MNB at one or both ends, wherein the constant sequence is not encoded in any naturally occurring genome or cloning vector, and wherein the constant sequence comprises:
         an extracting sequence(ES), wherein the ES comprises the same sequence for each TMIB in the batch of biological samples, and wherein the ES is positioned at a defined length from the MNB; and
         an identifier sequence (IS), wherein the IS identifies the MNB;
   wherein each carrier of the plurality of carriers comprises a substrate or a container, and an exterior of each carrier comprises a macroscopic barcode label (MBL) associated with the corresponding TMIB;
   (b) mixing each sample from the batch of biological samples with a unique sample specific pooling barcode (SSPB) in an additional carrier from a plurality of additional carriers at a second time point, wherein the second time point is different from the first time point;
   (c) incorporating each SSPB into the TMIB and the target sequences to create a plurality of dual-labelled samples;
   (d) pooling the dual-labelled samples;
   (e) sequencing the pooled dual-labelled samples by a parallel sequencing method to obtain sequence data comprising:
      (i) the one or more target sequences in the biological sample,
      (ii) the MNBs, and
      (iii) the SSPBs;
   (f) grouping the obtained sequence data according to the SSPBs, wherein each group has a different SSPB;
   (g) identifying the TMIB for each group of obtained sequence data by identifying a sequence between two extracting sequences at the defined length from the MNB or adjacent to one extracting sequence at the defined length from the MNB;
   (h) cross-referencing the identified TMIB to classify each group of obtained sequence data as derived from an accurate sample, a sample switch, and/or a contamination of a sample with and an expected TMIB, wherein the expected TMIB corresponds to the MBL, and wherein:
      (i) a sample is accurate and properly processed between the first and second time points when the identified TMIB is identical to the expected TMIB,
      (ii) a sample switch has occurred between the first and second time points when the identified TMIB is not identical to the expected TMIB, or
      (iii) contamination of a sample has occurred between the first and second time points when more than one TMIB is identified, including the expected TMIB.

2. The method according to claim 1, wherein incorporating the SSPB into the TMIB and the target sequence comprises ligating adaptors comprising the SSPB to the target sequence, thereby generating ligated products.

3. The method according to claim 2, further comprising an enrichment step, the enrichment step comprising:
   generating and/or isolating the sequences of the ligated products through amplification or capture of the ligated products.

4. The method according to claim 3, wherein amplification is selected from 1-step PCR, 2-step PCR, primer extension followed by ligation and PCR, or circularisation based amplification.

5. The method according to claim 1, wherein each TMIB comprises at least two pairs of molecular identification barcodes.

6. The method according to claim 1, wherein the constant sequence is selected from the group consisting of SEQ ID NO: 1 to SEQ ID NO:20.

7. The method according to claim 1, wherein the constant sequence is selected from the group consisting of SEQ ID NO: 1 to SEQ ID NO:11.

8. The method according to claim 1, wherein the constant sequence is selected from the group consisting of SEQ ID NO:1 and SEQ ID NO:11.

9. The method according to claim 1, wherein incorporating the SSPB into the TMIB and the target sequence comprises oligonucleotide synthesis using one or more primers comprising the SSPB.

10. The method of claim 1, wherein the IS comprises the same sequence for each TMIB in the batch of biological samples.

* * * * *